United States Patent
Katoh et al.

(10) Patent No.: US 9,897,731 B2
(45) Date of Patent: Feb. 20, 2018

(54) INFRARED RAY CUTTING FILM, INFRARED RAY CUTTING LAMINATED GLASS, AND INFRARED RAY CUTTING MEMBER

(71) Applicant: FUJIFILM Corporation, Tokyo (JP)

(72) Inventors: Shunya Katoh, Minami-ashigara (JP);
Takao Taguchi, Minami-ashigara (JP);
Kazuhiro Oki, Minami-ashigara (JP);
Masaru Yoshikawa, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 427 days.

(21) Appl. No.: 14/657,807

(22) Filed: Mar. 13, 2015

(65) Prior Publication Data

US 2015/0185383 A1    Jul. 2, 2015

Related U.S. Application Data

(63) Continuation of application No. PCT/JP2013/074631, filed on Sep. 12, 2013.

(30) Foreign Application Priority Data

Sep. 28, 2012 (JP) .................. 2012-218443

(51) Int. Cl.

| | |
|---|---|
| G02B 5/28 | (2006.01) |
| C07D 487/04 | (2006.01) |
| C07D 487/22 | (2006.01) |
| G02B 5/26 | (2006.01) |
| G02B 5/20 | (2006.01) |
| G02B 5/22 | (2006.01) |
| G02B 1/04 | (2006.01) |
| G02F 1/1333 | (2006.01) |

(52) U.S. Cl.
CPC .......... *G02B 5/282* (2013.01); *C07D 487/04* (2013.01); *C07D 487/22* (2013.01); *G02B 1/04* (2013.01); *G02B 5/206* (2013.01); *G02B 5/208* (2013.01); *G02B 5/223* (2013.01); *G02B 5/26* (2013.01); *G02F 1/133365* (2013.01); *Y10T 428/25* (2015.01); *Y10T 428/31616* (2015.04); *Y10T 428/31797* (2015.04)

(58) Field of Classification Search
CPC .......... G02B 5/282; G02B 1/04; G02B 5/206; G02B 5/208; G02B 5/223; G02B 5/26; C07D 487/04; C07D 487/22; G02F 1/133365; Y10T 428/25; Y10T 428/31616; Y10T 428/31797
USPC ...................................................... 428/411.1
See application file for complete search history.

(56) References Cited

U.S. PATENT DOCUMENTS

| | | | |
|---|---|---|---|
| 8,416,375 B2 | 4/2013 | Oki | |
| 2010/0025641 A1 | 2/2010 | Jimbo et al. | |
| 2011/0070407 A1* | 3/2011 | Kato | C08F 2/46 428/172 |
| 2011/0181820 A1 | 7/2011 | Watanabe | |
| 2012/0002125 A1* | 1/2012 | Oki | B32B 7/02 349/16 |

FOREIGN PATENT DOCUMENTS

| | | | |
|---|---|---|---|
| CN | 102310617 A | | 1/2012 |
| JP | 2008-209574 | * | 9/2008 |
| JP | 2008-209574 A | | 9/2008 |
| JP | 2009-227938 | * | 10/2009 |
| JP | 2009-227938 A | | 10/2009 |
| JP | 2010-61119 A | | 3/2010 |
| JP | 2010-90313 A | | 4/2010 |
| JP | 2010-111750 | * | 5/2010 |
| JP | 2010-111750 A | | 5/2010 |

(Continued)

OTHER PUBLICATIONS

Japanese Office Action, dated Oct. 27, 2015, for Japanese Application No. 2012-218443 with an English translation.
English translation of the Chinese Office Action and Search Report dated Jun. 20, 2016, for Chinese Application No. 201380050388.X.
English translation of the Japanese Office Action dated Jun. 7, 2016 for Japanese Application No. 2012-218443.
Japanese Decision of Rejection and English translation thereof, dated Dec. 27, 2016, for corresponding Japanese Application No. 2012-218443.
Decision for Rejection dated Dec. 30, 2016 issued in corresponding Chinese Patent Application No. 201380050388.X.
International Preliminary Report on Patentability and Written Opinion of the International Searching Authority (forms PCT/IB/338, PCT/IB/373, PCT/ISA/237 and PCT/IB/326), dated Apr. 9, 2015, for International Application No. PCT/JP2013/074631, with an English translation of the Written Opinion.

(Continued)

*Primary Examiner* — Leszek Kiliman
(74) *Attorney, Agent, or Firm* — Birch, Stewart, Kolasch & Birch, LLP

(57) ABSTRACT

An infrared ray cutting film having a transparent base, a near infrared ray absorbing layer containing a compound of Formula (1) with a maximum absorption wavelength of from 750 nm to 920 nm, and a near infrared ray reflection layer obtained by fixing a cholesteric liquid crystal phase is excellent in invisibility, robustness and high heat shielding performance. $R^{1a}$ and $R^{1b}$ represent alkyl, aryl or heteroaryl; at least one of $R^2$ and $R^3$ is an electron-withdrawing group, and $R^4$ represents H, alkyl, aryl, heteroaryl, substituted boron, or a metal.

(1)

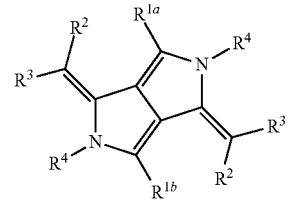

15 Claims, 3 Drawing Sheets

(56) References Cited

FOREIGN PATENT DOCUMENTS

| JP | 2011-68731 | * | 4/2011 |
|---|---|---|---|
| JP | 2011-68731 A | | 4/2011 |
| JP | 2011-107321 | * | 6/2011 |
| JP | 2011-107321 A | | 6/2011 |
| JP | 2011-154215 A | | 8/2011 |
| JP | 2012-13822 | * | 1/2012 |
| JP | 2012-13822 A | | 1/2012 |
| WO | 2010/041769 A1 | | 4/2010 |

OTHER PUBLICATIONS

International Search Report, dated Oct. 29, 2013, issued in PCT/JP2013/074631.
Written Opinion of the International Searching Authority, dated Oct. 29, 2013, issued in PCT/JP2013/074631.
Chinese Office Action and Search Report dated Jun. 20, 2016, for Chinese Application No. 201380050388.X.
Japanese Office Action dated Jun. 7, 2016, for Japanese Application No. 2012-218443.

\* cited by examiner

INFRARED RAY CUTTING FILM, INFRARED RAY CUTTING LAMINATED GLASS, AND INFRARED RAY CUTTING MEMBER

CROSS-REFERENCE TO RELATED APPLICATIONS

This application is a Continuation of PCT International Application No. PCT/JP2013/074631, filed on Sep. 12, 2013, which claims priority under 35 U.S.C. Section 119(a) to Japanese Patent Application No. 2012-218443 filed on Sep. 28, 2012. Each of the above applications is hereby expressly incorporated by reference, in its entirety, into the present application.

BACKGROUND OF THE INVENTION

Field of the Invention

The present invention relates to an infrared ray cutting film, infrared ray cutting laminated glass, and an infrared ray cutting member.

Background Art

In recent years, as one of the energy saving measures for reducing carbon dioxide, heat ray shieldability-imparting materials have been developed for windows of vehicles and buildings. From the viewpoint of heat ray shieldability (heat shielding performance), heat ray reflection types with no reradiation are desired instead of heat ray absorbing types with indoor reradiation of absorbed light (in an amount of approximately ⅓ of the absorbed solar energy), for which various proposals have been made. Further, in addition to heat ray shieldability, high visible light transmittance (invisibility) is demanded for the heat ray shieldability-imparting materials for windows of vehicles and buildings from a viewpoint of safety or the like and robustness (light resistance) is also demanded since the materials are used for a long period of time.

Meanwhile, a technique (for example, see Patent Reference 1) of reflecting infrared rays using a cholesteric liquid crystal is known. Patent Reference 1 discloses that a heat ray shielding material with high heat shielding performance can be provided from a heat ray shielding material which has a cholesteric liquid crystal layer and in which a selective reflection wavelength of the cholesteric liquid crystal layer is in an infrared light region.

Further, an infrared ray cutting technology combining reflection using a cholesteric liquid crystal and absorption of infrared rays using metal fine particles is known. For example, Patent Reference 2 discloses that a near infrared ray absorbing material obtained by laminating a near infrared ray absorbing layer and a cholesteric liquid crystal layer on a base, in which the near infrared ray absorbing layer contains a resin and an inorganic near infrared ray absorbent having an average particle size of 40 nm to 200 nm; the cholesteric liquid crystal layer contains a cholesteric liquid crystal material which has a fixed cholesteric structure and whose selective reflection wavelength is in a red light region; and the color of reflection does not exhibit a blue color and near infrared rays are effectively absorbed by the infrared ray absorbing material having visible light transmittance; and which has high visible light transmittance and excellent transparency can be provided. However, in regard to absorption or reflection by the metal fine particles described in Patent Reference 2, it cannot be said that absorption or reflection in a wavelength region of 750 nm to 920 nm, which has a high level of energy among sunlight, is sufficient.

Patent References 1 and 2 do not contain a description of use of near infrared ray absorbing pigments, but an example of forming a near infrared ray absorbing layer using a near infrared ray absorbing pigment is known. For example, in Patent References 3 and 4, an example of using a pyrrolopyrrole pigment as a near infrared ray absorbing compound is known. However, a combination of a near infrared ray absorbing layer and a near infrared ray reflection layer is not even disclosed or suggested in Patent References 3 and 4.

Patent Reference 5 discloses an example of combining a near infrared ray absorbing layer using two or more kinds of organic pigments that absorb near infrared rays at approximately 800 nm and an infrared ray reflection layer using a cholesteric liquid crystal and describes that the pigment mixing amount can be reduced by making an infrared ray cutting filter for a PDP have such a configuration.

CITATION LIST

Patent References

Patent Reference 1: JP-A-2011-154215
Patent Reference 2: JP-A-2009-227938
Patent Reference 3: JP-A-2010-090313
Patent Reference 4: JP-A-2011-068731
Patent Reference 5: JP-A-2008-209574

SUMMARY OF INVENTION

When organic pigments used in Patent Reference 5 were researched by the present inventors, it has been found that a phthalocyanine pigment has low visible light transmittance, a cyanine pigment has low light resistance, and for a nickel complex pigment, there is a concern about environmental hazards, none of which are satisfactory. As described above, an infrared ray cutting film with excellent invisibility and robustness and high heat shielding performance has not been known so far.

An object to be solved by the present invention is to provide an infrared ray cutting film with excellent invisibility and robustness and high heat shielding performance.

As a result of intensive research conducted by the present inventors to solve the above-described problems, they found that an infrared ray cutting film with excellent invisibility and robustness and high heat shielding performance can be obtained by means of using a combination of a near infrared ray absorbing layer containing a near infrared ray absorbing compound which has a maximum absorption wavelength in a specific range and has a specific structure and a near infrared ray reflection layer obtained by fixing a cholesteric liquid crystal phase, thereby completing the present invention.

The present invention which is specific means for solving the above-described problems is as follows.

[1] An infrared ray cutting film having a transparent base; a near infrared ray absorbing layer that contains a near infrared ray absorbent having a maximum absorption wavelength of from 750 nm to 920 nm; and at least one near infrared ray reflection layer obtained by fixing a cholesteric liquid crystal phase, in which the near infrared ray absorbent is a compound represented by the following general formula (1),

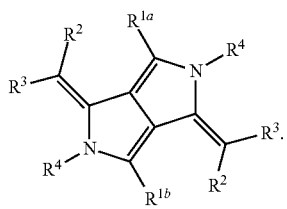

General Formula (1)

In the general formula (1), $R^{1a}$ and $R^{1b}$ may be the same as or different from each other and each independently represent an alkyl group, an aryl group, or a heteroaryl group; $R^2$ and $R^3$ each independently represent a hydrogen atom or a substituent, at least one of $R^2$ and $R^3$ is an electron-withdrawing group, and $R^2$ and $R^3$ may be bonded to each other to form a ring; and $R^4$ represents a hydrogen atom, an alkyl group, an aryl group, a heteroaryl group, substituted boron, or a metal atom, and $R^4$ may be bonded to at least one of $R^{1a}$, $R^{1b}$, and $R^3$ by a covalent bond or a coordinate bond.

[2] In the infrared ray cutting film according to [1], it is preferable that the absorbance of the near infrared ray absorbent at 550 nm is 0.1 or less when the absorbance thereof at the maximum absorption wavelength is 1.

[3] In the infrared ray cutting film according to [1] or [2], it is preferable that the near infrared ray absorbent is in a state in which fine particles of the compound represented by the general formula (1) above are dispersed.

[4] In the infrared ray cutting film according to [3], the number average particle diameter of the fine particles of the compound represented by the general formula (1) is in the range of 5 nm to 500 nm.

[5] In the infrared ray cutting film according to [3] or [4], it is preferable that the near infrared ray absorbing layer has fine particles of the compound represented by the general formula (1) which are dispersed in a UV curable resin or a thermoplastic resin.

[6] In the infrared ray cutting film according to any one of [1] to [5], it is preferable that the near infrared ray absorbing layer is formed by coating.

[7] In the infrared ray cutting film according to any one of [1] to [6], it is preferable that at least one layer among the near infrared ray reflection layers has a maximum value of the reflectance at 750 nm to 1100 nm is 40% or more.

[8] In the infrared ray cutting film according to any one of [1] to [7], it is preferable that the near infrared ray reflection layer is obtained by applying a cholesteric liquid crystal formed of a polymerizable liquid crystal, aligning, and fixing the cholesteric liquid crystal through photopolymerization.

[9] In the infrared ray cutting film according to any one of [1] to [8], it is preferable that the near infrared ray reflection layer includes reflection layers obtained by fixing two layers of cholesteric liquid crystal phases which reflect circularly polarized light beams in directions opposite to each other, and whose reflection wavelength region is in the range of 750 nm to 900 nm and center reflection wavelengths are equivalent to each other.

[10] It is preferable that the infrared ray cutting film according to any one of [1] to [9] further includes at least one of a metal fine particle dispersion and a diimmonium pigment.

[11] In the infrared ray cutting film according to [10], it is preferable that the metal fine particle dispersion is a composite tungsten oxide represented by the following general formula (I).

$$M_xWO_y \quad (I)$$

M represents at least one element selected from the group consisting of Cs, Na, Rb, K, Tl, In, Ba, Li, Ca, Sr, Fe, and Sn; W represents tungsten; O represents oxygen; and $0.1 \leq x \leq 0.5$ and $2.2 \leq y \leq 3.0$.

[12] It is preferable that the infrared ray cutting film according to any one of [1] to [11] further includes at least one among an easily-adhesive layer, a hard coat layer, a UV absorbing layer, an adhesive layer, and a surface protective layer.

[13] An infrared ray cutting laminated glass includes two sheets of glass plates; and the infrared ray cutting film according to any one of [1] to [12] which is interposed between the glass plates.

[14] An infrared ray cutting member includes the infrared ray cutting film according to any one of [1] to [12] and is used for lamination with windows of a building and a vehicle.

[15] An infrared ray cutting member includes the infrared ray cutting film according to any one of [1] to [12] and is used for windshield of a vehicle.

According to the present invention, it is possible to provide an infrared ray cutting film with excellent invisibility and robustness and high heat shielding performance.

DESCRIPTION OF EMBODIMENTS

Hereinafter, preferred embodiments of an infrared ray cutting film, infrared ray cutting laminated glass, and an infrared ray cutting member of the present invention will be described.

The description of the constituent elements described below is made based on typical embodiments of the present invention, but the present invention is not limited thereto. In addition, the numerical range expressed by the wording "a number to another number" in the present specification means a range that includes the former number as the lower limit of the range and the latter number as the upper limit thereof.

[Infrared Ray Cutting Film]

The infrared ray cutting film of the present invention includes a transparent base; a near infrared ray absorbing layer that contains a near infrared ray absorbent whose maximum absorption wavelength is in the range of 750 nm to 920 nm; and at least one layer of near infrared ray reflection layer obtained by fixing a cholesteric liquid crystal phase, in which the near infrared ray absorbent is a compound represented by the following general formula (1):

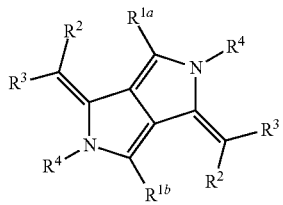

General Formula (1)

In the general formula (1), $R^{1a}$ and $R^{1b}$ may be the same as or different from each other and each independently represent an alkyl group, an aryl group, or a heteroaryl group; $R^2$ and $R^3$ each independently represent a hydrogen atom or a substituent, at least one of $R^2$ and $R^3$ is an electron-withdrawing group, and $R^2$ and $R^3$ may be bonded to each other to form a ring; and $R^4$ represents a hydrogen atom, an alkyl group, an aryl group, a heteroaryl group, substituted boron, or a metal atom, and $R^4$ may be bonded to at least one of $R^{1a}$, $R^{1b}$, and $R^3$ by a covalent bond or a coordinate bond.

With such a configuration, the infrared ray cutting film of the present invention has excellent invisibility and robustness and high heat shielding performance.

Hereinafter, a more preferred embodiment of the infrared ray cutting film of the present invention will be described in detail.

<Characteristics of Infrared Ray Cutting Film>

The visible light transmittance of the infrared ray cutting film of the present invention is preferably 60% or more, more preferably 65% or more, and particularly preferably 70% or more. When the visible light transmittance is 70% or more, the outside is easily seen when the infrared ray cutting film is used as glass for an automobile or glass for a building.

<Configuration of Infrared Ray Cutting Film>

An example of the configuration of the infrared ray cutting film of the present invention will be described with reference to the drawings. However, the present invention is not limited to the drawings.

Figure 1:
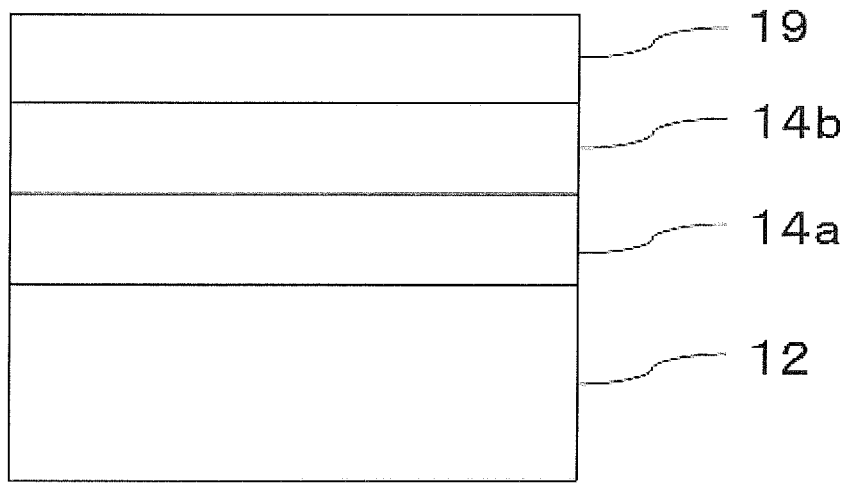
FIG. 1 is a view schematically illustrating an example of an infrared ray cutting film of the present invention.

FIG. 1 is a view schematically illustrating an example of the infrared cutting film of the present invention, which includes a transparent base 12, near infrared ray reflection layers 14a and 14b obtained by fixing two layers of cholesteric liquid crystal layers that are laminated on the transparent base 12, and a near infrared ray absorbing layer 19 including a near infrared ray absorbent that is laminated thereon. The order of lamination of the transparent base 12, the near infrared ray reflection layers 14a and 14b obtained by fixing the cholesteric liquid crystal layers, and the near infrared ray absorbing layer 19 including a near infrared ray absorbent is not particularly limited.

Figure 2:
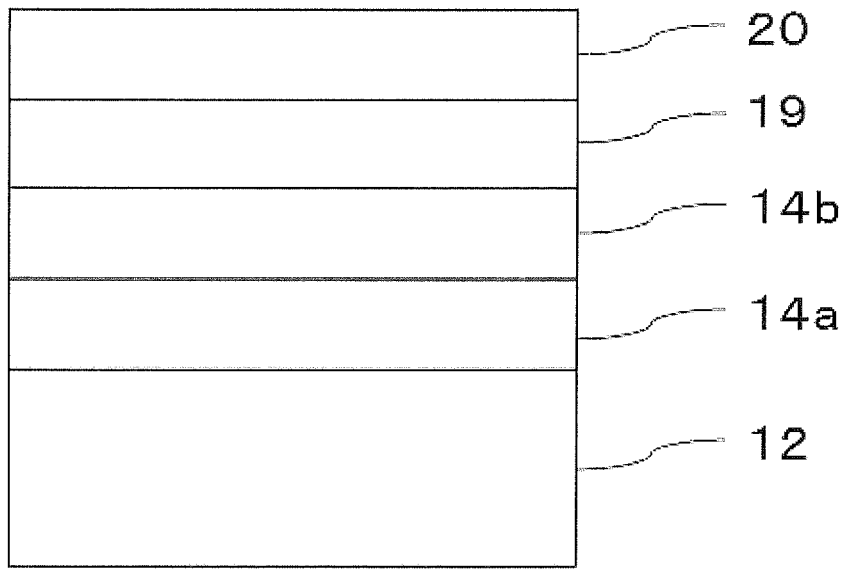
FIG. 2 is a view schematically illustrating another example of an infrared ray cutting film of the present invention.

FIG. 2 is a view schematically illustrating another example of the infrared ray cutting film of the present invention, which includes a transparent base 12, near infrared ray reflection layers 14a and 14b obtained by fixing two layers of cholesteric liquid crystal layers that are laminated on the transparent base 12, a near infrared ray absorbing layer 19 including a near infrared ray absorbent that is laminated thereon, and another infrared ray absorbing layer 20 including a metal fine particle dispersion or a diimmonium pigment that is further laminated thereon. The other infrared ray absorbing layer 20 including a metal fine particle dispersion or a diimmonium pigment may be an infrared ray absorbing layer exhibiting only a function of absorbing infrared rays or may be a layer also serving as another functional layer. As an example of the layer serving as another functional layer, an easily-adhesive layer with respect to a laminated glass interlayer film formed by mixing a diimmonium pigment can be exemplified.

<Transparent Base>

The infrared ray cutting film of the present invention includes a transparent base.

The support is not particularly limited and a known transparent base can be used.

The transparent base is not particularly limited as long as the base material is optically transparent base material and can be appropriately selected according to the purpose, and examples thereof include a base material whose visible light transmittance is 70% or more and preferably 80% or more; and a base material whose transmittance in the near infrared ray region is high.

The shape, structure, size, or material of the transparent base is not particularly limited and can be appropriately selected according to the purpose. The shape thereof may be flat or the like, the structure thereof may be a single layer structure or a laminated structure, and the size thereof can be appropriately selected according to the size of the infrared ray cutting film.

The material of the transparent base is not particularly limited and can be appropriately selected according to the purpose, and examples thereof include a film made of a polyolefin resin such as polyethylene, polypropylene, poly-4-methylpentene-1, or polybutene-1; a polyester resin such as polyethylene terephthalate or polyethylene naphthalate; a polycarbonate resin, a polyvinyl chloride resin, a polyphenylene sulfide resin, a polyether sulfone resin, a polyethylene sulfide resin, a polyphenylene ether resin, a styrene resin, an acrylic resin, a polyamide resin, a polyimide resin, and a cellulose resin such as cellulose acetate, or a laminated film of these. Among these, a polyethylene terephthalate film is particularly preferable.

The thickness of the transparent base is not particularly limited and can be appropriately selected according to the purpose of use of the infrared ray cutting film. The thickness thereof is generally in the range of approximately 10 µm to 500 µm, but it is preferable that the thickness thereof becomes smaller from a viewpoint of requirement for thinning a film. The thickness of the transparent base is preferably in the range of 10 µm to 100 µm, more preferably in the range of 20 µm to 75 µm, and particularly preferably in the range of 35 µm to 75 µm. When the thickness of the support is sufficiently large, adhesion failure is unlikely to occur. Further, when the thickness of the transparent base is sufficiently small, there is a tendency that construction thereof becomes easy since the transparent base is not extremely firm as a material while adhering to a building material or an automobile as the infrared ray cutting film. Further, when the transparent base is sufficiently thin, there is a tendency that the visible light transmittance is increased so that the cost of raw materials can be reduced.

<Near Infrared Ray Absorbing Layer Including Near Infrared Ray Absorbent>

The infrared ray cutting film of the present invention includes a near infrared ray absorbing layer including a near infrared ray absorbent whose maximum absorption wavelength is in the range of 750 nm to 920 nm, and the near infrared ray absorbent is a compound represented by the following general formula (1).

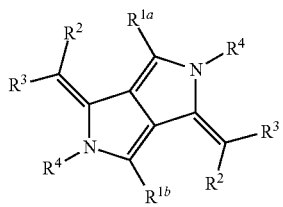

General Formula (1)

In the general formula (1), $R^{1a}$ and $R^{1b}$ may be the same as or different from each other and each independently represent an alkyl group, an aryl group, or a heteroaryl group; $R^2$ and $R^3$ each independently represent a hydrogen atom or a substituent, at least one of $R^2$ and $R^3$ is an electron-withdrawing group, and $R^2$ and $R^3$ may be bonded to each other to form a ring; and $R^4$ represents a hydrogen atom, an alkyl group, an aryl group, a heteroaryl group, substituted boron, or a metal atom, and $R^4$ may be bonded to at least one of $R^{1a}$, $R^{1b}$, and $R^3$ by a covalent bond or a coordinate bond.

(Near Infrared Ray Absorbent)

A near infrared ray absorbent whose maximum absorption wavelength is in the range of 750 nm to 920 nm is used for the near infrared ray absorbing layer. The maximum absorption wavelength of the near infrared ray absorbent is preferably in the range of 770 nm to 900 nm and more preferably in the range of 780 nm to 900 nm.

When the absorbance of the near infrared ray absorbent at the maximum absorption wavelength is 1, it is preferable that the absorbance thereof at 550 nm is 0.1 or less from a viewpoint of improving invisibility and increasing the value of the visible light transmittance of the near infrared absorbing layer.

Hereinafter, a more preferable structure of the compound represented by the general formula (1) above which is used as the near infrared ray absorbent will be described.

In the general formula (1), as the alkyl group represented by $R^{1a}$ and $R^{1b}$, an alkyl group having 1 to 30 carbon atoms is preferable, an alkyl group having 1 to 20 carbon atoms is more preferable, and an alkyl group having 1 to 10 carbon atoms is particularly preferable. Examples thereof include methyl, ethyl, iso-propyl, tert-butyl, n-octyl, n-decyl, n-hexadecyl, 2-methylbutyl, 2-ethylcyclohexyl, cyclopentyl, and cyclohexyl.

As the aryl group represented by $R^{1a}$ and $R^{1b}$, an aryl group having 6 to 30 carbon atoms is preferable, an aryl group having 6 to 20 carbon atoms is more preferable, and an aryl group having 6 to 12 carbon atoms is particularly preferable. Examples thereof include phenyl, o-methylphenyl, p-methylphenyl, biphenyl, naphthyl, anthranyl, phenanthryl, 4-alkoxyphenyl (for example, 4-(2-ethylhexyloxyl) phenyl, 4-(2-methylbutyloxyl)phenyl, or 4-(2-octyldodecyloxy)phenyl), and 4-hydroxyphenyl.

As the heteroaryl group represented by $R^{1a}$ and $R^{1b}$, a heteroaryl group having 1 to 30 carbon atoms is preferable and a hetero aryl group having 1 to 12 carbon atoms is more preferable. Examples of hetero atoms include a nitrogen atom, an oxygen atom, and a sulfur atom. Specific examples of the heteroaryl group include imidazolyl, pyridyl, quinolyl, furyl, thienyl, benzoxazolyl, benzimidazolyl, benzthiazolyl, naphtothiazolyl, m-carbazolyl, and azepinyl.

As the group represented by $R^{1a}$ and $R^{1b}$, an aryl group is preferable, o-methylphenyl or 4-alkoxyphenyl is more preferable, and 4-alkoxyphenyl is particularly preferable. The number of carbon atoms of the alkoxy group in the 4-alkoxy- phenyl group is preferably in the range of 1 to 10, more preferably in the range of 1 to 8. The number is particularly preferably in the range of 1 to 6 from a viewpoint of increasing dispersibility to be easily gathered and shifting absorption to a long wavelength side, and 4-(2-methylbutyloxyl)phenyl is more particularly preferable. Further, the alkoxy group in the 4-alkoxyphenyl group is preferably a branched alkoxy group.

$R^{1a}$ and $R^{1b}$ in the general formula (1) may be the same as or different from each other.

$R^2$ and $R^3$ each independently represent a hydrogen atom or a substituent T, at least one of $R^2$ and $R^3$ is an electron-withdrawing group, and $R^2$ and $R^3$ may be bonded to each other to form a ring. Examples of the substituent T are as follows. These substituents may be further substituted.

Alkyl group (which has preferably 1 to 30 carbon atoms, more preferably 1 to 20 carbon atoms, and particularly preferably 1 to 10 carbon atoms, and examples thereof include methyl, ethyl, iso-propyl, tert-butyl, n-octyl, n-decyl, n-hexadecyl, 2-methylbutyl, 2-ethylcyclohexyl, cyclopentyl, and cyclohexyl.)

Alkenyl group (which has preferably 2 to 30 carbon atoms, more preferably 2 to 20 carbon atoms, and particularly preferably 2 to 10 carbon atoms, and examples thereof include vinyl, allyl, 2-butenyl, and 3-pentenyl.)

Alkynyl group (which has preferably 2 to 30 carbon atoms, more preferably 2 to 20 carbon atoms, and particularly preferably 2 to 10 carbon atoms, and examples thereof include propargyl and 3-pentynyl.)

Aryl group (which has preferably 6 to 30 carbon atoms, more preferably 6 to 20 carbon atoms, and particularly preferably 6 to 12 carbon atoms, and examples thereof include phenyl, p-methylphenyl, biphenyl, naphthyl, anthranil, and phenanthryl.)

Amino group (which has preferably 0 to 30 carbon atoms, more preferably 0 to 20 carbon atoms, and particularly preferably 0 to 10 carbon atoms and contains an alkylamino group, an arylamino group, and a heterocyclic amino group, and examples thereof include amino, methylamino, dimethylamino, diethylamino, dibenzylamino, diphenylamino, and ditolylamino.)

Alkoxy group (which has preferably 1 to 30 carbon atoms, more preferably 1 to 20 carbon atoms, and particularly preferably 1 to 10 carbon atoms, and examples thereof include methoxy, ethoxy, buthoxy, and 2-ethylhexyloxy.)

Aryloxy group (which has preferably 6 to 30 carbon atoms, more preferably 6 to 20 carbon atoms, and particularly preferably 6 to 12 carbon atoms, and examples thereof include phenyloxy, 1-naphthyloxy, and 2-naphtyloxy.)

Aromatic heterocyclic oxy group (which has preferably 1 to 30 carbon atoms, more preferably 1 to 20 carbon atoms, and particularly preferably 1 to 12 carbon atoms, and examples thereof include pyridyloxy, pyrazyloxy, pyrimidyloxy, and quinolyloxy.)

Acyl group (which has preferably 1 to 30 carbon atoms, more preferably 1 to 20 carbon atoms, and particularly preferably 1 to 12 carbon atoms, and examples thereof include acetyl, benzoyl, formyl, and pivaloyl.)

Alkoxy carbonyl group (which has preferably 2 to 30 carbon atoms, more preferably 2 to 20 carbon atoms, and particularly preferably 2 to 12 carbon atoms, and examples thereof include methoxycarbonyl and ethoxycarbonyl.)

Aryloxy carbonyl group (which has preferably 7 to 30 carbon atoms, more preferably 7 to 20 carbon atoms, and particularly preferably 7 to 12 carbon atoms, and examples thereof include phenyloxycarbonyl.)

Acyloxy group (which has preferably 2 to 30 carbon atom, more preferably 2 to 20 carbon atoms, and particularly preferably 2 to 10 carbon atoms, and examples thereof include acetoxy and benzoyloxy.)

Acylamino group (which has preferably 2 to 30 carbon atoms, more preferably 2 to 20 carbon atoms, and particularly preferably 2 to 10 carbon atoms, and examples thereof include acetylamino and benzoylamino.)

Alkoxycarbonylamino group (which has preferably 2 to 30 carbon atoms, more preferably 2 to 20 carbon atoms, and particularly preferably 2 to 12 carbon atoms, and examples thereof include methoxycarbonylamino.)

Aryloxycarbonylamino group (which has preferably 7 to 30 carbon atoms, more preferably 7 to 20 carbon atoms, and particularly preferably 7 to 12 carbon atoms, and examples thereof include phenyloxycarbonylamino.)

Sulfonylamino group (which has preferably 1 to 30 carbon atoms, more preferably 1 to 20 carbon atoms, and particularly preferably 1 to 12 carbon atoms, and examples thereof include methanesulfonylamino and benzenesulfonylamino.)

Sulfamoyl group (which has preferably 0 to 30 carbon atoms, more preferably 0 to 20 carbon atoms, and particularly preferably 0 to 12 carbon atoms, and examples thereof include sulfamoyl, methylsulfamoyl, dimethylsulfamoyl, and phenylsulfamoyl.)

Carbamoyl group (which has preferably 1 to 30 carbon atoms, more preferably 1 to 20 carbon atoms, and particularly preferably 1 to 12 carbon atoms, and examples thereof include carbamoyl, methylcarbamoyl, diethylcarbamoly, and phenylcarbamoyl.)

Alkylthio group (which has preferably 1 to 30 carbon atoms, more preferably 1 to 20 carbon atoms, and particularly preferably 1 to 12 carbon atoms, and examples thereof include methylthio and ethylthio.)

Arylthio group (which has preferably 6 to 30 carbon atoms, more preferably 6 to 20 carbon atoms, and particularly preferably 6 to 12 carbon atoms, and examples thereof include phenylthio.)

Aromatic heterocyclic thio group (which has preferably 1 to 30 carbon atoms, more preferably 1 to 20 carbon atoms, and particularly preferably 1 to 12 carbon atoms, and examples thereof include pyridylthio, 2-benzimizolylthio, 2-benzoxazolylthio, and 2-benzthiazolylthio.)

Sulfonyl group (which has preferably 1 to 30 carbon atoms, more preferably 1 to 20 carbon atoms, and particularly preferably 1 to 12 carbon atoms, and examples thereof include mesyl and tosyl.)

Sulfinyl group (which has preferably 1 to 30 carbon atoms, more preferably 1 to 20 carbon atoms, and particularly preferably 1 to 12 carbon atoms, and examples thereof include methanesulfinyl and benzenesulfinyl.)

Ureido group (which has preferably 1 to 30 carbon atoms, more preferably 1 to 20 carbon atoms, and particularly preferably 1 to 12 carbon atoms, and examples thereof include ureido, methylureido, and phenylureido.)

Phosphoric acid amide group (which has preferably 1 to 30 carbon atoms, more preferably 1 to 20 carbon atoms, and particularly preferably 1 to 12 carbon atoms, and examples thereof include diethyl phosphoric acid amide and phenyl phosphoric acid amide.)

Hydroxy group

Mercapto group

Halogen atom (for example, a fluorine atom, a chlorine atom, a bromine atom, or an iodine atom)

Cyano group

Sulfo group

Carboxyl group

Nitro group

Hydroxamic group

Sulfino group

Hydrazino group

Imino group

Heterocyclic group (which has preferably 1 to 30 carbon atoms and more preferably 1 to 12 carbon atoms, and examples of a hetero atom include a nitrogen atom, an oxygen atom, and a sulfur atom, and specific examples thereof include imidazolyl, pyridyl, quinolyl, furyl, thienyl, piperidyl, morpholino, benzoxazolyl, benzimidazolyl, benzthiazolyl, a carbazolyl group, an azepinyl group.)

Silyl group (which has preferably 3 to 40 carbon atoms, more preferably 3 to 30 carbon atoms, and particularly preferably 3 to 24 carbon atoms, and examples thereof include trimethylsilyl and triphenylsilyl.)

At least one of $R^2$ and $R^3$ is an electron-withdrawing group. A substituent whose σp value (sigma para value) of Hammett is positive generally acts as an electron-withdrawing group. Preferred examples of the electron-withdrawing group include a cyano group, an acyl group, an alkyloxy carbonyl group, an aryloxy carbonyl group, a sulfamoyl group, a sulfinyl group, and a heterocyclic group. These electron-withdrawing groups may be further substituted.

The substituent constant σ value of Hammett will be described. The Hammett rule is a rule of thumb proposed by L. P. Hammett in 1935 for quantitatively discussing the influence of a substituent on reaction or equilibrium of a benzene derivative, and the validity thereof is widely recognized in recent days. The substituent constants acquired by the Hammett rule include a σp value and a σm value. These values can be found in many ordinary books. For example, the values are described in "*Lange's Handbook of Chemistry*" edited by J. A. Dean, 12$^{th}$ edition, 1979 (Mc Graw-Hill); "*Area of Chemistry*" p. 96 to 103, special edition, No. 122, 1979 (Nankodo Co., Ltd.); and Chem. Rev., p. 165 to 195, vol. 91, 1991. In the present invention, a substituent whose substituent constant σp value of Hammett is 0.2 or more can be exemplified as an electron-withdrawing group. The σp value is preferably 0.25 or more, more preferably 0.3 or more, and particularly preferably 0.35 or more. The upper limit thereof, which is not particularly limited, is preferably 0.80.

Specific examples thereof include a cyano group (0.66), a carboxyl group (—COOH: 0.45), an alkoxy carbonyl group (—COOMe: 0.45), an aryloxy carbonyl group (—COOPh: 0.44), a carbamoyl group (—CONH$_2$: 0.36), an alkyl carbonyl group (—COMe: 0.50), an aryl carbonyl group (—COPh: 0.43), an alkyl sulfonyl group (—SO$_2$Me: 0.72), and an aryl sulfonyl group (—SO$_2$Ph: 0.68). Among these, a cyano group is particularly preferable.

In the present specification, Me represents a methyl group and Ph represents a phenyl group. Moreover, the values in parentheses are σp values of typical substituents which are excerpted from p. 165 to 195 of Chem. Rev., vol. 91, 1991.

Further, in a case where $R^2$ and $R^3$ are bonded to each other to form a ring, it is preferable to form a ring of a 5-membered to 7-membered ring (preferably a 5-membered and 6-membered ring). As a ring to be formed, a ring used as an acidic nucleus in a merocyanine pigment is generally preferable and specific examples thereof are as follows.

(a) a 1,3-dicarbonyl nucleus: a 1,3-indandione nucleus, 1,3-cyclohexanedione, 5,5-dimethyl-1,3-cyclohexanedione, 1,3-dioxane-4,6-dione, or the like (b) a pyrazolinone nucleus: 1-phenyl-2-pyrazolin-5-one, 3-methyl-1-phenyl-2-pyrazolin-5-one, 1-(2-benzothiazoyl)-3-methyl-2-pyrazolin-5-one, or the like (c) an isoxazolinone nucleus: 3-phenyl-2-isoxazolin-5-one, 3-methyl-2-isoxazolin-5-one, or the like (d) an oxyindole nucleus: 1-alkyl-2,3-dihydro-2-oxyindole or the like (e) a 2,4,6-triketohexahydropyrimidine nucleus: barbituric acid or 2-thiobarbituric acid and a derivative thereof, or the like. Examples of the derivatives include 1-alkyl derivatives such as 1-methyl or 1-ethyl derivative; 1,3-dialkyl derivatives such as 1,3-dimethyl, 1,3-diethyl or 1,3-dibutyl derivative; 1,3-diaryl derivatives such as 1,3-diphenyl, 1,3-di(p-chlorophenyl) or 1,3-di(p-ethoxycarbonylphenyl) derivative; 1-alkyl-3-aryl derivatives such as 1-ethyl-3-phenyl derivative; and 1,3-diheterocyclic derivatives such as 1,3-di(2-pyridyl) derivative.

(f) a 2-thio-2,4-thiazolidinedione nucleus: rhodanine, a derivative thereof, or the like. Examples of the derivative include 3-alkyl rhodanine such as 3-methyl rodanine, 3-ethyl rhodanine, or 3-allyl rhodanine; 3-aryl rhodanine such as 3-phenyl rhodanine; and 3-position heterocycle-substituted rhodanine such as 3-(2-pyridyl)rhodanine.

(g) a 2-thio-2,4-oxazolidinedione(2-thio-2,4-(3H,5H)-oxazoledione nucleus: 3-ethyl-2-thio-2,4-oxazolidinedione or the like (h) a thianaphthenone nucleus: 3(2H)-thianaphthenone-1,1-dioxide or the like (i) a 2-thio-2,5-thiozolidinedione nucleus: 3-ethyl-2-thio-2,5-thiazolidinedione or the like (j) a 2,4-thiozolidinedione nucleus: 2,4-thiazolidinedione, 3-ethyl-2,4-thiazolidinedione, 3-phenyl-2,4-thiazolidinedione, or the like (k) a thiazolin-4-one nucleus: 4-thiazolinone, 2-ethyl-4-thiazolinone, or the like (l) a 4-thiazolidinone nucleus: 2-ethylmercapto-5-thiazolin-4-one, 2-alkylphenylamino-5-thiazolin-4-one, or the like (m) a 2,4-imidazolidinedione (hydantoin) nucleus: 2,4-imidazolidinedione, 3-ethyl-2,4-imidazolidinedione, or the like (n) a 2-thio-2,4-imidazolidinedione (2-thiohydantoin) nucleus: 2-thio-2,4-imidazolidinedione, 3-ethyl-2-thio-2,4-imidazolidinedione, or the like (o) an imidazolin-5-one nucleus: 2-propylmercapto-2-imidazolin-5-one, or the like (p) 3,5-pyrazolidinedione: 1,2-diphenyl-3,5-pyrazolidinedione, 1,2-dimethyl-3,5-pyrazolidinedione, or the like (q) a benzothiophen-3-one nucleus: benzothiophen-3-one, oxobenzothiophen-3-one, dioxobenzothiophen-3-one, or the like (r) an indanone nucleus: 1-indanone, 3-phenyl-1-indanone, 3-methyl-1-indanone, 3,3-diphenyl-1-indanone, 3,3-dimethyl-1-indanone, or the like The σp value of $R^2$ and $R^3$ in a case of forming a ring cannot be acquired, but in the present invention, the σp value thereof in the case of forming a ring is defined under the assumption that $R^2$ and $R^3$ are respectively substituted with a partial structure of a ring. For example, in a case of forming a 1,3-indanedione ring, it is considered that $R^2$ and $R^3$ are respectively substituted with a benzoyl group.

Preferred examples of the ring formed by $R^2$ and $R^3$ being bonded include a 1,3-dicarbonyl nucleus, a pyrazolinone nucleus, a 2,4,6-triketohexahydropyrimidine nucleus (including a thioketone derivative), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, a 3,5-pyrazolidinedione nucleus, a benzothiophen-3-one nucleus, and an indanone nucleus; and more preferred examples thereof include a 1,3-dicarbonyl nucleus, a 2,4,6-triketohexahydropyrimidine nucleus (including thioketone derivative), a 3,5-pyrazolidinedione nucleus, a benzothiophen-3-one nucleus, and an indanone nucleus.

It is particularly preferable that $R^3$ represents a heterocycle. Particularly preferred examples of the heterocycle include a pyrazole ring, a triazole ring, an oxazole ring, an imidazole ring, an oxadiazole ring, a thiadiazole ring, a triazole ring, a pyridine ring, a pyridazine ring, a pyrimidine ring, and a pyrazine ring; and a benzo-condensed ring thereof, a naphtho-condensed ring, or a complex of these condensed rings.

Two $R^3$'s in the general formula (1) may be the same as or different from each other, and two $R^3$'s may be the same as or different from each other.

When the group represented by $R^4$ is an alkyl group, an aryl group, or a heteroaryl group, the group has the same definition as those described in the section of $R^{1a}$ and $R^{1b}$ and the preferred examples thereof are the same. When the group represented by $R^4$ is substituted boron, the substituent thereof is the same as the substituent T described above in the section of $R^2$ and $R^3$ and preferred examples thereof include an alkyl group, an aryl group, and a heteroaryl group. Further, when the group represented by $R^4$ is a metal atom, preferred examples thereof include transition metal, magnesium, aluminum, calcium, barium, zinc, or tin; more preferred examples thereof include aluminum, zinc, tin, vanadium, iron, cobalt, nickel, copper, paradium, iridium, or platinum, and particularly preferred examples thereof include aluminum, zinc, vanadium, iron, copper, paradium, iridium, or platinum.

It is particularly preferable that $R^4$ is substituted boron. Examples of the substituted boron include difluoroboron, diphenyl boron, dibutyl boron, dinaphthyl boron, and catechol boron. Among these, diphenyl boron is particularly preferable.

$R^4$ may be bonded to $R^{1a}$, $R^{1b}$, and/or $R^3$ by a covalent bond or a coordinate bond and $R^4$ is particularly preferably bonded to $R^3$ by a coordinate bond.

Two $R^4$'s in the general formula (1) may be the same as or different from each other.

The compound represented by the general formula (1) is preferably a compound represented by any one of following general formulae (2), (3), and (4) and the compound represented by the general formula (3) is more preferable.

General Formula (2)

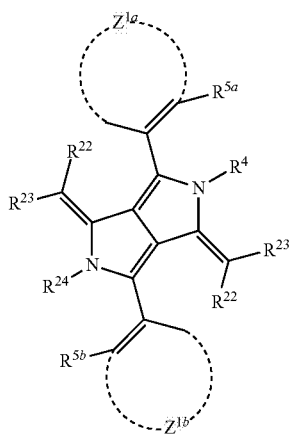

In the general formula (2) described above, $Z^{1a}$ and $Z^{1b}$ each independently represent an atom group forming an aryl ring or a heteroaryl ring. $R^{5a}$ and $R^{5b}$ each independently represent any one of an aryl group having 6 to 20 carbon atoms, a heteroaryl group having 4 to 20 carbon atoms, an alkyl group having 1 to 20 carbon atom, an alkoxy group having 1 to 20 carbon atoms, an alkoxycarbonyl group having 1 to 20 carbon atom, a carboxyl group, a carbamoyl group having 1 to 20 carbon atoms, a halogen atom, or a cyano group, and $R^{5a}$ or $R^{5b}$ and $Z^{1a}$ or $Z^{1b}$ may be bonded to each other to form a condensed ring. $R^{22}$ and $R^{23}$ each independently represent a cyano group, an acyl group having 1 to 6 carbon atoms, an alkoxycarbonyl group having 1 to 6 carbon atoms, an alkyl or arylsulfinyl group having 1 to 10 carbon atoms, or a nitrogen-containing heteroaryl group having 3 to 20 carbon atoms, or $R^{22}$ and $R^{23}$ are bonded to each other to form a cyclic acidic nucleus. $R^{24}$ represents a hydrogen atom, an alkyl group having 1 to 20 carbon atoms, an aryl group having 6 to 20 carbon atoms, a heteroaryl group having 4 to 20 carbon atoms, a metal atom, or substituted boron including a halogen atom, an alkyl group having 1 to 10 carbon atoms, an aryl group having 6 to 20 carbon atoms, or a heteroaryl group having 4 to 20 carbon atoms as a substituent, and $R^{23}$ may include a covalent bond or a coordinate bond. Further, the pigment may further include a substituent.

General Formula (3)

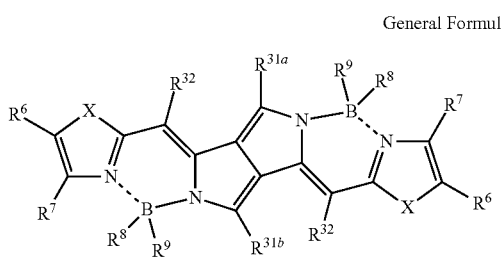

In the general formula (3), $R^{31a}$ and $R^{31b}$ each independently represent an alkyl group having 1 to 20 carbon atoms, an aryl group having 6 to 20 carbon atoms, or a heteroaryl group having 3 to 20 carbon atoms. $R^{32}$ represents a cyano group, an acyl group having 1 to 6 carbon atoms, an alkoxycarbonyl group having 1 to 6 carbon atoms, an alkyl or an arylsulfinyl group having 1 to 10 carbon atoms, or a nitrogen-containing heteroaryl group having 3 to 10 carbon atoms. $R^6$ and $R^7$ each independently represent a hydrogen atom, an alkyl group having 1 to 10 carbon atoms, an aryl group having 6 to 10 carbon atoms, or a heteroaryl group having 4 to 10 carbon atoms, $R^6$ and $R^7$ may be bonded to each other to form a ring, and examples of the ring to be formed include an alicycle having 5 to 10 carbon atoms, an aryl ring having 6 to 10 carbon atoms, or a heteroaryl ring having 3 to 10 carbon atoms. $R^8$ and $R^9$ each independently represent an alkyl group having 1 to 10 carbon atom, an alkoxy group having 1 to 10 carbon atoms, an aryl group having 6 to 20 carbon atoms, or a heteroaryl group having 3 to 10 carbon atoms. X represents an oxygen atom, a sulfur atom, —NR—, —CRR'—, or —CH=CH—. Here, R and R' each independently represent a hydrogen atom, an alkyl group having 1 to 10 carbon atoms, or an aryl group having 6 to 10 carbon atoms.

General Formula (4)

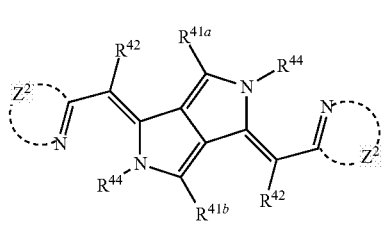

In the general formula (4), $R^{41a}$ and $R^{41b}$ represent different groups from each other and examples of the groups include an alkyl group having 1 to 20 carbon atoms, an aryl group having 6 to 20 carbon atoms, and a heteroaryl group having 3 to 20 carbon atoms. $R^{42}$ represents a cyano group, an acyl group having 1 to 6 carbon atoms, an alkoxycarbonyl group having 1 to 6 carbon atoms, an alkyl or arylsulfinyl group having 1 to 10 carbon atoms, or a nitrogen-containing heteroaryl group having 3 to 10 carbon atoms. $Z^2$ represents an atom group forming a nitrogen-containing hetero 5-membered or 6-membered ring together with —C=N—, and examples of the nitrogen-containing heterocycle include a pyrazole ring, a triazole ring, an oxazole ring, an imidazole ring, an oxadiazole ring, a thiadiazole ring, a triazole ring, a pyridine ring, a pyridazine ring, a pyrimidine ring, and a pyrazine ring; and a benzo-condensed ring thereof, a naphtho-condensed ring, or a complex of these condensed rings. $R^{44}$ represents a hydrogen atom, an alkyl group having 1 to 20 carbon atoms, an aryl group having 6 to 20 carbon atoms, a heteroaryl group having 4 to 20 carbon atoms, a metal atom, or substituted boron including a halogen atom, an alkyl group having 1 to 10 carbon atoms, an aryl group having 6 to 20 carbon atoms, or a heteroaryl group having 4 to 20 carbon atoms as a substituent, and may include a covalent bond or a coordinate bond by being bonded to a nitrogen-containing heterocycle formed by $Z^2$. Further, the near infrared absorbing pigment may further include a substituent.

<Regarding General Formula (2) Above>

In the general formula (2), $Z^{1a}$ and $Z^{1b}$ each independently represent an atom group forming an aryl ring or a heteroaryl ring. An aryl ring and a heteroaryl ring to be formed have the same definitions as those of the aryl group and the heteroaryl group described as substituents of $R^2$ and $R^3$ in the general formula (1), and the preferable ranges thereof are also the same. $Z^{1a}$ and $Z^{1b}$ are preferably the same as each other.

$R^{5a}$ and $R^{5b}$ each independently represent any one of an aryl group having 6 to 20 carbon atoms, a heteroaryl group having 4 to 20 carbon atoms, an alkyl group having 1 to 20 carbon atom, an alkoxy group having 1 to 20 carbon atoms, an alkoxycarbonyl group having 1 to 20 carbon atom, a carboxyl group, a carbamoyl group having 1 to 20 carbon atoms, a halogen atom, or a cyano group. Specifically, $R^{5a}$ and $R^{5b}$ have the same definitions as those described in the section of $R^2$ and $R^3$ in the general formula (1) and the preferable ranges thereof are also the same. $R^{5a}$ and $R^{5b}$ are preferably the same as each other.

$R^{5a}$ or $R^{5b}$ and $Z^{1a}$ or $Z^{1b}$ may be bonded to each other to form a condensed ring, and examples of the condensed ring include a naphthyl ring and a quinoline ring.

The invisibility can be remarkably improved by introducing a group represented by $R^{5a}$ or $R^{5b}$ to an aryl ring or a heteroaryl ring formed by $Z^{1a}$ or $Z^{1b}$.

$R^{22}$ and $R^{23}$ each independently represent a cyano group, an acyl group having 1 to 6 carbon atoms, an alkoxycarbonyl group having 1 to 6 carbon atoms, an alkyl or arylsulfinyl group having 1 to 10 carbon atoms, or a nitrogen-containing heteroaryl group having 3 to 20 carbon atoms, or $R^{22}$ and $R^{23}$ are bonded to each other to form a cyclic acidic nucleus. Specifically, $R^{22}$ and $R^{23}$ have the same definitions as those described in the section of $R^2$ and $R^3$ in the general formula (1) and the preferable ranges thereof are also the same. $R^4$ has the same definition as $R^4$ in the general formula (1) and the preferable range thereof is also the same. $R^4$ may be bonded to $R^{23}$ by a covalent bond or a coordinate bond.

The compound represented by the general formula (2) may further have a substituent and the substituent has the same definition as the substituent T of $R^2$ and $R^3$ and the preferable range is also the same.

As a preferable combination in the general formula (2), $Z^{1a}$ and $Z^{1b}$ each independently form a benzene ring or a pyridine ring; $R^{5a}$ and $R^{5b}$ each independently represent an alkyl group, an alkoxy group, a halogen atom, or a cyano group; $R^{22}$ and $R^{23}$ each independently represent a heterocyclic group, a cyano group, an acyl group, an alkoxycarbonyl group, or a cyclic acidic nucleus formed by $R^{22}$ and $R^{23}$ being bonded to each other; and $R^4$ represents a hydrogen atom, substituted boron, a transition metal atom, magnesium, aluminum, calcium, barium, zinc, or tin. As a particularly preferable combination, $Z^{1a}$ and $Z^{1b}$ form a benzene ring together; both of $R^{5a}$ and $R^{5b}$ represent an alkyl group, a halogen atom, or a cyano group; $R^{22}$ and $R^{23}$ represent a combination of a nitrogen-containing heterocyclic group and a cyano group or an alkoxycarbonyl group which are independent from each other, or a cyclic acidic nucleus formed by $R^{22}$ and $R^{23}$ being bonded to each other; and $R^4$ represents a hydrogen atom, substituted boron, aluminum, zinc, vanadium, iron, copper, paradium, iridium, or platinum.

<Regarding General Formula (3) Above>

In the general formula (3) $R^{31a}$ and $R^{31b}$ each independently represent an alkyl group having 1 to 20 carbon atoms, an aryl group having 6 to 20 carbon atoms, or a heteroaryl group having 3 to 20 carbon atoms. Specifically, $R^{31a}$ and $R^{31b}$ have the same definitions as those described in the section of $R^{1a}$ and $R^{1b}$ in the general formula (1) and the preferable ranges thereof are also the same. $R^{31a}$ and $R^{31b}$ are preferably the same as each other.

$R^{32}$ represents a cyano group, an alkoxycarbonyl group having 1 to 6 carbon atoms, an alkyl or arylsulfinyl group having 1 to 10 carbon atoms, or a nitrogen-containing heteroaryl group having 3 to 10 carbon atoms. Specifically, $R^{32}$ has the same definition as that of $R^2$ in the general formula (1) and the preferable range thereof is also the same.

$R^6$ and $R^7$ each independently represent a hydrogen atom, an alkyl group having 1 to 10 carbon atoms, an aryl group having 6 to 10 carbon atoms, or a heteroaryl group having 4 to 10 carbon atoms. Specifically, $R^6$ and $R^7$ have the same definitions as those of the substituents of $R^2$ and $R^3$ in the general formula (1) and the preferable ranges thereof are also the same. $R^6$ and $R^7$ may be bonded to each other to form a ring, and examples of the ring to be formed include an alicycle having 5 to 10 carbon atoms, an aryl ring having 6 to 10 carbon atoms, or a heteroaryl ring having 3 to 10 carbon atoms, and preferred examples thereof include a benzene ring, a naphthalene ring, and a pyridine ring.

It is possible to realize a near infrared absorbing pigment with both of robustness and invisibility by means of introducing a 5-membered nitrogen-containing heterocycle substituted with $R^6$ and $R^7$ to be used as a boron complex.

$R^8$ and $R^9$ each independently represent an alkyl group having 1 to 10 carbon atom, an alkoxy group having 1 to 10 carbon atoms, an aryl group having 6 to 20 carbon atoms, or a heteroaryl group having 3 to 10 carbon atoms. Specifically, $R^8$ and $R^9$ have the same definitions as those of the substituents of $R^2$ and $R^3$ in the general formula (1) and the preferable ranges thereof are also the same.

X represents an oxygen atom, a sulfur atom, —NR—, —CRR'—, or —CH=CH—. Here, R and R' each independently represent a hydrogen atom, an alkyl group having 1 to 10 carbon atoms, or an aryl group having 6 to 10 carbon atoms and preferably represent a hydrogen atom, an alkyl group having 1 to 6 carbon atoms, or a phenyl group.

As a preferable combination in the general formula (3), $R^{31a}$ and $R^{31b}$ each independently represent an alkyl group having 1 to 10 carbon atoms, a benzene ring, or a pyridine ring; $R^{32}$ represents a cyano group or an alkoxycarbonyl group; $R^6$ and $R^7$ are bonded to each other to form a benzene ring, a pyridine ring, a pyrazine ring, or a pyrimidine ring; $R^8$ and $R^9$ each independently represent an alkyl group having 1 to 6 carbon atoms, a phenyl group, or a naphthyl group; X represents an oxygen atom, a sulfur atom, —NR—, —CRR'—, or —CH=CH—; and R and R' each independently represent a hydrogen atom, an alkyl group having 1 to 6 carbon atoms, or a phenyl group. As a particularly preferable combination, both of $R^{31a}$ and $R^{31b}$ represent an alkyl group having 1 to 10 carbon atoms or a benzene ring; $R^{32}$ represents a cyano group; $R^6$ and $R^7$ are bonded to each other to form a benzene ring or a pyridine ring; $R^8$ and $R^9$ each independently represent an alkyl group having 1 to 6 carbon atoms, a phenyl group, a naphthyl group; and X represents oxygen or sulfur.

<Regarding General Formula (4) Above>

In the general formula (4), $R^{41a}$ and $R^{41b}$ each independently represent an alkyl group having 1 to 20 carbon atoms, an aryl group having 6 to 20 carbon atoms, or a heteroaryl group having 3 to 20 carbon atoms. Specifically, $R^{41a}$ and $R^{41b}$ have the same definitions as those described in the section of $R^{1a}$ and $R^{1b}$ in the general formula (1) and the preferable ranges thereof are also the same. In this case, $R^{41a}$ and $R^{41b}$ represent different groups from each other.

$R^{42}$ represents a cyano group, an alkoxycarbonyl group having 1 to 6 carbon atoms, an alkyl or arylsulfinyl group having 1 to 10 carbon atoms, or a nitrogen-containing heteroaryl group having 3 to 10 carbon atoms. Specifically, $R^{42}$ has the same definition as that of $R^2$ in the general formula (1) and the preferable range thereof is also the same.

$Z^2$ represents an atom group forming a nitrogen-containing hetero 5-membered or 6-membered ring together with —C=N—, and examples of the nitrogen-containing heterocycle include a pyrazole ring, a thiazole ring, an oxazole ring, an imidazole ring, an oxadiazole ring, a thiadiazole ring, a triazole ring, a pyridine ring, a pyridazine ring, a pyrimidine ring, and a pyrazine ring; and a benzo-condensed ring thereof, or a naphtho-condensed ring thereof, or a complex of these condensed rings.

$R^{44}$ represents a hydrogen atom, an alkyl group having 1 to 20 carbon atoms, an aryl group having 6 to 20 carbon atoms, a heteroaryl group having 4 to 20 carbon atoms, a metal atom, or substituted boron including a halogen atom, an alkyl group having 1 to 10 carbon atoms, an aryl group having 6 to 20 carbon atoms, or a heteroaryl group having 4 to 20 carbon atoms as a substituent, and may include a covalent bond or a coordinate bond by being bonded to a nitrogen-containing heterocycle formed by $Z^2$.

It is possible to satisfy the robustness, the invisibility, the dispersibility, and the organic solvent solubility by introducing different groups from each other to $R^{41a}$ and $R^{41b}$ and introducing a nitrogen-containing hetero 5-membered or 6-membered ring formed by $Z^2$ and —C=N—.

As a preferable combination in the general formula (4), $R^{41a}$ and $R^{41b}$ each independently represent an alkyl group having 1 to 10 carbon atoms, a benzene ring, or a pyridine ring; $R^{42}$ represents a cyano group, an alkyl group having 1 to 10 carbon atoms, an arylsulfinyl group, or an alkoxycarbonyl group; $Z^2$ and —C=N— form a thiazole ring, an oxazole ring, an imidazole ring, a thiadiazole ring, a triazole ring, a pyridine ring, a pyrimidine ring, a pyrazine ring, or a benzo-condensed ring thereof, or a naphtho-condensed ring thereof; and $R^{44}$ represents a hydrogen atom, substituted boron, a transition metal atom, magnesium, aluminum, calcium, barium, zinc, or tin. As a particularly preferable combination, $R^{41a}$ and $R^{41b}$ each independently represent an alkyl group having 1 to 10 carbon atoms, or a benzene ring; $R^{42}$ represents a cyano group; $Z^2$ and —C=N— form a thiazole ring, an oxazole ring, an imidazole ring, a triazole ring, a pyridine ring, a pyrimidine ring, or a benzo-condensed ring thereof, or a naphtho-condensed ring thereof; $R^{44}$ represents a hydrogen atom, substituted boron (as the substituent, an alkyl group having 1 to 10 carbon atoms, a benzene ring, a pyridine ring, or a thiophene ring), aluminum, zinc, vanadium, iron, copper, paradium, iridium, or platinum.

Hereinafter, specific examples of the compound represented by the general formula (1) will be described, but the present invention is not limited thereto. In the present specification, Me represents a methyl group, Et represents an ethyl group, Bu represents a butyl group, and Ph represents a phenyl group. Further, in the following chemical formulae, formation of a coordinate bond between a hydrogen atom corresponding to a substituent $R^4$ in the general formula (1) and a nitrogen atom of a heterocycle constituting a substituent $R^3$ is omitted, for example, in the formula D-1 or D-17 (see the scheme 1 in JP-A-2011-68731).

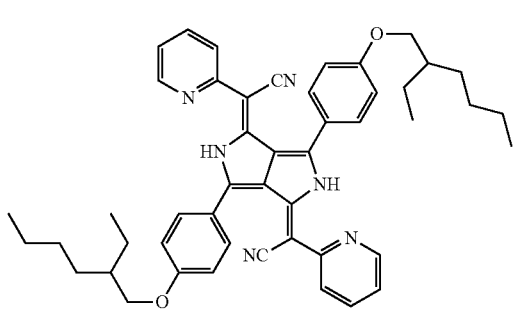

D-1

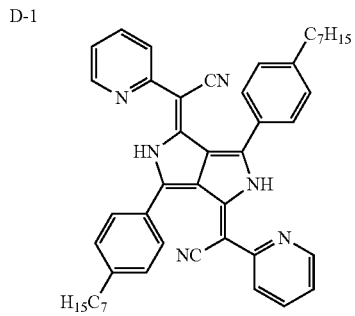

D-2

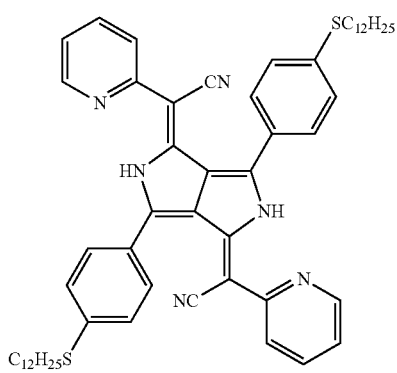

D-3

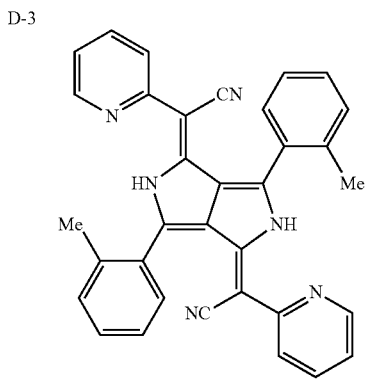

D-4

-continued
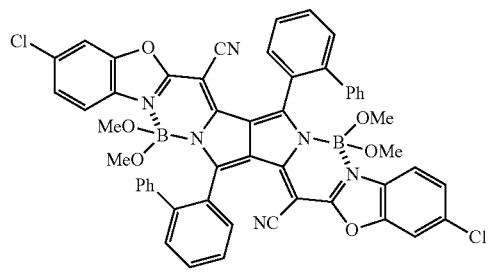
D-5
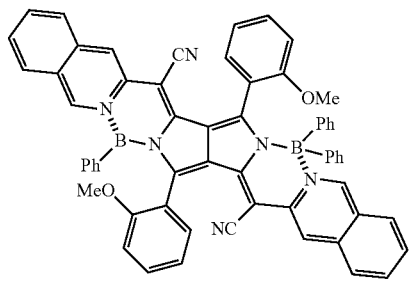
D-6
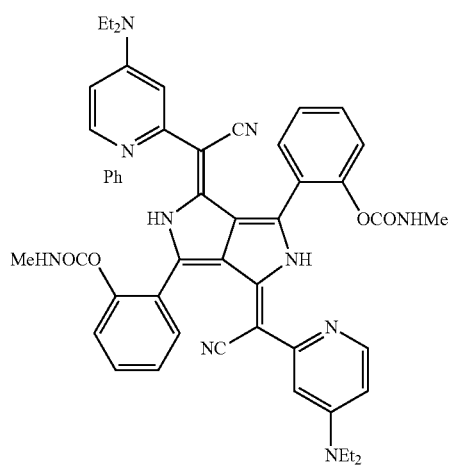
D-7
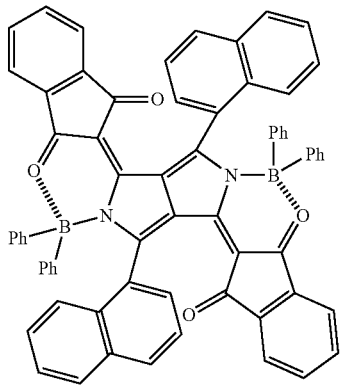
D-8
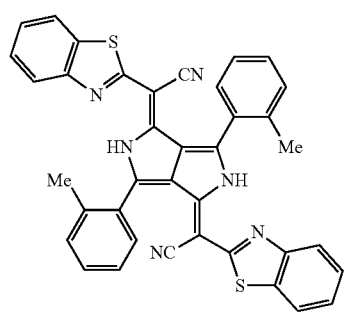
D-9
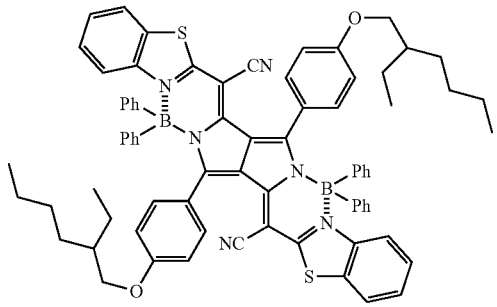
D-10
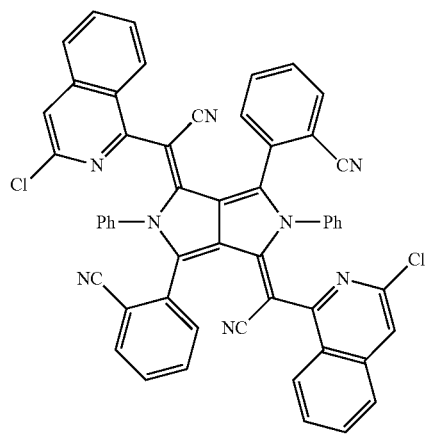
D-11
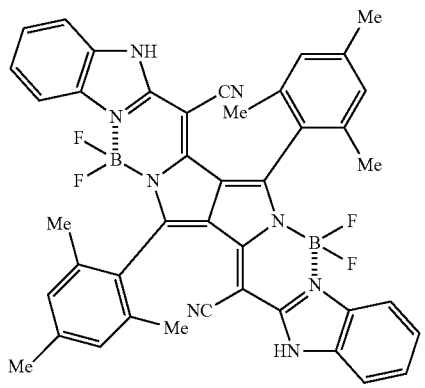
D-12

-continued
D-13
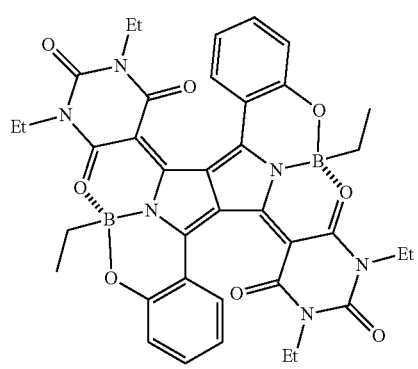
D-14
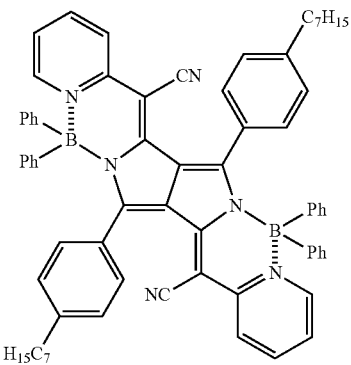
D-15
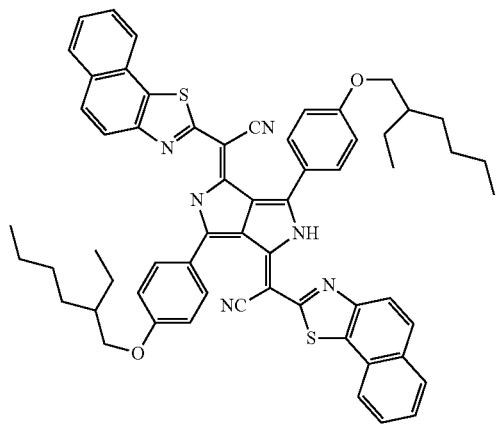
D-16
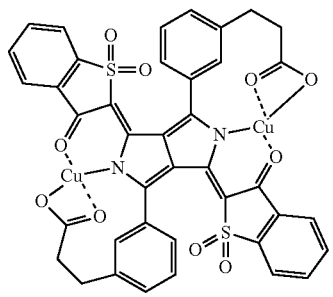
D-17
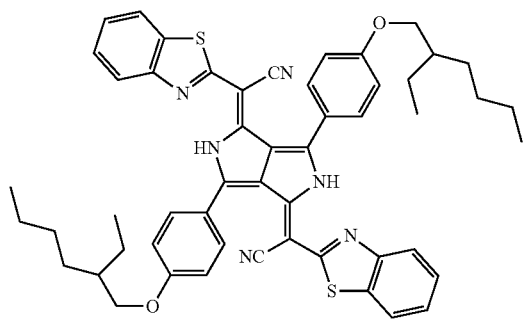
D-18
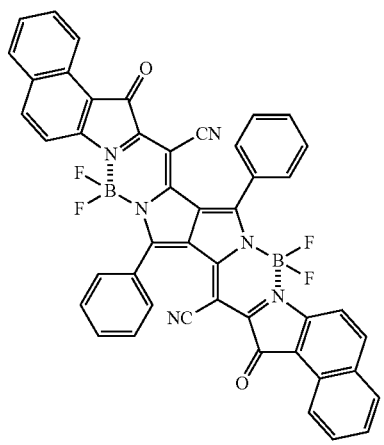
D-19
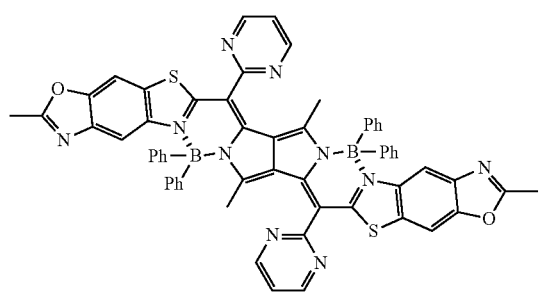
D-20
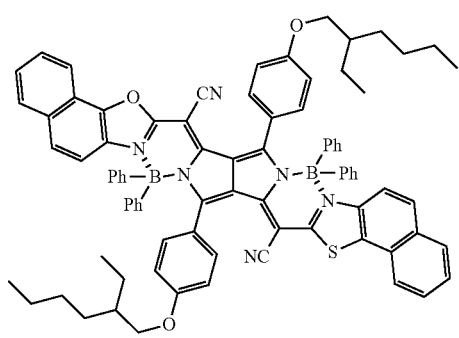

-continued
D-21
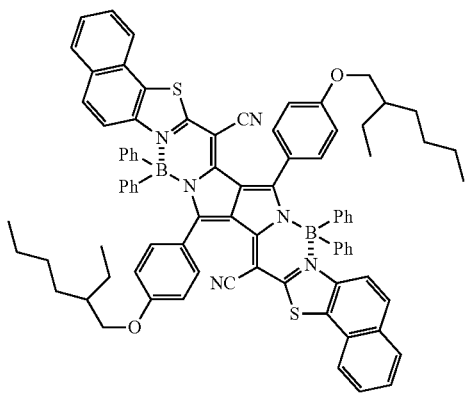
D-22
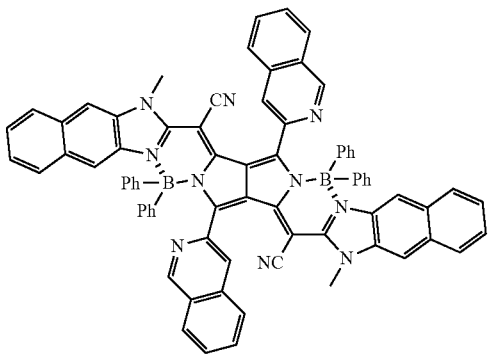
D-23
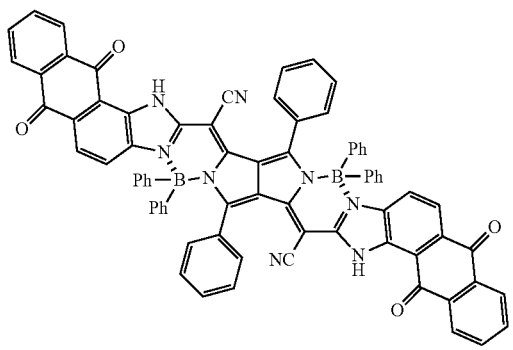
D-24
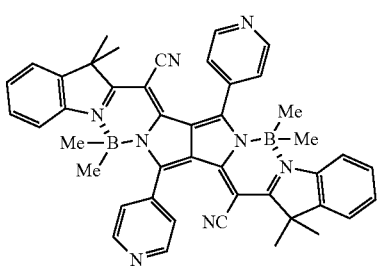
D-25
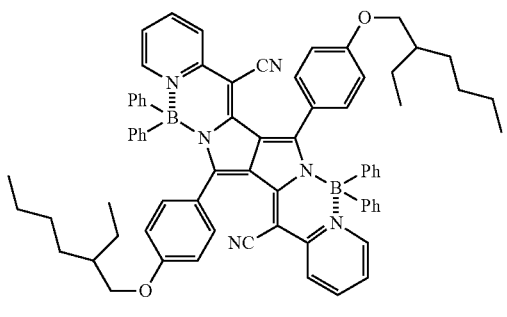
D-26
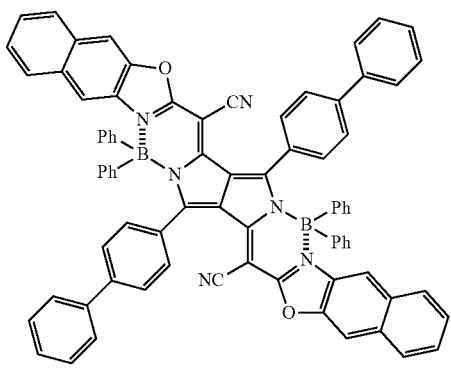
D-27
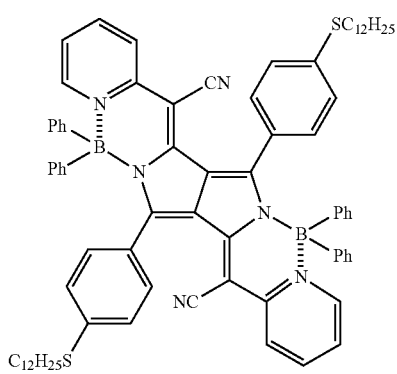
D-28
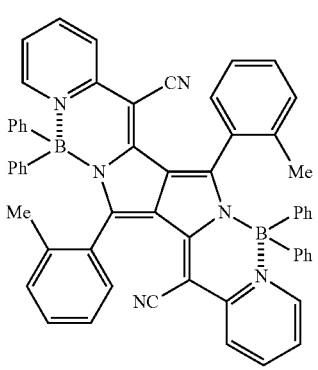

-continued
D-29
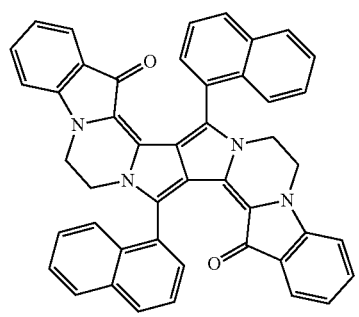
D-30
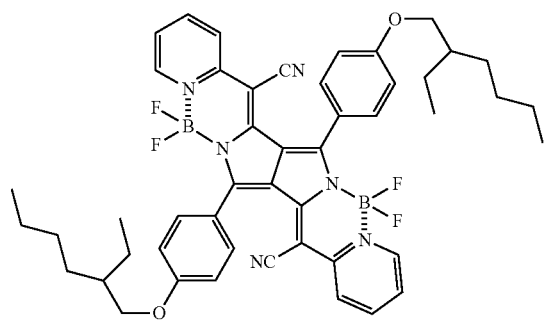
D-31
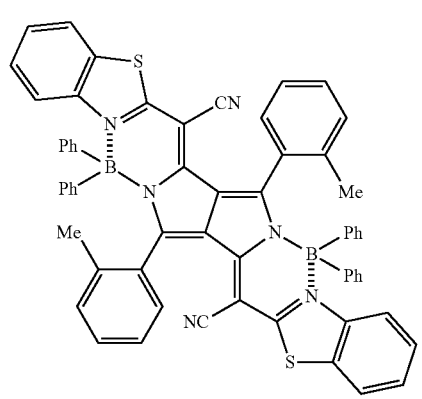
D-32
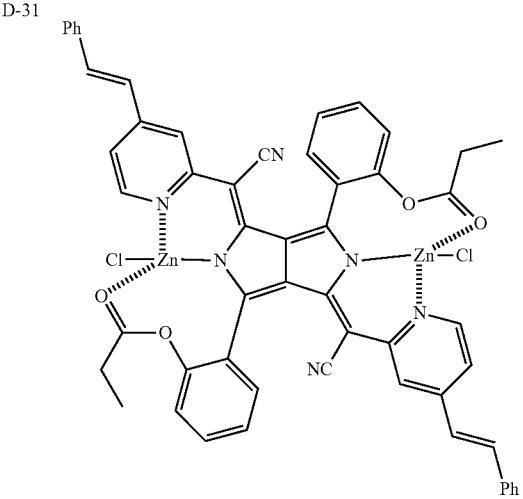
D-33
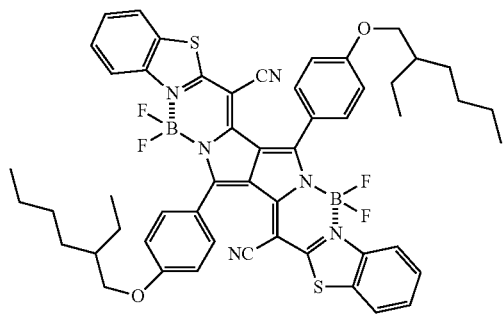
D-34
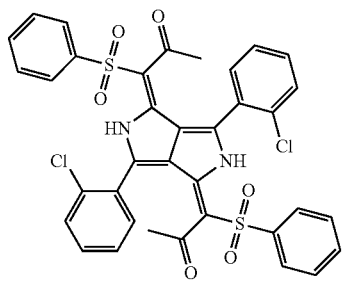
D-35
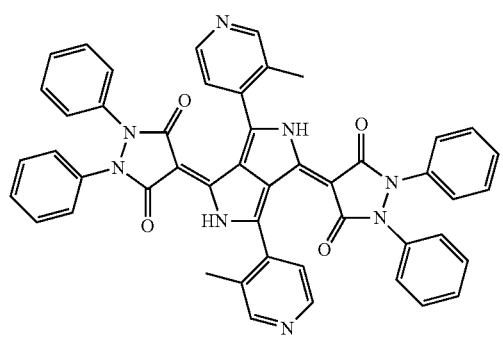
D-36
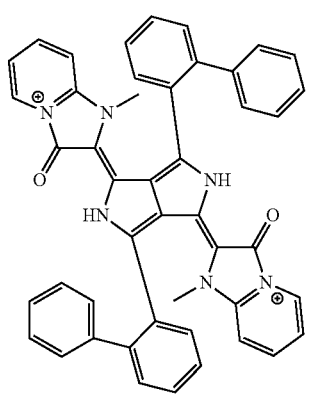

-continued
D-37
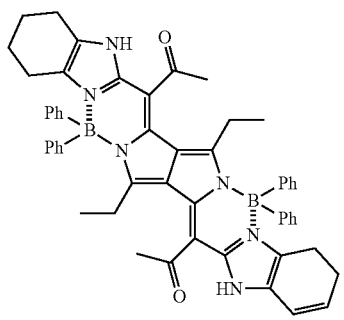
D-38
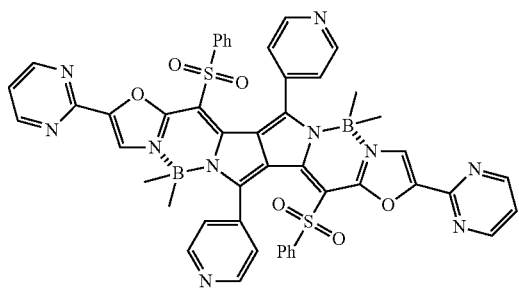
D-39
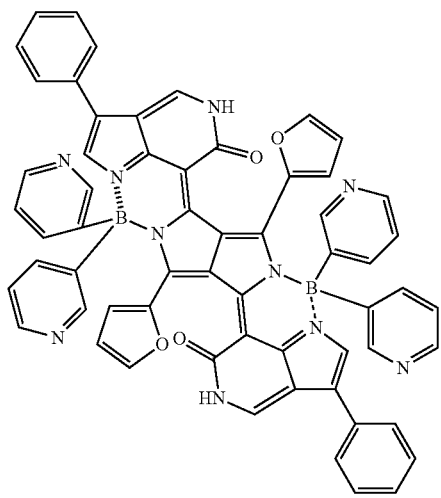
D-40
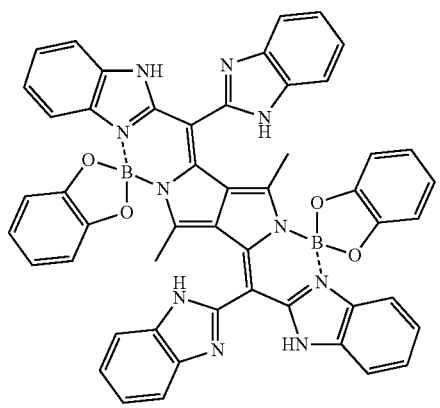
D-41
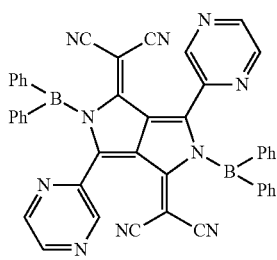
D-42
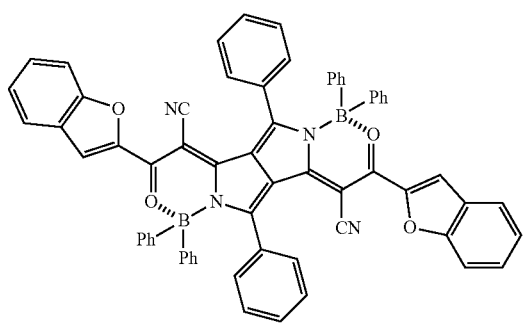
D-43
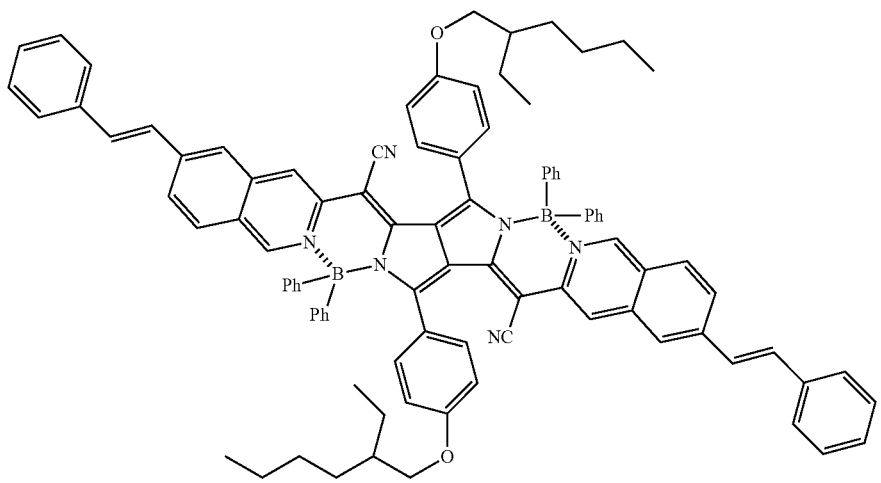

-continued
D-44
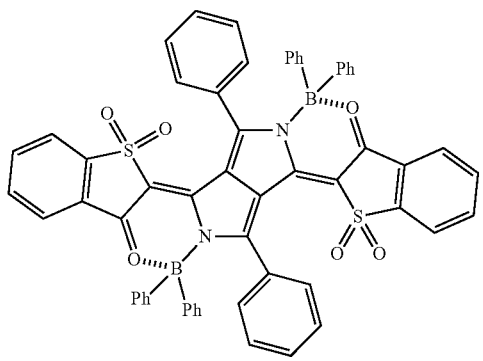
D-45
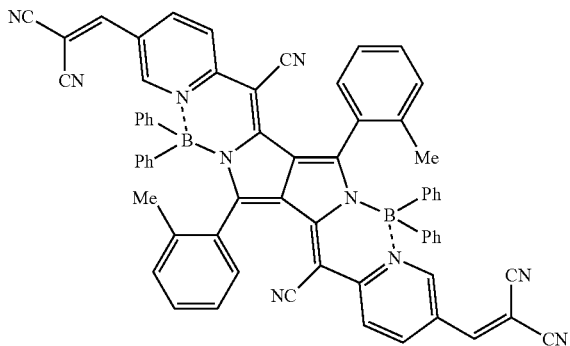
D-46
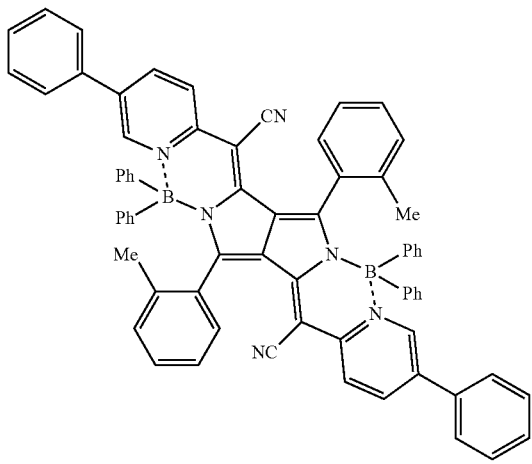
D-47
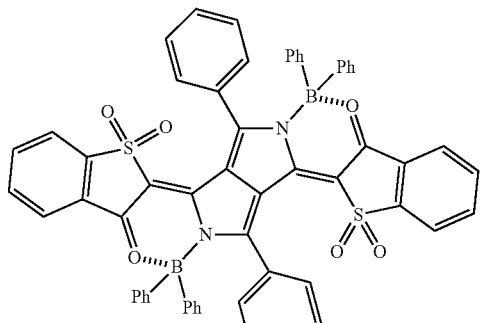
D-101
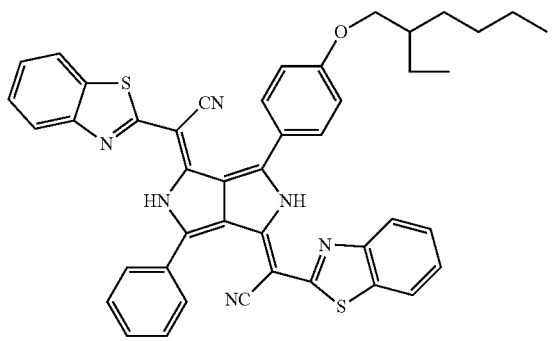
D-102
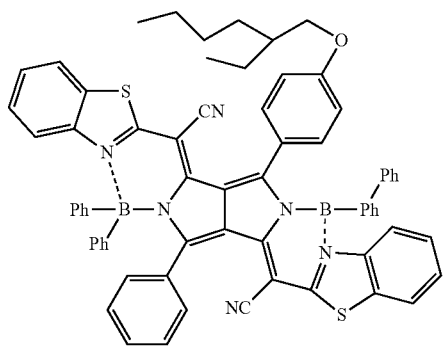
D-103
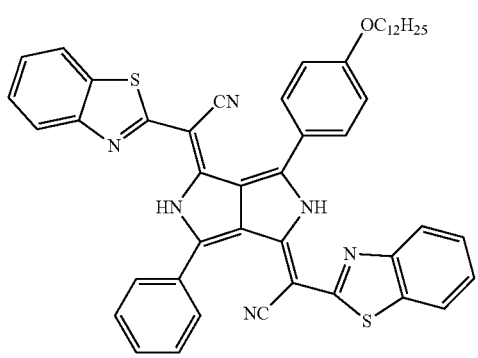
D-104
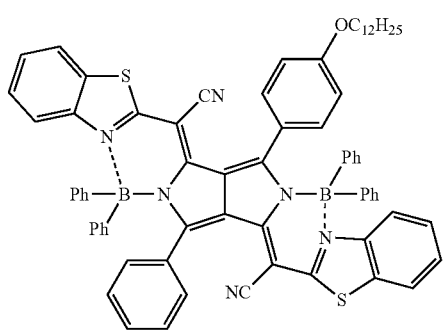

-continued
D-105
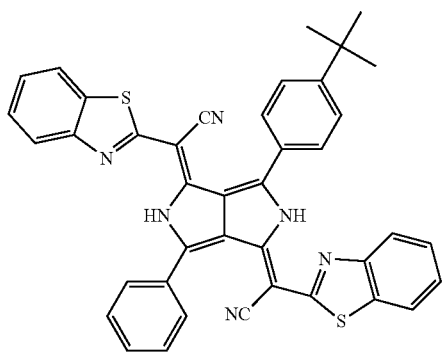
D-106
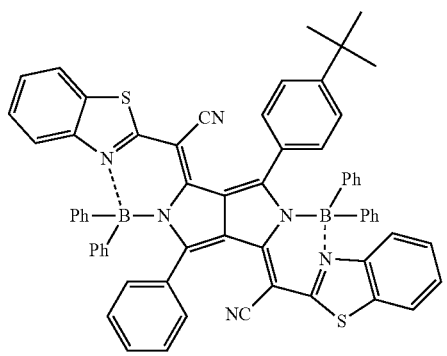
D-107
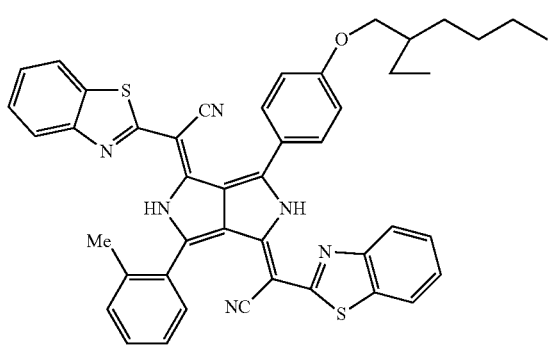
D-108
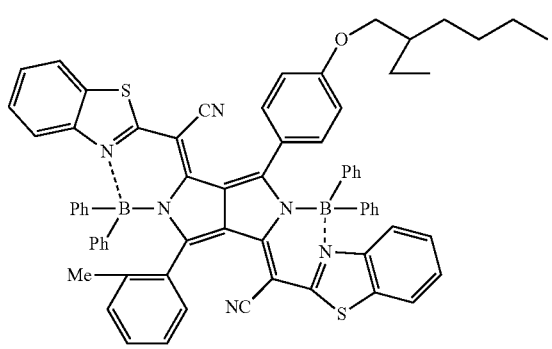
D-109
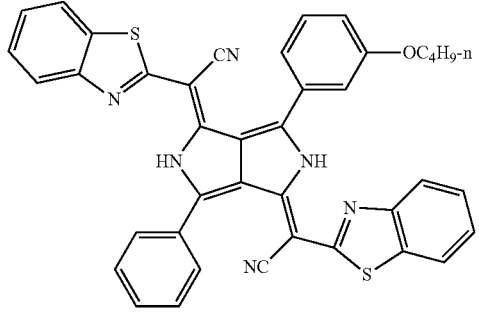
D-110
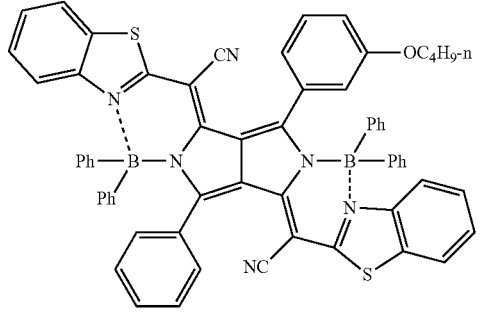
D-111
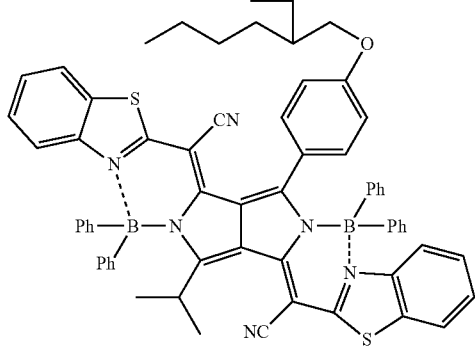
D-112
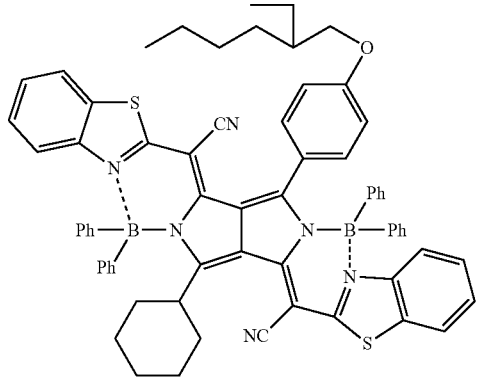

-continued
D-113
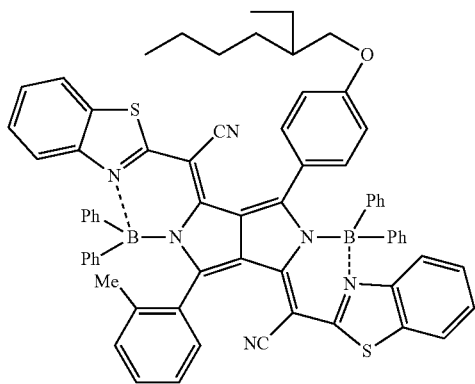
D-114
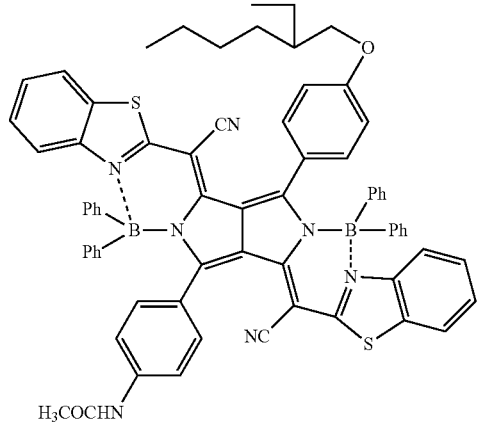
D-115
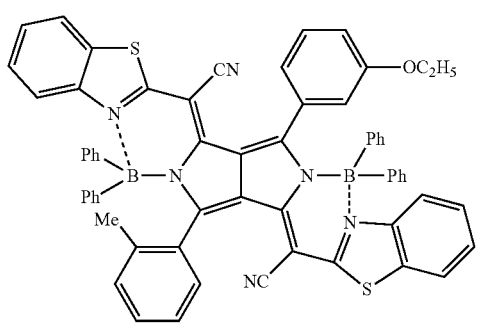
D-116
D-117
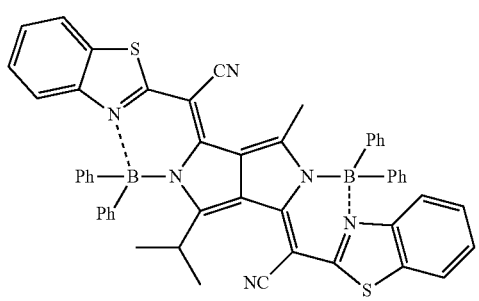
D-118
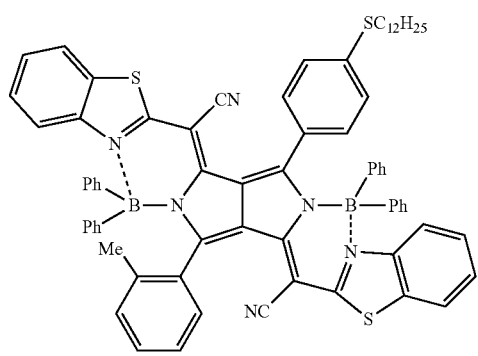
D-119
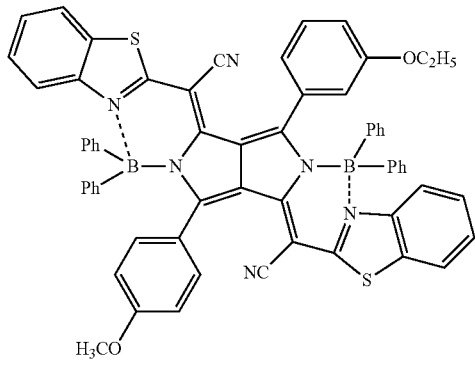
D-120
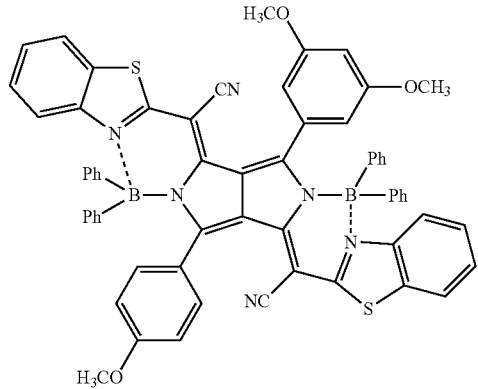

-continued
D-121
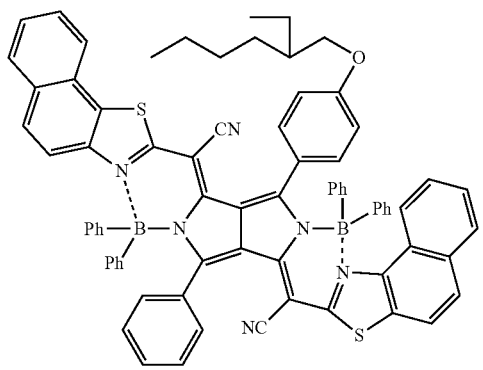
D-122
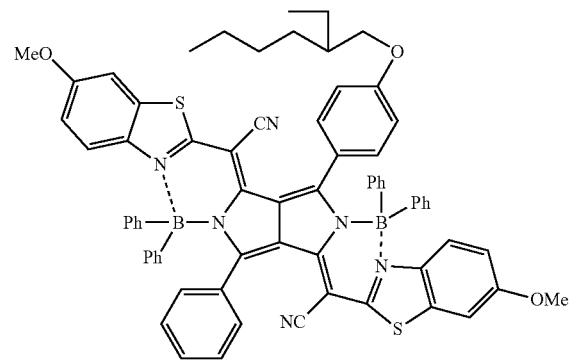
D-123
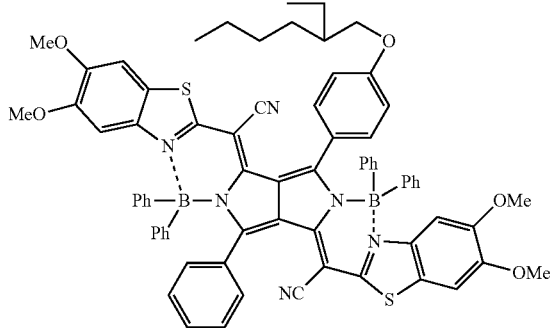
D-124
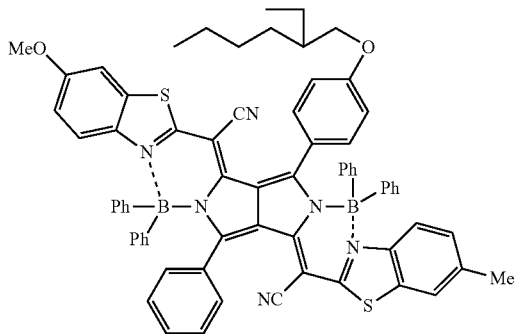
D-125
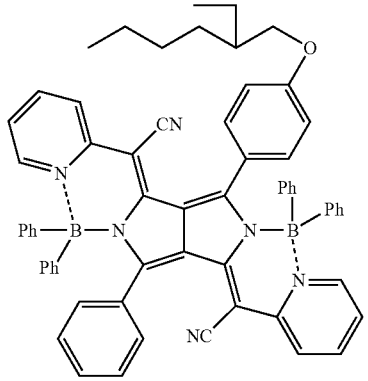
D-126
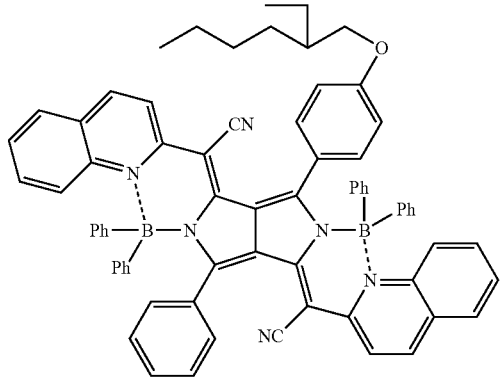
D-127
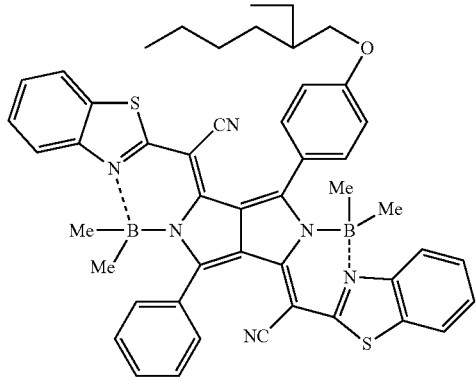
D-128
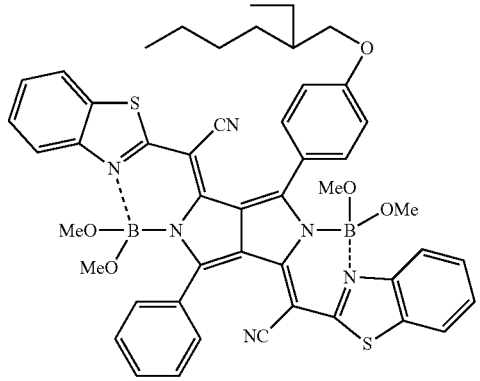

-continued
D-129
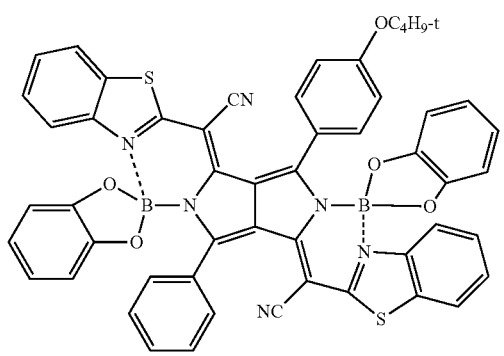
D-130
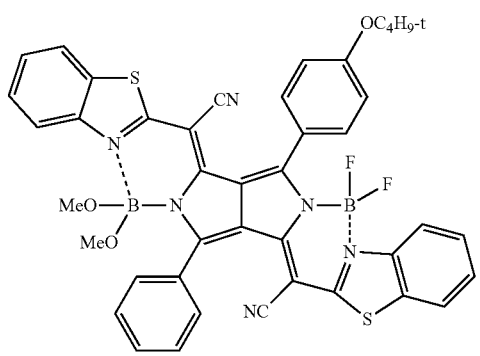
D-131
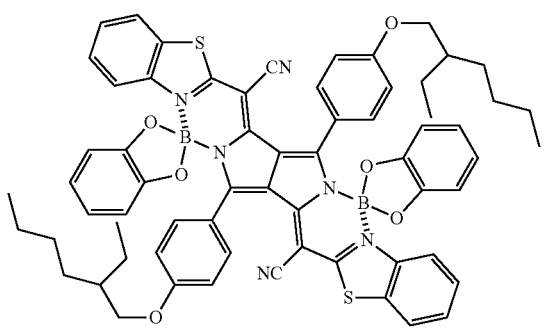
D-132
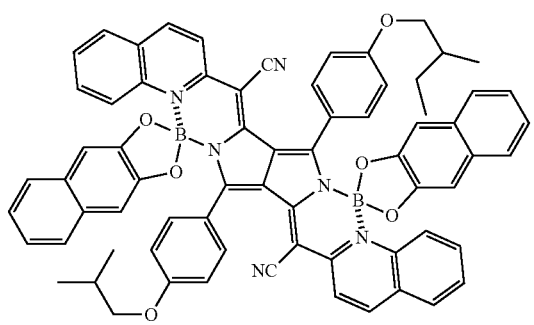
D-133
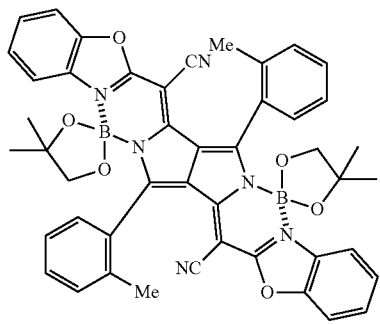
D-134
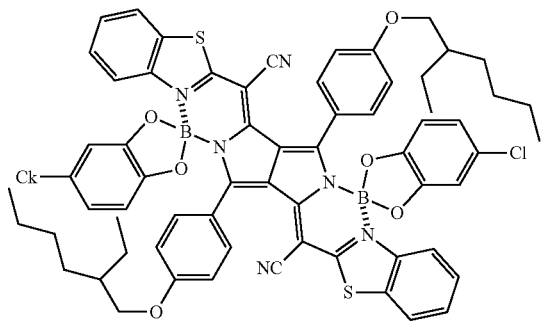

-continued
D-135
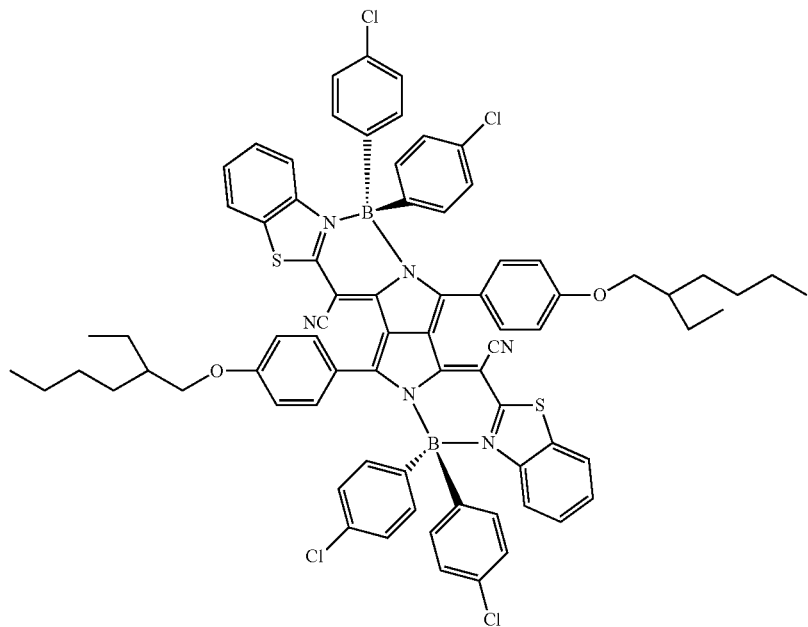
D-136
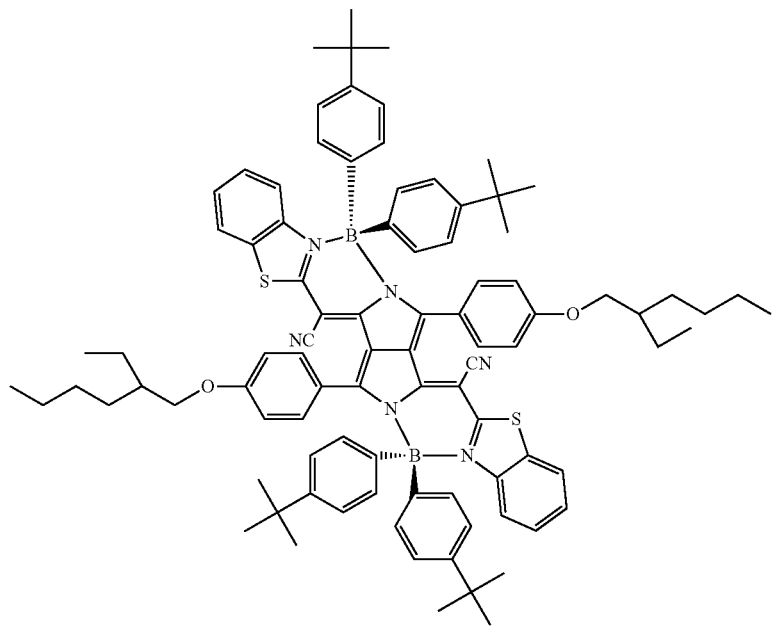
D-137
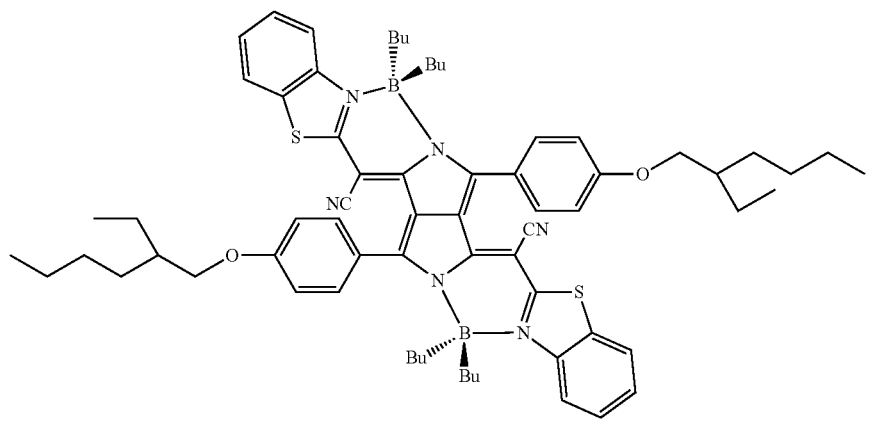

-continued
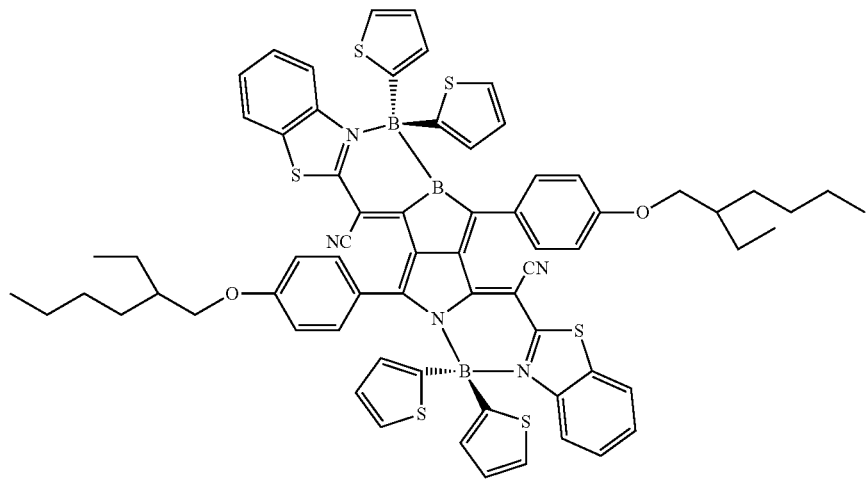
D-138
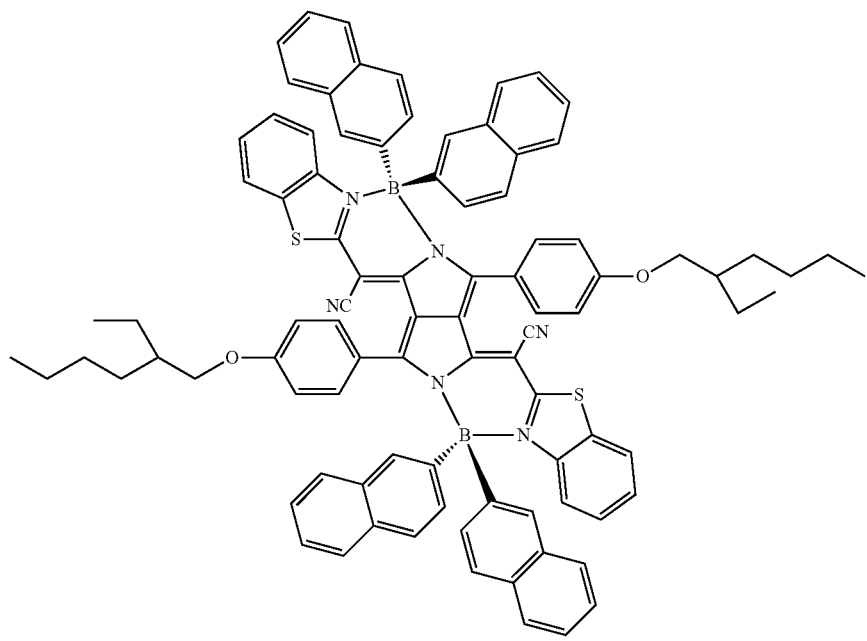
D-139
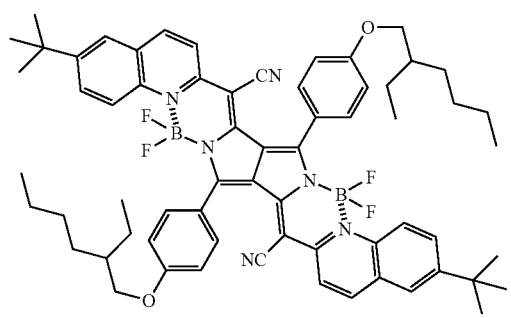
D-140
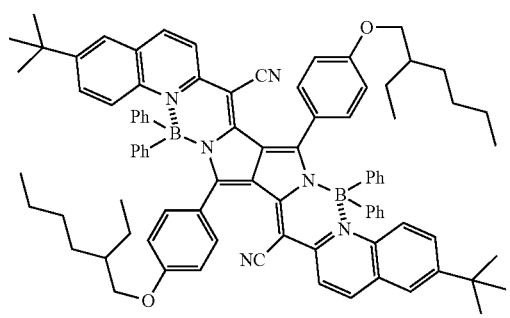
D-141A

-continued
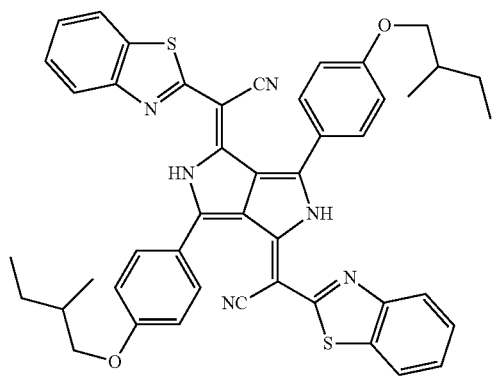
D-141B
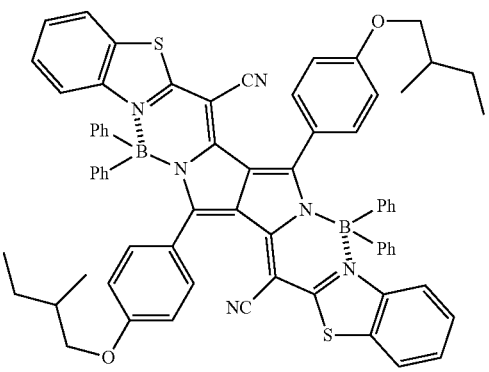
D-142
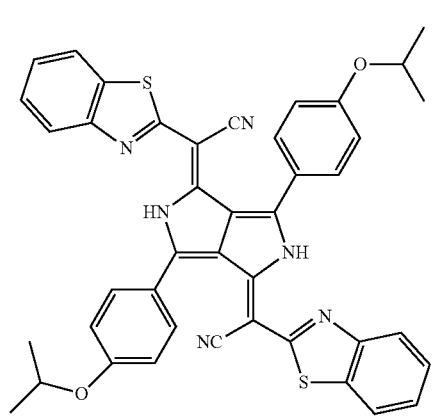
D-143
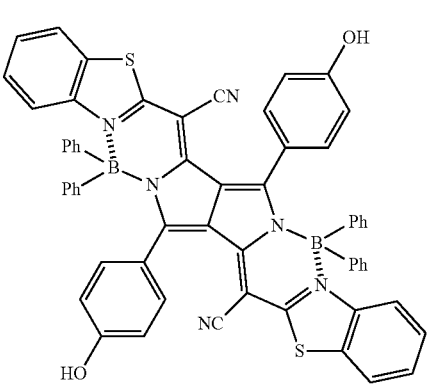
D-144
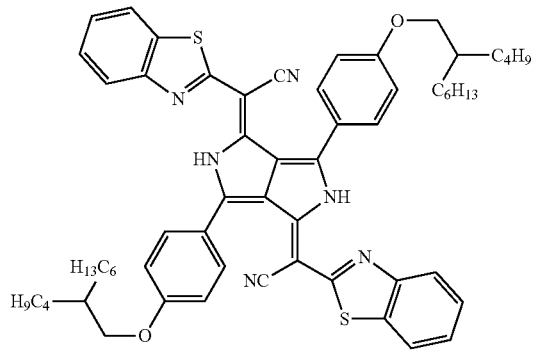
D-145
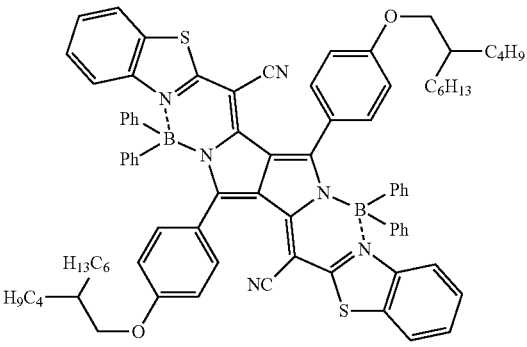
D-146
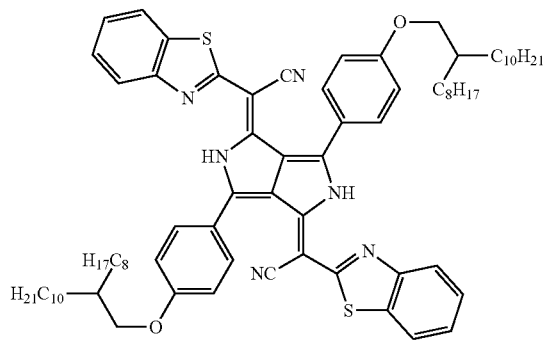
D-147
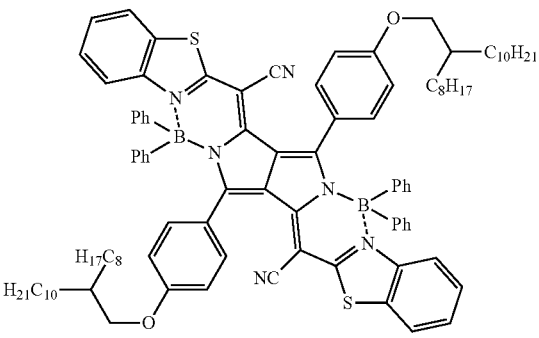
D-148

-continued

D-149

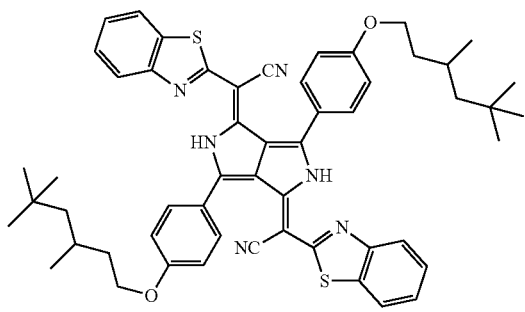

D-150

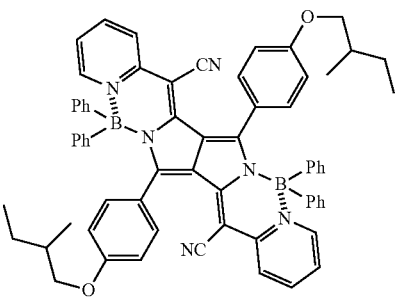

D-151

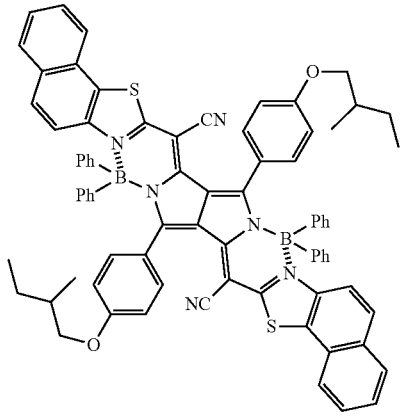

D-152

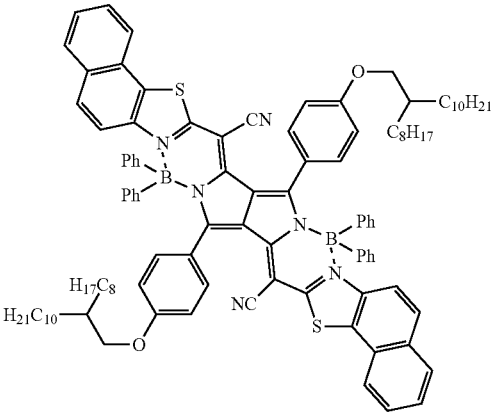

D-153

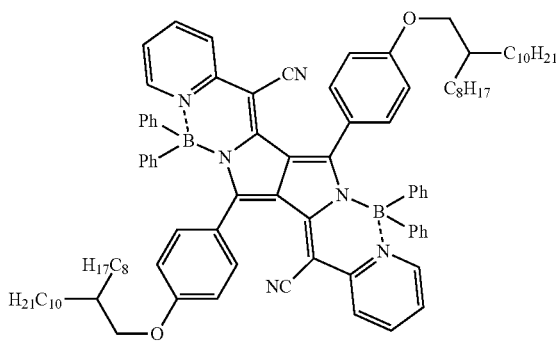

As a synthesis method of the compound represented by the general formula (1), a method described in JP-A-2011-68731 can be exemplified.

The content of the compound represented by the general formula (1) can be adjusted according to the necessity, and the content of the compound in the near infrared ray absorbing layer is preferably in the range of 0.01% by mass to 50% by mass and more preferably in the range of 0.1% by mass to 30% by mass. When the content thereof is in the range, it is possible to impart near infrared absorbing performance and invisibility at the same time.

It is preferable that the compound represented by the general formula (1) is used in a state in which fine particles are dispersed. When the compound is used in the state in which fine particles are dispersed, there are advantages in that the durability of the compound is improved and the maximum absorption wavelength becomes longer.

The number average particle diameter of the compound represented by the general formula (1) is preferably in the range of 5 nm to 500 nm, more preferably in the range of 10 nm to 200 nm, and particularly preferably in the range of 10 nm to 100 nm. When the number average particle size of fine particles is 5 nm or more, the fine particles are unlikely to be aggregated because of a decrease in surface energy of particles, the fine particles become easily dispersed, and the stable dispersion state thereof is easily secured, which is preferable. Further, when the number average particle size of fine particles is 200 nm or less, the influence of particle scattering becomes small, and an absorption spectrum is sharpened, which is preferable.

The fine particle dispersion of the compound represented by the general formula (1) can be produced using methods described in, for example, "*Technology of Dispersing Pigment-Surface Treatment, Method of Using Dispersant, and Evaluation of Dispersibility*-" issued by Technical Information Institute Co., Ltd., "*Encyclopedia of pigments*" issued by Asakura Shoten K. K., and "*Practical Know-how and Case studies of Latest "Pigment Dispersion*"" issued by Technical Information Institute Co., Ltd. An ordinary disperser can be used for preparing fine particle dispersion. As the disperser, a ball mill, a vibrating ball mill, a planetary ball mill, a sand mill, a colloid mill, a jet mill, and a roller mill can be used. The disperser is described in, for example, JP-A-52-92716 and Pamphlet of International Publication No. 88/074794. A vertical or horizontal medium disperser is preferable.

(Dispersant and Dispersion Medium)

It is preferable to add a dispersant for the purpose of improving dispersion stability of fine particle dispersion of the compound represented by the general formula (1). Examples of the dispersant to be used include hydroxyl group-containing carboxylic acid ester, salts of long chain polyaminoamide and high molecular weight acid ester, salts of high molecular weight polycarboxylic acid, salts of long chain polyaminoamide and polar acid ester, high molecular weight unsaturated ester, a high molecular copolymer, modified polyurethane, modified polyacrylate, a polyether ester type anionic surfactant, naphthalenesulfonic acid formalin condensate salts, an aromatic sulfonic acid formalin condensate, a polyoxyethylene alkyl phosphoric acid ester, polyoxyethylene nonylphenyl ether, and stearylamine acetate.

Specific examples of the dispersant are as follows.

Organosiloxane polymers: KP341 (trade name, manufactured by Shin-Etsu Chemical Co., Ltd.)

(Meth)acrylic acid (co)polymers: POLYFLOW No. 75, No. 90, and No. 95 (trade names, manufactured by Kyoeisha Chemical Industry Co., Ltd.)

Cationic surfactants: W001 (trade name, manufactured by Yusho Co., Ltd.)

Nonionic surfactants (polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan fatty acid ester): W004, W005, and W017 (trade names, manufactured by Yusho Co., Ltd.)

Polymer dispersant: EFKA-46, EFKA-47, EFKA-47EA, EFKA polymer 100, EFKA polymer 400, EFKA polymer 401, and EFKA polymer 450 (all trade names, manufactured by Morishita Industry Co., Ltd.); Disperse Aid 6, Disperse Aid 8, Disperse Aid 15, and Disperse Aid 9100 (trade names, manufactured by SAN NOPCO LIMITED)

Others: various SOLSPERSE dispersants such as SOLSPERSE 3000, 5000, 9000, 12000, 13240, 13940, 17000, 24000, 26000, 28000, 32000, 39000, 71000, and 55000 (trade names, manufactured by Lubrizol Corporation); Adeka Pluronic L31, F38, L42, L44, L61, L64, F68, L72, P95, F77, P84, F87, P94, L101, P103, F108, L121, and P123 (trade names, manufactured by ADEKA Corporation); BYK168 (trade name, manufactured by BYK Japan KK.)

The above-described dispersants may be used alone or in combination of two or more kinds thereof.

The fine particle dispersion can be prepared by adding the compound represented by the general formula (1) and a dispersant to a dispersion medium using a disperser. The blending amount of the dispersion medium to be added to the compound represented by the general formula (1) may be an amount which can make the compound represented by the general formula (1) have a desired particle diameter. It is preferable that the dispersant is blended in an amount of approximately 1 part by mass to 300 parts by mass with respect to 100 parts by mass in total of the compound represented by the general formula (1) and the dispersion medium.

The dispersion medium for the compound represented by the general formula (1) is not particularly limited and water or a known organic solvent can be used as the dispersant. Examples thereof include water, toluene, xylene, methyl ethyl ketone, methyl isobutyl ketone, acetone, methyl alcohol, N-propyl alcohol, 1-propyl alcohol, propylene glycol monomethyl ether, propylene glycol monomethyl ether acetate, cyclohexanone, cyclohexanol, ethyl lactate, methyl lactate, and caprolactam. Among these, cyclohexanone is preferable from viewpoints of compatibility with a dispersant and ease of drying a solvent after application.

(Configuration of Near Infrared Absorbing Layer)

In the infrared ray cutting film of the present invention, the film thickness of the near infrared ray absorbing layer, which is not particularly limited, is preferably in the range of 0.1 µm to 5 µm and more preferably in the range of 0.2 µm to 3 µm.

(Method of Forming Near Infrared Ray Absorbing Layer)

The method of forming the near infrared ray absorbing layer is not particularly limited, but the infrared ray cutting film of the present invention is preferably formed by coating. For example, the near infrared ray absorbing layer can be formed by coating with a composition in which the compound represented by the general formula (1) is dispersed in a solution containing a polymerizable monomer or a polymerizable binder resin and drying or curing the layer under a predetermined condition of active energy rays or heat. In the near infrared ray absorbing layer, it is more preferable that fine particles of the compound represented by the general formula (1) are dispersed in a CV curable resin or a thermoplastic resin and particularly preferable that fine particles of the compound represented by the general formula (1) are dispersed in a UV curable resin.

As the thermoplastic resin, which is not particularly limited, a known thermoplastic resin can be used.

As an example of the UV curable resin, which is not particularly limited, a resin formed by being cured by UV rays can be exemplified among polymerizable binder resins and polymerizable monomers described below.

A resin described in JP-A-2011-068731 can be used as the polymerizable binder resin.

The polymerizable monomer is not particularly limited, but it is preferable that one or more kinds selected from a (meth)acrylic monomer, an epoxy monomer, and an oxetanyl monomer are contained in terms of presence of many kinds of variations in substituents and availability.

As the polymerizable monomer, a monomer having two or more polymerizable groups (hereinafter, also referred to as a "bifunctional or higher functional monomer") is preferable. The polymerizable monomer is not particularly limited as long as a polymerization reaction using active energy rays and/or heat is possible, but a monomer having three or more polymerizable groups (hereinafter, also referred to as a "trifunctional or higher functional monomer") is more preferable in terms of strength or solvent resistance of a film.

The kind of the polymerizable group is not particularly limited, but an acryloyloxy group, a methacryloyloxy group, an epoxy group, or an oxetanyl group is particularly preferable as described above.

Specific examples of the polymerizable monomer include an epoxy group-containing monomer described in the paragraphs [0061] to [0065] of JP-A-2001-350012; an acrylate monomer and a methacrylate monomer described in the paragraph [0016] of JP-A-2002-371216; an oxetanyl group-containing monomer described in JP-A-2001-220526, JP-A-2001-310937, the paragraphs [0021] to [0084] of JP-A-2003-341217, and the paragraphs [0022] to [0058] of JP-A-2004-91556; and a monomer described in "*Market Prospects of Reactive Monomer*" published by CMC publishing Co., Ltd.

Examples of the epoxy monomer include a bisphenol A type epoxy resin, a bisphenol F type epoxy resin, a brominated bisphenol A type epoxy resin, a bisphenol S type epoxy resin, a diphenyl ether type epoxy resin, a hydroquinone type epoxy resin, a naphthalene type epoxy resin, a bisphenyl type epoxy resin, a fluorene type epoxy resin, a phenol novolac type epoxy resin, an ortho-cresol novolac type epoxy resin, a trishydroxyphenylmethane type epoxy resin, a trifunctional type epoxy resin, a tetraphenylolethane type epoxy resin, a dicyclopentadiene phenol type epoxy resin, a hydrogenated bisphenol A type epoxy resin, a bisphenol A nucleus-containing polyol type epoxy resin, a polypropylene glycol type epoxy resin, a glycidyl ester type epoxy resin, a glycidylamine type epoxy resin, a glyoxal type epoxy resin, an alicyclic epoxy resin, and a heterocyclic epoxy resin.

Further, examples of the (meth)acrylic monomer include a trifunctional monomer such as trimethylol propane triacrylate, trimethylolpropane PO (propylene oxide)-modified triacrylate, trimethylolpropane EO (ethylene oxide)-modified triacrylate, trimethylolpropane trimethacrylate, or pentaerythritol triacrylate; and a tetrafunctional or higher functional monomer such as pentaerythritol tetracrylate, pentaerythritol tetramethacrylate, dipentaerythritol pentaacrylate, dipentaerythritol pentamethacrylate, dipentaerythritol hexaacrylate, or dipentaerythritol hexamethacrylate.

Further, as an oxetanyl group-containing monomer which is an oxetanyl monomer, a compound described in the paragraphs [0021] to [0084] of JP-A-2003-341217 can be preferably used. In addition, a compound described in the paragraphs [0022] to [0058] of JP-A-2004-91556 can be also used.

<Near Infrared Ray Reflection Layer Obtained by Fixing Cholesteric Liquid Crystal Phase>

The infrared ray cutting film of the present invention includes at least one layer of near infrared ray reflection layer obtained by fixing a cholesteric liquid crystal phase.

The number of laminated layers of near infrared ray reflection layers obtained by fixing the cholesteric liquid crystal phase is not particularly limited and may be in the range of 1 to 10, preferably in the range of 1 to 8, more preferably in the range of 1 to 6. The number is particularly preferably in the range of 2 to 4 from a viewpoint of reducing the number of liquid crystal layers for reflecting infrared light having a wavelength of 1200 nm to 2000 nm and reducing the haze using an infrared ray absorbing layer contained in composite tungsten fine particles, more particularly preferably 2 or 3, and still more particularly preferably 3.

In the infrared ray cutting film of the present invention, it is preferable that the near infrared ray reflection layer includes reflection layers (hereinafter, referred to as a light reflection layer X1 and a light reflection layer X2) obtained by fixing two layers of cholesteric liquid crystal phases which reflect circularly polarized light beams in directions opposite to each other, and whose reflection wavelength region is in the range of 750 nm to 900 nm and in which center reflection wavelengths are equivalent to each other.

The infrared ray cutting film of the present invention may have a configuration in which near infrared ray light reflection layers are laminated on only one surface of the transparent base (also referred to as a substrate) or a configuration in which near infrared ray reflection layers are laminated on both surfaces of the substrate.

In the infrared ray cutting film of the present invention, it is preferable that two sets of infrared ray cutting films having the configuration in which a near infrared ray reflection layer is laminated on only one surface of a substrate are laminated on both surfaces of another substrate and the other substrate is a phase difference plate having a phase difference of a ½ wavelength in this case. Further, in this case, it is more preferable that the former substrate is peeled off from the formed infrared ray cutting film so as to have a structure of lamination of a light reflection layer, a phase difference plate having a phase difference of a ½ wavelength, and a light reflection layer.

The infrared ray cutting film of the present invention may be used by being integrated with another supporting member such as laminated glass. At this time, the substrate may be integrated with another supporting member together with the light reflection layer or the substrate is peeled and the light reflection layer may be integrated with the supporting member.

Among these modes, in the infrared ray cutting film of the present invention, a mode in which the light reflection layer X2 is provided on the light reflection layer X1 side of the substrate through another light reflection layer X3 is preferable, a mode in which the light reflection layer X2 is provided on the light reflection layer X1 side of the substrate through another light reflection layer X3 formed of one layer is more preferable, and a mode in which the substrate, the light reflection layer X1, the light reflection layer X3 formed of one layer, and the light reflection layer X2 are adjacently provided in this order is particularly preferable.

In the infrared ray cutting film of the present invention, the maximum value of reflectance at 750 nm to 1100 nm of at least one layer among the near infrared ray reflection layers is preferably 40% or more and more preferably 45% or more.

Further, the thickness of each near infrared ray reflection layer is in the range of approximately 1 µm to 8 µm (preferably in the range of approximately 3 µm to 7 µm). However, the thickness thereof is not limited to these ranges. It is possible to form a light reflection layer of a desired helical pitch by adjusting the kind and the concentration of materials (mainly, liquid crystal materials and a chiral agent) used for forming the layer. In addition, the thickness of the layer can be set to be in a desired range by adjusting a coating amount.

In the infrared ray cutting film of the present invention, it is preferable that the near infrared ray reflection layer is formed by coating with a cholesteric liquid crystal formed of a polymerizable liquid crystal, and aligning and fixing the cholesteric liquid crystal through photopolymerization.

—Material for Forming Light Reflection Layer—

In the infrared ray cutting film of the present invention, a curable liquid crystal composition is used for forming respective light reflection layers. A preferred example of the liquid crystal composition is a composition containing at least a rod-shaped liquid crystal compound, an optically-active compound (chiral agent), and a polymerization initiator. Two or more kinds of each component may be included. For example, use of a combination of a polymerizable liquid crystal compound and a non-polymerizable liquid crystal compound is possible. In addition, use of a combination of a low molecular liquid crystal compound and a high molecular liquid crystal compound is possible. Further, at least one kind selected from various additives of a horizontal alignment agent, an unevenness preventing agent, a cissing preventing agent, a polymerizable monomer, and the like may be contained for improving uniformity of alignment, suitability of coating, and film strength. In addition, a polymerizable inhibitor, an antioxidant, a UV absorbent, a light stabilizer, a coloring material, a metal oxide fine particle, or the like can be added to the liquid crystal composition in the range of not deteriorating optical performance as needed.

(1) Liquid Crystal Compound

The liquid crystal compound that can be used for the present invention may be a so-called rod-shaped liquid crystal compound or a disk-shaped liquid crystal compound, which is not particularly limited. Among these, a rod-shaped liquid crystal compound is preferably used.

Examples of the rod-shaped liquid crystal compounds which can be used in the prevention include rod-shaped nematic liquid crystal compounds. Examples of the rod-shaped nematic liquid crystal compounds include azomethines, azoxys, cyanobiphenyls, cyanophenyl esters, benzoic acid esters, cyclohexane carboxylic acid phenyl esters, cyanophenyl cyclohexanes, cyano-substituted phenyl pyrimidines, alkoxy-substituted phenyl pyrimidines, phenyl dioxanes, tolanes, and alkenyl cyclohexyl benzonitriles. A high-molecular liquid crystal compound can be used as well as a low-molecular liquid crystal compound.

The rod-shaped liquid crystal compound used in the present invention may be polymerizable or non-polymerizable. The rod-shaped liquid crystal compound free from a polymerizable group is described in various documents (for example, Y. Goto et. al., Mol. Cryst. Liq. Cryst. 1995, vol. 260, p. 23 to 28).

A polymerizable rod-shaped liquid crystal compound can be obtained by introducing a polymerizable group into a rod-shaped liquid crystal compound. Examples of the polymerizable group include an unsaturated polymerizable group, an epoxy group, and an aziridinyl group, and an unsaturated polymerizable group is preferable and an ethylenically unsaturated polymerizable group is particularly preferable. A polymerizable group can be introduced into molecules of a rod-shaped liquid crystal compound using various methods. The number of polymerizable groups included in the polymerizable rod-shaped liquid crystal compound is preferably in the range of 1 to 6 and more preferably in the range of 1 to 3. Examples of the polymerizable rod-shaped liquid crystal compound include compounds described in "*Makromol. Chem.*" vol. 190, p. 2255 (1989), "*Advanced Materials*" vol. 5, p. 107 (1993), U.S. Pat. No. 4,683,327, U.S. Pat. No. 5,622,648, and U.S. Pat. No. 5,770,107, International Publication WO95/22586, WO95/24455, WO97/00600, WO98/23580, and WO98/52905, JP-A-1-272551, JP-A-6-16616, JP-A-7-110469, JP-A-11-80081, and JP-A-2001-328973. Two or more kinds of polymerizable rod-shaped liquid crystal compounds may be used in combination. When two or more kinds of polymerizable rod-shaped liquid crystal compounds may be used in combination, the alignment temperature can be decreased.

(2) Optically-Active Compound (Chiral Agent)

It is preferable that the liquid crystal composition exhibit a cholesteric liquid crystal phase, and for this, the composition preferably contains an optically-active compound. However, when the above-described rod-shaped liquid crystal compound is a molecule having asymmetric carbon atoms, then the mixture could stably form a cholesteric liquid crystal phase even though an optically-active compound is not added thereto. The optically-active compound can be selected from various types of known chiral agents (for example, described in Liquid crystal Device Handbook, Chap. 3, Sec. 4-3, TN, STN Chiral Agents, p. 199, edited by the Japan Society for the Promotion of Science, No. 142 Committee, 1989). The optically-active compound generally contains an asymmetric carbon, but an axial asymmetric compound or a planar asymmetric compound which does not have any asymmetric carbon may also be employable here as a chiral agent. Examples of the axial asymmetric compound or the planar asymmetric compound include binaphthyl, helicene, paracyclophane and their derivatives. The optically-active compound (chiral agent) may have a polymerizable group. In a case where the optically-active compound has a polymerizable group and where the rod-shaped liquid crystal compound to be used here along with the optically-active compound also has a polymerizable group, the polymerization reaction of the polymerizable optically-active compound and the polymerizable rod-shaped compound can form a polymer having a recurring unit derived from the rod-shaped liquid crystal compound and the recurring unit derived from the optically-active compound. In this mode, it is preferable that the polymerizable group which the polymerizable optically-active compound has is the same type of the polymerizable group which the polymerizable rod-shaped liquid crystal compound has. Accordingly, it is preferable that the polymerizable group of the optically-active compound is also an unsaturated polymerizable group, an epoxy group, or an aziridinyl group, more preferably an unsaturated polymerizable group, and particularly preferably an ethylenically unsaturated polymerizable group.

The optically-active compound may be a liquid crystal compound.

Preferably, the amount of the optically-active compound in the liquid crystal composition is 1% by mole to 30% by mole with respect to the liquid crystal compound to be used together. It is preferable that the amount of the optically-active compound to be used is small since the liquid crystallinity of the compound is not affected in many cases. Consequently, the optically-active compound that is used as a chiral agent is preferably one having high torsion strength in order to attain the intended helical pitch torsion alignment even when its amount is small. As the chiral agent having such high torsion strength, for example, chiral agents described in JP-A-2003-287623, and these are favorably used in the present invention.

(3) Polymerization Initiator

Preferably, the liquid crystal composition used for forming the light reflection layer is a polymerizable liquid crystal composition and contains a polymerization initiator for being a polymerizable liquid crystal composition. In the present invention, since the curing reaction is promoted through irradiation with UV light, the polymerization initiator to be used is preferably a photo-polymerization initiator capable of initiating polymerization reaction through irradiation with UV light. Examples of the photo-polymerization initiator include α-carbonyl compounds (described in U.S. Pat. No. 2,367,661 and U.S. Pat. No. 2,367,670), acyloin ethers (described in U.S. Pat. No. 2,448,828), α-hydrocarbon-substituted aromatic acyloin compounds (described in U.S. Pat. No. 2,722,512), polynuclear quinone compounds (described in U.S. Pat. No. 3,046,127 and U.S. Pat. No. 2,951,758), combination of triarylimidazole dimer and p-aminophenylketone (described in U.S. Pat. No. 3,549,367), acridine and phenazine compounds (described in JP-A-60-105667 and U.S. Pat. No. 4,239,850), and oxadiazole compounds (described in U.S. Pat. No. 4,212,970).

The amount of the photo-polymerization initiator to be used is preferably 0.1% by mass to 20% by mass with respect to the liquid crystal composition (solid content in case where the composition is a coating liquid) and more preferably 1% by mass to 8% by mass.

(4) Alignment Control Agent

An alignment control agent contributing to stable or rapid conversion to become a cholesteric liquid crystal phase may be added to the liquid crystal composition. Examples of the alignment control agent include a fluorine-containing (meth) acrylate polymer and compounds represented by the following general formulae (X1) to (X3). Two or more kinds selected from the compounds may be contained. The tilt angle of a molecule of the liquid crystal compound can be reduced or the molecule can be substantially horizontally aligned on the air interface of layers in these compounds. Further, "horizontally aligned" in the present specification means that the long axis of a liquid crystal molecule and the film surface are in parallel with each other, but the long axis and the film surface are not required to be strictly in parallel with each other. In the present specification, "horizontally aligned" means an alignment in which the tilt angle with the horizontal surface is smaller than 20 degrees. In a case where a liquid crystal compound is horizontally aligned in the vicinity of the air interface, since alignment failures are unlikely to occur, transparency in the visible light region becomes high and the reflectance in the infrared region is increased. Meanwhile, when molecules of the liquid crystal compound are aligned at a large tilt angle, since a helical axis of a cholesteric liquid crystal phase is shifted from the normal of the film surface, the reflectance is decreased or a fingerprint pattern is generated and thus the haze is increased or diffraction properties are exhibited, which is not preferable.

Examples of the fluorine-containing (meth)acrylate polymer which can be used as an alignment control agent are described in the paragraphs [0018] to [0043] of JP-A-2007-272185.

Hereinafter, the following general formulae (X1) to (X3) which can be used as an alignment control agent will be sequentially described.

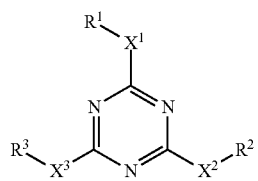
(X1)

In the formula, $R^1$, $R^2$, and $R^3$ each independently represent a hydrogen atom or a substituent; $X^1$, $X^2$, and $X^3$ represent a single bond or a divalent linking group. Preferred examples of the substituent respectively represented by $R^1$ to $R^3$ include substituted or unsubstituted alkyl groups (among these, an unsubstituted alkyl group or a fluorine-substituted alkyl group is more preferable), aryl groups (among these, an aryl group having a fluorine-substituted alkyl group is preferable), a substituted or unsubstituted amino group, an alkoxy group, an alkylthio group, and a halogen atom. The divalent linking group respectively represented by $X^1$, $X^2$, and $X^3$ is preferably a divalent linking group selected from a group consisting of an alkylene group, an alkenylene group, a divalent aromatic group, a divalent heterocyclic residue, —CO—, —NRa— (Ra represents an alkyl group having 1 to 5 carbon atoms or a hydrogen atom), —O—, —S—, —SO—, —SO$^2$—, and a combination of these. The divalent linking group is more preferably a divalent linking group selected from a group consisting of an alkylene group, a phenylene group, —CO—, —NRa—, —O—, —S—, and —SO$_2$— or a divalent linking group obtained by combining at least two groups selected from the group. The number of carbon atoms of the alkylene group is preferably in the range of 1 to 12. The number of carbon atoms of the alkenylene group is preferably in the range of 2 to 12. The number of carbon atoms of the divalent aromatic group is preferably in the range of 6 to 10.

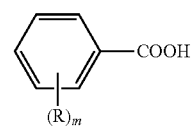
(X2)

In the formula, R represents a substituent and m represents an integer of 0 to 5. When m represents an integer of 2 or more, a plurality of R's may be the same as or different from each other. The substituents preferable as R are the same as those described as the preferable ranges of the substituents represented by $R^1$, $R^2$, and $R^3$. m represents preferably an integer of 1 to 3 and particularly preferably 2 or 3.

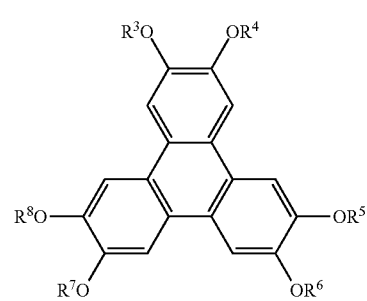
(X3)

In the formula, $R^4$, $R^5$, $R^6$, $R^7$, $R^8$, and $R^9$ each independently represent a hydrogen atom or a substituent. The substituents respectively represented by $R^4$, $R^5$, $R^6$, $R^7$, $R^8$, and $R^9$ are the same as those described as preferable substituents represented by $R^1$, $R^2$, and $R^3$ in the general formula (XI).

Examples of the compounds represented by the formulae (X1) to (X3) which can be used as an alignment control agent in the present invention include compounds described in JP-A-2005-99248.

Further, in the present invention, one kind among the compounds represented by the general formulae (X1) to (X3) may be used alone as an alignment control agent, or two or more kinds thereof may be used in combination.

The amount of the compound represented by any one of general formulae (X1) to (X3) which is to be added to the liquid crystal composition is preferably in the range of 0.01% by mass to 10% by mass, more preferably in the range of 0.01% by mass to 5% by mass, and particularly preferably in the range of 0.02% by mass to 1% by mass with respect to the total mass of the liquid crystal compound.

<Metal Oxide Particles>

Since the infrared ray cutting film of the present invention absorbs long wave infrared rays, the infrared ray cutting film is preferable even when containing at least one kind of metal oxide particle from a viewpoint of balance of heat ray shielding and production cost.

The materials of the metal oxide particles are not particularly limited and can be appropriately selected according to the purpose, and examples thereof include a composite tungsten oxide, tin-doped oxide indium (hereinafter, abbreviated as "ITO"), tin-doped oxide antimony (hereinafter, abbreviated as "ATO"), zinc oxide, titanium oxide, indium oxide, tin oxide, antimony oxide, and glass ceramics. Among these, it is preferable that the metal fine particle dispersion is a composite tungsten oxide represented by the following general formula (I) in terms of excellent heat ray absorbing ability and capability of producing an infrared ray cutting film having heat ray absorbing ability in a broad range by being combined with tabular metal particles.

$$M_xWO_y \quad (I)$$

(M represents at least one element selected from a group consisting of Cs, Na, Rb, K, Tl, In, Ba, Li, Ca, Sr, Fe, and Sn; W represents tungsten; O represents oxygen; and $0.1 \leq x \leq 0.5$ and $2.2 \leq y \leq 3.0$)

Among the composite tungsten oxides represented by the general formula (I), cesium-containing tungsten oxide whose M element is represented by Cs is particularly preferable from a viewpoint of high near infrared ray absorbing ability.

In addition, in the general formula (I), it is preferable that the amount of the M element to be added satisfies the relationship of "$0.001 \leq x/y \leq 1.1$" as a value of x/y based on the content of tungsten and particularly preferable that x/y is around 0.33 in terms of showing preferable near infrared ray absorbing ability. Further, when x/y is around 0.33, a hexagonal crystal structure can be easily set and the durability is improved by setting the crystal structure, which is preferable.

In addition, it is preferable that the content of oxygen in the general formula (I) satisfies the relationship of "$2.2 \leq z/y \leq 3.0$" as a value of z/y based on the content of tungsten. More specifically, $CS_{0.33}WO_3$, $Rb_{0.33}WO_3$, $K_{0.33}WO_3$, $Ba_{0.33}WO_3$, or the like can be exemplified.

The inorganic near infrared ray absorbents may be used alone or in combination of two or more kinds thereof.

In the infrared ray cutting film of the present invention, the average particle diameter of the composite tungsten oxide fine particles is preferably in the range of 5 nm to 500 nm, more preferably in the range of 10 nm to 100 nm, and particularly preferably in the range of 20 nm to 50 nm.

As the composite tungsten oxide fine particles, particles described in JP-A-2009-227938 can be preferably used.

As a method of producing the composite tungsten oxide, which is not particularly limited, any known method can be used. For example, desired oxide fine particles can be obtained by performing hydrolysis in a reaction system containing water using a raw material such as metal salts or metal alkoxide.

Further, in addition to the method of performing hydrolysis in water, inorganic fine particles may be produced in an organic solvent or in an organic solvent in which a thermoplastic resin is dissolved. Examples of the solvent used in these methods include aceton, 2-butanone, dichloromethane, chloroform, toluene, ethyl acetate, cyclohexanone, and anisole. These may be used alone or as a mixture of plural kinds thereof.

As the volume average particle diameter of primary particles of the metal oxide particles, 0.1 μm or less is preferable because the visible light transmittance is not decreased.

The form of the metal oxide particles is not particularly limited and can be appropriately selected according to the purpose, and examples thereof include a spherical form, a needle-like form, and a plate-like form.

The content of the metal oxide particles in the metal oxide particles-containing layer is not particularly limited and can be appropriately selected according to the purpose. For example, the content is preferably from 0.1 g/m² to 20 g/m², more preferably from 0.5 g/m² to 10 g/m², and even more preferably from 1.0 g/m² to 4.0 g/m².

The amount of sunlight which could be felt on skin may increase when the content is less than 0.1 g/m² and the visible light transmittance may deteriorate when the content thereof is more than 20 g/m². Meanwhile, when the content is in the range of 1.0 g/m² to 4.0 g/m², it is advantageous since the above two problems are avoidable.

Moreover, the content of the metal oxide particles in the metal oxide particles-containing layer can be calculated, for example, by measuring the number of the metal oxide particles in a constant area and the average particle diameter thereof through observation of the TEM image of an ultra-thin section of the heat ray shielding layer and the SEM image of the surface thereof and dividing the mass (g) calculated based on the number and the average particle diameter thereof and the specific gravity of the metal oxide particles by the constant area (m²). Alternatively, the content of the metal oxide particles in the metal oxide particles-containing layer can be calculated by eluting the metal oxide fine particles in a constant area of the metal oxide particles-containing layer in methanol, and by dividing the mass (g) of the metal oxide fine particles measured through fluorescent X-ray measurement by the constant area (m²).

<Diimmonium Pigment>

It is preferable that the infrared ray cutting film of the present invention further contains a diimmonium pigment. The diimmonium pigment can absorb near infrared rays on the long wavelength side in the absorption wavelength band of 800 nm to 1100 nm. As the diimmonium pigment, pigments described in JP-A-2005-054031 or the like can be preferably used.

A layer to which the diimmonium pigment is added is not particularly limited, but an easily-adhesive layer described below can be preferably added.

<Other Layers and Components>

It is preferable that the infrared ray cutting film of the present invention further includes at least one among an easily-adhesive layer, a hard coat layer, a UV absorbing layer, an adhesive layer, and a surface protective layer.

—Easily-Adhesive Layer—

The infrared ray cutting film of the present invention may have an easily-adhesive layer as the outermost layer of one side or both sides thereof. The easily-adhesive layer has a function of improving the adhesion property with the interlayer film for laminated glass. More specifically, the easily-adhesive layer has a function of improving adhesion with the light reflection layer of the cholesteric liquid crystal phase and/or the substrate, and the interlayer film for laminated glass. As materials that can be used for forming the easily-adhesive layer, polyvinyl butyral (PVB) resin is exemplified. The polyvinyl butyral resin is a type of polyvinyl acetal that is formed through reaction of polyvinyl alcohol (PVA) and butylaldehyde in the presence of an acid catalyst, and has a recurring unit having the following structure.

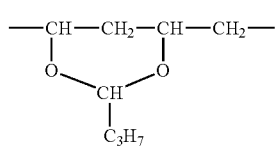

It is preferable that the easily-adhesive layer is formed through coating. For example, the easily-adhesive layer may be formed through coating on the surface of the light reflection layer of the cholesteric liquid crystal phase and/or the rear surface of the substrate (surface on the side in which the light reflection layer is not formed). More specifically, one kind of the polyvinyl butyral resin is dissolved in an organic solvent to prepare a coating liquid, and the surface of the light reflection layer of the cholesteric liquid crystal phase and/or the rear surface of the substrate is coated with the coating liquid to be heated and dried as needed, and then an easily-adhesive layer can be formed. As the solvent used for preparation of the coating liquid, for example, methoxy propyl acetate (PGMEA), methyl ethyl ketone (MEK), isopropanol (IPA), or the like can be used. As the coating method, various known methods in the related art can be used. A preferred range of the temperature at the time of drying varies by materials used for preparation of the coating liquid, but the temperature thereof is preferably 140° C. to 160° C. in general. The drying time is not particularly limited, but the time thereof is generally 5 minutes to 10 minutes.

The easily-adhesive layer may also be a so-called undercoat layer that includes an acrylic resin, a styrene/acrylic resin, a urethane resin, and a polyester resin. The easily-adhesive layer formed of these materials can be formed by coating. In addition, some commercially-available polymer films may have an undercoat layer formed therein, and such commercial products can be used as the substrate.

The thickness of the easily-adhesive layer is preferably 0.1 μm to 2.0 μm.

—Undercoat Layer—

The infrared ray cutting film of the present invention may have an undercoat layer between the light reflection layer of the cholesteric liquid crystal phase and the substrate. When the adhesion power between the light reflection layer of the cholesteric liquid crystal phase and the substrate is weak, peeling failure is likely to occur in the process of laminating and producing the light reflection layer of the cholesteric liquid crystal phase or the strength (impact resistance) in a case of using laminated glass as the infrared ray cutting film is reduced. Accordingly, as the undercoat layer, a layer capable of improving adhesion between the cholesteric liquid crystal layer and the substrate can be used. On the other hand, in a case where the substrate or the substrate and the undercoat layer are peeled off, and a member such as an interlayer film sheet or the like is integrated with the light reflection layer, an adhesion whose degree is not so strong that the layer is peelable is required at the interface between the substrate and the undercoat layer or the undercoat layer and the light reflection layer of the cholesteric liquid crystal phase. In consideration of being used as the laminated interlayer film sheet in the subsequent process, it is preferable to be peelable at the interface between the undercoat layer and the substrate.

Examples of the material usable in forming the undercoat layer include an acrylic acid ester copolymer, polyvinylidene chloride, styrene-butadiene rubber (SBR), and aqueous polyester. In an embodiment where the surface of the undercoat layer is adhered to an interlayer film, it is preferable that the adhesion between the undercoat layer and the interlayer film be excellent; and from the viewpoint, it is preferable that the undercoat layer contain a polyvinyl butyral resin in addition to the above-described materials. In addition, since the adhesion power of the undercoat layer is necessary to be appropriately adjusted as described above, it is preferable that the layer is cured with a suitable curing agent, for example, with dialdehydes such as glutaraldehyde, 2,3-dihydroxy-1,4-dioxane, or the like, or with boric acid or the like. The amount of the curing agent to be added is preferably 0.2% by mass to 3.0% by mass with respect to the dry mass of the undercoat layer.

Preferably, the thickness of the undercoat layer is 0.05 μm to 0.5 μm.

—Alignment Layer—

The infrared ray cutting film of the present invention may include an alignment layer between the light reflection layer of the cholesteric liquid crystal phase and the substrate. The alignment layer has a function of more precisely defining the alignment direction of the liquid crystal compound in the cholesteric liquid crystal layer. The alignment layer can be provided by means of a rubbing treatment of an organic compound (preferably, a polymer), oblique vapor deposition of an inorganic compound, and a formation of a layer with microgrooves. Further, an alignment layer in which an alignment function is generated due to application of an electric field, application of a magnetic field, or photo-irradiation is known. The alignment layer is preferably formed on the surface of a film of a polymer by a rubbing treatment.

Since the alignment layer is necessary to be in close contact with the light reflection layer of the cholesteric liquid crystal phase, it is preferable that the alignment layer is provided between the light reflection layer of the cholesteric liquid crystal phase and the substrate or the undercoat layer. However, the undercoat layer may have a function of the alignment layer. In addition, the alignment layer may be included between the light reflection layers.

It is preferable that the alignment layer has a certain degree of adhesion power with respect to all of the light reflection layers of the adjacent cholesteric liquid crystal phase, undercoat layer, and substrate. However, in a case where an infrared ray cutting film is prepared by being laminated with a phase difference plate having a phase difference of a ½ wavelength or a laminated interlayer film sheet is prepared while the substrate is peeled off from the light reflection layer of the cholesteric liquid crystal phase, which is an example of the embodiment of the present invention described below, the adhesion whose degree is not so strong that the layer is peelable is required at any of the interfaces of the light reflection layer of the cholesteric liquid crystal phase/the alignment layer/the undercoat layer/the substrate. The interface in which peeling is carried out can be any of the interfaces, but it is preferable that peeling is carried out at the interface between the alignment layer and the undercoat layer in consideration of being used as the laminated interlayer film sheet in the subsequent process.

As a material used for the alignment layer, a polymer of an organic compound is preferable, and a polymer which can be crosslinked by itself or a polymer which is crosslinked using a crosslinking agent is frequently used. Certainly, a polymer having both functions is used. Examples of the polymer include a polymer such as a polymethyl methacrylate, an acrylic acid/methacrylic acid copolymer, a styrene/malein imide copolymer, polyvinyl alcohol, modified-polyvinyl alcohol, poly(N-methylol acrylamide), a styrene/vinyl toluene copolymer, chlorosulfonated polyethylene, nitrocellulose, polyvinyl chloride, chlorinated polyolefin, polyester, polyimide, a vinyl acetate/vinyl chloride copolymer, an ethylene/vinyl acetate copolymer, carboxymethyl cellulose, gelatin, polyethylene, polypropylene, and polycarbonate, and a compound such as a silane coupling agent, etc. Examples of preferred polymers include water-soluble polymers such as poly(N-methylol acrylamide), carboxymethyl cellulose, gelatin, polyvinyl alcohol, and modified-polyvinyl alcohol, more preferred examples thereof include gelatin, polyvinyl alcohol, and modified-polyvinyl alcohol, and particularly preferred examples thereof include polyvinyl alcohol and modified polyvinyl alcohol. In addition, in an embodiment of adhering the interlayer film to the surface of the alignment layer, it is preferable that the adhesion between the alignment layer and the interlayer film is good. From this viewpoint, it is preferable that the alignment layer contain a polyvinyl butyral resin in addition to the above-described materials.

The thickness of the alignment layer is preferably 0.1 µm to 2.0 µm.

—Hard Coat Layer—

For imparting scratch resistance, preferably, a hard coat layer having hard coating properties is included. The hard coat layer may contain metal oxide particles.

The hard coat layer is not particularly limited and the kind or the formation method thereof can be appropriately selected according to the purpose. Examples thereof include thermosetting or photosetting resins such as acrylic resin, a silicone resin, a melamine resin, a urethane resin, an alkyd resin, and a fluororesin. The thickness of the hard coat layer is not particularly limited and can be appropriately selected according to the purpose. Preferably, the thickness thereof is in the range of 1 µm to 50 µm. It is preferable that an anti-reflection layer and/or an antiglare layer is further formed on the hard coat layer, since a functional film having anti-reflection properties and/or antiglare properties in addition to scratch resistance can be obtained. The hard coat layer may contain the above-described metal oxide particles.

—UV Absorbent—

It is preferable that the infrared ray cutting film of the present invention includes a layer containing a UV absorbent.

The layer containing a UV absorbent can be appropriately selected according to the purpose. However, depending on the kinds of the UV absorbents, since alignment of the liquid crystal is influenced, it is preferable to be added to a member (a layer or a substrate) other than the light reflection layer. According to the embodiment of the present invention, various modes may be adopted, but it is preferable to be added to a member to which light is incident before the light reflection layer. For example, it is preferable to be added to a layer arranged between a glass plate arranged on the outdoor side and the light reflection layer of the cholesteric liquid crystal phase. Alternatively, it is also preferable to be contained in the interlayer film to be adhered to the glass plate arranged on the outdoor side or the glass plate itself arranged on the outdoor side.

Examples of compounds that can be used as the UV absorbent include benzotriazole-based, benzodithiol-based, coumarin-based, benzophenone-based, salicylic acid ester-based, and cyanoacrylate-based UV absorbents; titanium oxide, and zinc oxide. Particularly preferred examples of the UV absorbent include Tinuvin 326, 328, and 479 (all manufactured by Ciba Japan KK). Further, the kind and the blending amount of the UV absorbent are not particularly limited, and can be appropriately selected according to purposes. Particularly, when a member containing the UV absorbent has an effect of adjusting the transmittance of UV light having a wavelength of 380 nm or less to be 0.1% or less, deterioration of the light reflection layer can be remarkably suppressed and yellowing due to UV light can be remarkably suppressed, which are preferable. Accordingly, it is preferable to determine the kind and the blending amount of the UV absorbent so as to satisfy the above-described characteristics.

—Adhesive Layer—

It is preferable that the infrared ray cutting film of the present invention includes an adhesive layer (hereinafter, referred to as an adhesive layer). The adhesive layer may include a UV absorbent.

The materials which can be used for forming the adhesive layer are not particularly limited and can be appropriately selected according to the purpose, and examples thereof include a polyvinyl butyral (PVB) resin, an acrylic resin, a styrene/acrylic resin, a urethane resin, a polyester resin, and a silicone resin. These can be used alone or in combination of two or more kinds thereof. The adhesive layer made of these materials can be formed by coating.

In addition, an antistatic agent, a lubricant, and an antiblocking agent may be added to the adhesive layer.

The thickness of the adhesive layer is preferably in the range of 0.1 µm to 10 µm.

<Method of Producing Infrared Ray Cutting Film>

The method of producing the infrared ray cutting film of the present invention is not particularly limited and can be appropriately selected according to the purpose, and examples thereof include a method of coating the surface of the underlying layer of the support with a coating liquid for a near infrared ray reflection layer or a near infrared ray absorbing layer using a dip coater, a die coater, a slit coater, a bar coater, a gravure coater or the like; and a method of performing surface alignment using an LB film method, a self-assembly method, or a spray coating method. Among these, a coating method using a bar coater is preferable.

In a case where the near infrared ray reflection layer or the near infrared ray absorbing layer is formed by coating, other additives such as a solvent and a surfactant may be added to the coating liquid in addition to the pigment or the polymer.

As the solvent, which is not particularly limited, water or a known organic solvent can be used, and examples thereof include water, toluene, xylene, methyl ethyl ketone, methyl isobutyl ketone, acetone, methyl alcohol, N-propyl alcohol, 1-propyl alcohol, propylene glycol monomethyl ether, propylene glycol monomethyl ether acetate, cyclohexanone, cyclohexanol, ethyl lactate, methyl lactate, and caprolactam. In the present invention, an aqueous solvent is preferably used in terms of environmental impact and reduction in coating cost.

The solvents may be used alone or in combination of two or more kinds thereof.

In the case where the near infrared ray reflection layer or the near infrared ray absorbing layer is formed by coating, it is preferable that the near infrared ray reflection layer or the near infrared ray absorbing layer is formed by applying the coating liquid, drying with a known method, and solidifying the layer. As the drying method, drying the layer by heating is preferable.

An example of the method producing the near infrared ray reflection layer includes at least the followings:

(1) coating the surface of the substrate or the like with the curable liquid crystal composition to enter a state of the cholesteric liquid crystal phase, and (2) irradiating the curable liquid crystal composition with UV light to accelerate the curing reaction, and fixing the cholesteric liquid crystal phase, thereby forming a light reflection layer.

A heat ray cutting film having a configuration which is the same as the configuration illustrated in FIG. 1 can be prepared by repeating the processes of (1) and (2) two times on one surface of the substrate.

Moreover, a rotation direction of the cholesteric liquid crystal phase can be adjusted by the kind of liquid crystal to be used or the kind of chiral agent to be added, and a helical pitch (that is, a center reflection wavelength) can be arbitrarily adjusted by the concentration of these materials. It is known that the wavelength in a specific range reflected by a light reflection layer can be shifted by various factors of the production method. The wavelength can be shifted by conditions of the temperature, illuminance, and the irradiation time at the time of fixing the cholesteric liquid crystal phase in addition to the concentration at the time of adding the chiral agent.

In the above process (1), first, the curable liquid crystal composition is applied to the surface of a substrate or to the surface of the underlying light reflection layer. The curable liquid crystal composition is preferably prepared as a coating liquid obtained by dissolving and/or dispersing the materials in a solvent. Coating with the coating liquid may be attained in various methods such as a wire bar coating method, an extrusion coating method, a direct gravure coating method, a reverse gravure coating method, and a die coating method. It is possible to form a coating film by ejecting the liquid crystal composition from the nozzle using an inkjet apparatus.

Next, the curable liquid crystal composition applied to the surface to be a coating film is processed to be a cholesteric liquid crystal phase. In the embodiment where the curable liquid crystal composition is prepared as a coating liquid that contains a solvent, the coating film is dried and the solvent is removed, whereby the coating film may enter a state having a cholesteric liquid crystal phase. To make the coating film have a transition temperature at which the coating film enters a cholesteric liquid crystal phase, the coating film may be optionally heated. For example, once the coating film is heated up to a temperature of the isotropic phase thereof, the coating film is then cooled to a cholesteric liquid crystal phase transition temperature, whereby the coating film could be stably converted into a state of cholesteric liquid crystal phase. The liquid crystal phase transition temperature of the curable liquid crystal composition is preferably within a range of 10° C. to 250° C. in terms of the production suitability, and more preferably 10° C. to 150° C. When the temperature is lower than 10° C., the production process may require a cooling process for lowering the temperature of the coating film to a temperature range in which the film may exhibit a liquid crystal phase. On the other hand, when the temperature is higher than 200° C., the process may require a high temperature in order for the coating film to be in an isotropic liquid state at a further higher temperature than the temperature range in which the film may be once a liquid crystal phase, and as such, is unfavorable in terms of heat energy waste, substrate deformation, and deterioration.

Next, in the process (2), the coating film that enters a state of a cholesteric liquid crystal phase is cured through irradiation with UV light. For UV irradiation, a light source of a UV lamp or the like is used. In this process, the coating film is irradiated with UV light whereby the liquid crystal composition is cured and the cholesteric liquid crystal phase is thereby fixed to form a light reflection layer.

The irradiation energy dose of UV light is not particularly limited. In general, a dose of 100 mJ/cm$^2$ to 800 mJ/cm$^2$ is preferable. The time for which the coating film is irradiated with UV light is also not particularly limited. The time may be determined in consideration of both the sufficient strength of the cured film and the productivity thereof.

To accelerate the curing reaction, the UV irradiation may be carried out under heat. Preferably, the temperature of irradiation with UV light is kept in a range of a cholesteric liquid crystal phase temperature range so as not to disturb the cholesteric liquid crystal phase of the film. The oxygen concentration in the atmosphere participates in the degree of polymerization, and therefore, in case where the reaction could not secure the desired degree of polymerization in air and where the film strength is therefore insufficient, it is desirable that the oxygen concentration in the atmosphere is reduced according to a nitrogen-substitution method or the like. The oxygen concentration is preferably 10% or less, more preferably 7% or less, and most preferably 3% or less. The reaction yield of the curing reaction (for example, polymerization reaction), which is promoted through irradiation with UV light, is preferably 70% or more, more preferably 80% or more, and still more preferably 90% or more in terms of holding the mechanical strength of the layers, suppressing the outflow of unreacted substances from the layers and the like. In order to improve the reaction yield, a method for increasing the radiation dose of UV light or polymerization in a nitrogen atmosphere or under heating conditions is effective. In addition, it is also possible to use a method in which the composition is temporarily polymerized, and held in a higher temperature state than the polymerization temperature, thereby further progressing the reaction through thermal polymerization or a method in which UV light are radiated again (in this case, UV light should be radiated under the conditions satisfying the condition of the present invention). The reaction yield can be measured by comparing the absorption intensities in the IR vibration spectra of the reactive group (for example, polymerizable group) before and after the progression of the reaction.

In the above process, the cholesteric liquid crystal phase is fixed to form the light reflection layer. Here, regarding the "fixed" state of the liquid crystal phase, a condition where the alignment of the liquid crystal compound that exhibits the cholesteric liquid crystal phase is maintained is for a most typical and preferred embodiment. However, not limited thereto but concretely, the fixed state means that the layer has no fluidity in a temperature range of generally 0° C. to 50° C., but −30° C. to 70° C. in a more severe condition, and can continue to stably keep the fixed alignment state thereof without providing any change in the alignment state by any external field or external force. In the present invention, the alignment state of the cholesteric liquid crystal phase is fixed by the curing reaction that is promoted through irradiation with UV light.

In the present invention, it is enough that the optical properties of the cholesteric liquid crystal phase are maintained in the layer, and finally the liquid crystal composition in the light reflection layer does not need to exhibit any more liquid crystallinity. For example, the liquid crystal composition may be polymerized to have an increased molecular weight through the curing reaction to thereby have no more liquid crystallinity.

[Infrared Ray Cutting Member]

The infrared ray cutting film of the present invention may be used alone as a heat ray shielding material or may be laminated with another functional layer. Further, the infrared ray cutting film of the present invention may have a laminate structure which is laminated with glass or the like.

The infrared ray cutting film of the present invention is not particularly limited as long as the infrared ray cutting film is used for selectively reflecting and absorbing heat rays (near infrared rays) and appropriately selected according to the purpose, and examples thereof include an infrared ray cutting member for being bonded to a window of a building or a vehicle and a film for agriculture. Among these, an infrared ray cutting member for being bonded to a window of a building or a vehicle is more preferable in terms of energy saving effect and an infrared ray cutting member for windshield of a vehicle is particularly preferable.

Further, in the present invention, heat rays (near infrared rays) mean near infrared rays (780 nm to 1800 nm) included in sunlight in an amount of approximately 50% thereof.

[Infrared Ray Cutting Laminated Glass]

The infrared ray cutting film of the present invention may be used as infrared ray cutting laminated glass including two sheets of glass plates and the infrared ray cutting film of the present invention which is interposed between the glass plates.

(Laminated Interlayer Film Sheet for Glass)

When infrared ray cutting laminated glass is produced, the glass may be produced after a laminated interlayer film sheet for glass. The laminated interlayer film sheet for glass includes the infrared ray cutting film of the present invention and an interlayer film sheet arranged on at least one outermost layer.

The interlayer film sheet can be bonded to one and/or both surfaces of the infrared ray cutting film of the present invention. In the laminated interlayer film sheet for glass, it is preferable that interlayer film sheets are respectively included on both outermost layers of the infrared ray cutting film of the present invention. By bonding the interlayer film sheet, the interlayer film sheet can be easily incorporated in the laminated glass as a laminated interlayer film sheet for laminated glass. When the interlayer film sheet is bonded thereto, the interlayer film sheet may be bonded in a state in which the substrate remains or after the substrate is peeled off. However, when it is considered that the interlayer film sheet is incorporated in the laminated glass at the subsequent process, preferably, the substrate is peeled off and thereafter the interlayer film sheet is bonded in consideration of the thickness, flexibility, and compression resistance.

As the interlayer film sheet, a normal interlayer film sheet which is used to produce laminated glass can be used. Specific examples thereof include a sheet produced from a composition containing a polyvinyl butyral resin or an ethylene-vinyl acetate copolymer as a main component.

The thickness of the interlayer film sheet is generally 380 µm to 760 µm.

<Method of Producing Laminated Interlayer Film Sheet for Glass]

The infrared ray cutting film of the present invention can be made into a laminated interlayer film sheet for laminated glass interposed between the interlayer film sheets by bonding both surfaces thereof with the interlayer film sheets.

The method of producing a laminated interlayer film sheet for glass preferably includes at least the following processes:
(1) a first process of bonding a first interlayer film sheet on one surface of the infrared ray cutting film of the present invention to obtain a first laminate, and
(2) a second process of bonding a second interlayer film sheet to the surface on the opposite side of the surface of the first laminate to which the first interlayer film sheet is bonded. The first and second processes may be performed sequentially or simultaneously. In addition, after one process is carried out, another process may be carried out after temporarily holding and transporting the resultant.

A known bonding method can be used for bonding the interlayer film sheet, but a lamination treatment is preferably used. When the lamination treatment is performed, it is preferable that the treatment is performed under the conditions of heating and pressing to a certain extent such that the heat ray cutting film and the interlayer film sheet are not peeled off after the processing.

In order to stably perform the lamination, the temperature of the film surface on the side to which the interlayer film sheet is adhered is preferably 50° C. to 130° C. and more preferably 70° C. to 100° C.

The pressing is preferably performed at the time of lamination. The condition of pressing is preferably less than 2.0 kg/cm$^2$, more preferably 0.5 kg/cm$^2$ to 1.8 kg/cm$^2$, and still more preferably 0.5 kg/cm$^2$ to 1.5 kg/cm$^2$.

In addition, the substrate (or a laminate at least including a substrate) may be peeled off from the infrared ray cutting film of the present invention simultaneously, immediately after, or immediately before the lamination. That is, a substrate may not be present in a laminated interlayer film sheet obtained after the lamination.

A laminated interlayer film sheet for glass without a substrate can be produced using this method and an infrared ray cutting laminated glass without a substrate can be easily produced using the laminated interlayer film sheet for glass. In order for the substrate to be stably peeled off without damage or the like, the temperature of the substrate at the time when the substrate is peeled off from the light reflection layer of the cholesteric liquid crystal phase is preferably 40° C. or higher and more preferably 40° C. to 60° C.

(Configuration of Laminated Glass)

As the glass plate, a normal glass plate can be used.

Heat-absorbing glass having absorption in the visible light area can be used for improving the heat shielding performance by being combined with the infrared ray cutting film of the present invention. By adjusting absorption of the visible light area, visibility (transmittance) and heat shielding performance as glass can be adjusted. The absorption of the visible light area or the color tone as transmitted light can be adjusted by the heat-absorbing glass containing metal oxides such as iron, tin, nickel, cobalt, and selenium as described in Japanese Patent No. 2544035 and Japanese Patent No. 2617223. For example, in a case of being used as windshields for a vehicle, it is preferable to improve heat shielding performance while absorption in the visible light area is suppressed so as to satisfy "a visible light transmittance (standard light source A) of 70% or more" defined by JIS-R-3211 as laminated glass and the color tone of the transmitted light is adjusted. As the heat-absorbing glass, the visible light transmittance (standard light source A) is preferably in the range of 80% to 95%, and a dominant wavelength measured using the standard A light source is preferably in the range of 495 nm to 560 nm.

The thickness of the glass plate is not particularly limited and a preferred range thereof is changed depending on usage. For example, for the usage as windshields (window shield) of a transport vehicle, it is preferable to use a glass plate having a thickness of 2.0 mm to 2.3 mm in general. Further, for the usage as a heat-shielding window material for a building such as a house or a building, it is preferable to use a glass plate having a thickness of 40 µm to 300 µm in general. However, the range of the thickness is not limited to the above.

[Method of Producing Laminated Glass]

The laminated interlayer film sheet for laminated glass can be made into laminated glass by being interposed between two sheets of glass plates.

It is preferable that the method of producing the laminated glass includes a step of producing a laminate sandwiched between glass plates by interposing the laminated interlayer film sheet for laminated glass between two sheets of glass plates and a step of heating and pressing the laminate sandwiched between the glass plates.

As a specific production method, a known method of producing laminated glass can be appropriately used.

In general, a method of interposing a laminated interlayer film sheet for laminated glass between two sheets of glass plates, repeatedly performing a heat treatment and a pressure treatment (squeezing or the like using a rubber roller) for several times, and finally performing a heat treatment using an autoclave or the like under the pressure condition is employed.

It is preferable to heat and press the laminate sandwiched between the glass plates in which two interlayer films are not in contact to each other.

Bonding the laminate sandwiched between the glass plates to the glass plates may be attained, for example, by prebonding them under reduced pressure, using a vacuum bag or the like, at a temperature of 80° C. to 120° C. for a period of from 30 minutes to 60 minutes, and thereafter bonding them in an autoclave under a pressure of from 1.0 MPa to 1.5 MPa at a temperature of from 120° C. to 150° C. thereby producing laminated glass in which the laminate is sandwiched between the two glass plates. If desired, they may be bonded to each other via an adhesive material or the like.

In this case, preferably, the pressure is from 1.0 MPa to 1.5 MPa, the temperature is from 120° C. to 150° C., and the thermally bonding time is from 20 minutes to 90 minutes.

After the thermal bonding, the cooling mode is not particularly limited. The system may be allowed to cool while the pressure is suitably released, whereby a laminated glass is obtained. In the present invention, it is desirable that the system is cooled while the pressure therein is kept as such after the thermal bonding, in terms of preventing the laminated glass to be obtained from being wrinkled or cracked. The mode of cooling the system while the pressure is kept as such means that the apparatus is cooled so that the inner pressure inside the apparatus at 40° C. is from 75% to 100% of the inner pressure inside the apparatus where the laminated glass has been thermally bonded (preferably at 130° C.). The method of cooling the system while the pressure therein is kept as such is not specifically defined so far as the pressure in the system when cooled to 40° C. can fall within the above range. However, preferred is an embodiment where the inner area of the apparatus is gradually cooled with no pressure leak therethrough in such a manner that the inner pressure inside the apparatus is naturally lowered with the decrease in the temperature therein, or an embodiment where the system is cooled with further external pressure in such a manner that the inner pressure inside the apparatus is not lowered with the decrease in the temperature therein. In case where the system is cooled while the pressure therein is kept as such, it is desirable that the laminated glass is thermally bonded at a temperature from 120° C. to 150° C. and then allowed to cool for 1 hour to 5 hours to 40° C.

Preferably, the method of the present invention includes a step of releasing the pressure, after cooling the system while the pressure therein is kept as such. Concretely, it is desirable that the system is first cooled while the pressure therein is kept as such, and then, after the temperature inside the autoclave reaches 40° C. or lower, the system is cooled while releasing the pressure.

From the above, it is desirable that the method of producing laminated glass includes a step of laminating the first glass, the first interlayer film, the infrared ray reflection layer, the second interlayer film, and the second glass in this order, a step of thermally bonding them under a pressure of 1.0 MPa to 1.5 MPa at a temperature of 120° C. to 150° C., a step of cooling the system while the pressure therein is kept as such, and a step of releasing the pressure.

The area of thermally bonding the infrared ray cutting film to the interlayer film may be the area that covers the entire area of the glass plates, but may be the peripheral area of the glass plates. Thermally bonding the two at the peripheral area prevents the glass plate from being wrinkled.

EXAMPLES

Hereinafter, the characteristics of the present invention are described more concretely with reference to the following Examples.

In the following Examples, the materials, the used amounts and ratios thereof, the details of the treatment, and the treatment procedures may be suitably modified or changed in a range not departing from the scope of the present invention. Accordingly, the scope of the present invention should not be limitatively interpreted by Examples described below.

Production Example 1

<Preparation of Coating Liquid for Near Infrared Ray Absorbing Layer>

(Preparation of Pigment Dispersion)

Synthesis of Exemplary Compounds (D-31 and D-142)

The following near infrared ray absorbing compounds D-142 and D-31 were respectively synthesized with reference to JP-A-2011-68731.

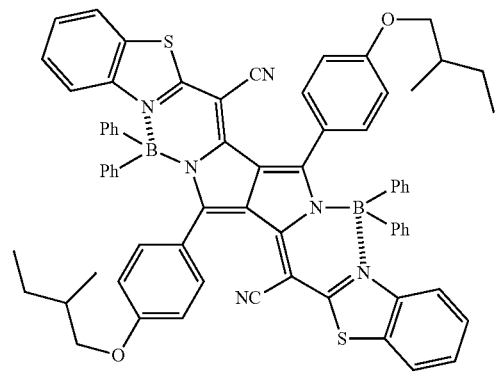

-continued

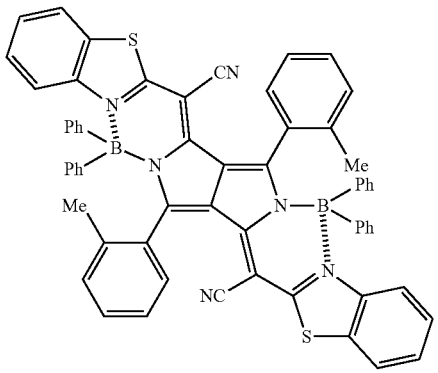

D-31

—Preparation of Pigment Dispersion Liquids A-1 and A-2—

A dispersion medium (90 parts by mass) was added to a near infrared ray absorbing compound (5 parts by mass) listed in Table 1 below and a dispersant (5 parts by mass) so as to make 100 parts by mass of a mixture. Further, 100 parts by mass of zirconia beads having a diameter of 0.1 mmφ were added and a filtration treatment was applied thereto after a treatment using a planetary ball mill was performed at 300 rpm for 8 hours, thereby preparing pigment dispersion liquids A-1 and A-2 formed of fine particles.

—Evaluation of Pigment Dispersion Liquids A-1 and A-2—

Some of the pigment dispersion liquid A-1 and A-2 were diluted by a dispersion medium and an absorption spectrum was measured using UV3100PC (manufactured by Shimadzu Corporation). The obtained results are listed in Table 1 below. Further, it was confirmed that D-142 and D-31 were near infrared ray absorbents having a maximum absorption wavelength of 750 nm to 920 nm from the obtained results.

Figure 3:
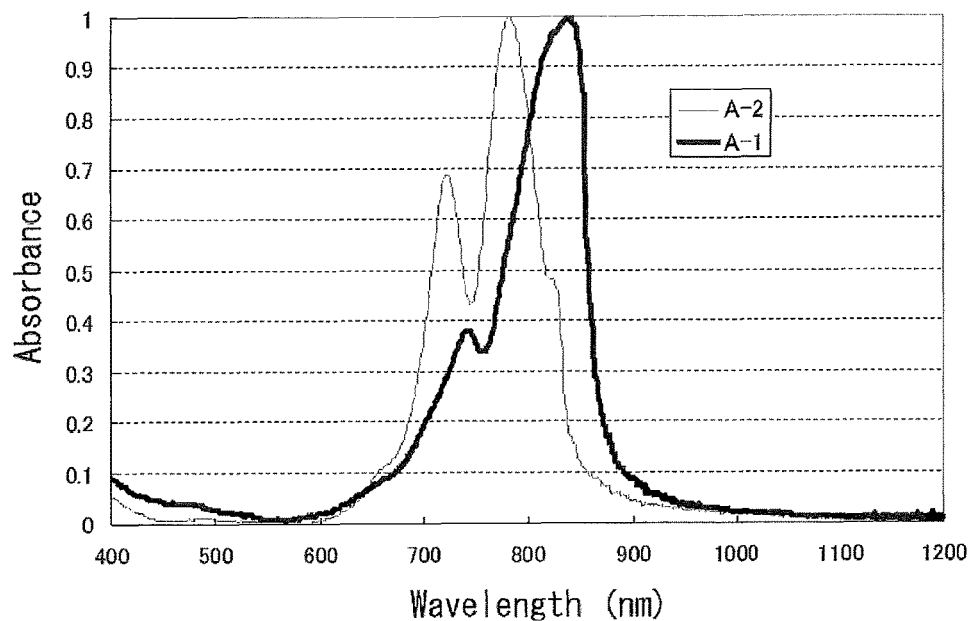
FIG. 3 is a graph showing spectra in which the absorbance at the maximum absorption wavelengths of pigment dispersions A-1 and A-2 is standardized as 1.

A spectrum in which the absorbance of the pigment dispersion liquids A-1 and A-2 at the maximum absorption wavelength is standardized as 1 is illustrated in FIG. 3. From FIG. 3, it is understood that the pigment dispersion liquids A-1 and A-2 at 550 nm have an absorbance of 0.1 or less when the absorbance at the maximum absorption wavelength is 1, almost do not have absorption of an absorption visible portion, and have high invisibility.

Further, the number average particle diameters of each near infrared ray absorbing compounds in the pigment dispersion liquids A-1 and A-2 were measured using Zetasizer Nano (manufactured by Malvern Instruments Ltd.). The measured values are listed in Table 1 below.

TABLE 1

| Pigment | Dispersant | Dispersion medium | Maximum absorption wavelength | Number average particle diameter |
|---|---|---|---|---|
| A-1 | D-142 | W-1 | Cyclohexanone | 846 nm | 39 nm |
| A-2 | D-31 | W-1 | Cyclohexanone | 788 nm | 95 nm |

W-1: SOLSPERSE 39000 (trade names, manufactured by Lubrizol Corporation)

(Preparation of Coating Liquid B for Near Infrared Ray Absorbing Layer)

Coating liquids (B-1) and (B-2) for a near infrared absorbing layer were prepared so as to have the composition described in Tables 2 and 3 below using the pigment dispersion liquids A-1 and A-2 prepared above.

TABLE 2

Table of composition of coating liquid (B-1)

| Material (kind) | Name of material | Prescribed amount |
|---|---|---|
| Pigment dispersion liquid | A-1 | 40 parts by mass |
| UV curable monomer | Pentaerythritol triacrylate | 10 parts by mass |
| Polymerization initiator | Irgacure 819 (Ciba Specialty Chemicals) | 0.5 parts by mass |
| Solvent | Cyclohexanone | 49.5 parts by mass |

TABLE 3

Table of composition of coating liquid (B-2)

| Material (kind) | Name of material | Prescribed amount |
|---|---|---|
| Pigment dispersion liquid | A-2 | 40 parts by mass |
| UV curable monomer | Pentaerythritol triacrylate | 10 parts by mass |
| Polymerization initiator | Irgacure 819 (Ciba Specialty Chemicals) | 0.5 parts by mass |
| Solvent | Cyclohexanone | 49.5 parts by mass |

Production Example 2

<Preparation of Coating Liquid for Near Infrared Ray Reflection Layer>

(Preparation of Coating Liquid)

A coating liquid (R1) with the composition listed in Table 4 below and a coating liquid (L1) with the composition listed in Table 5 were respectively prepared.

TABLE 4

Table of composition of coating liquid (R1)

| Material (kind) | Name of material (manufacturer) | Prescribed amount |
|---|---|---|
| Rod-shaped liquid crystal compound | RM-257 (Merck) | 10000 parts by mass |
| Chiral agent | LC-756 (BASF) | Adjustment in accordance with target reflection wavelength |
| Polymerization initiator | Irgacure 819 (Ciba Specialty Chemicals) | 0.419 parts by mass |
| Alignment control agent | Compound 1 shown below | 0.016 parts by mass |
| Solvent | 2-butanone (Wako Pure Chemical Industries) | 15.652 parts by mass |

TABLE 5

Table of composition of coating liquid (L1)

| Material (kind) | Name of material (manufacturer) | Prescribed amount |
|---|---|---|
| Rod-shaped liquid crystal compound | RM-257 (Merck) | 10000 parts by mass |
| Chiral agent | Compound 2 shown below | Adjustment in accordance with target reflection wavelength |
| Polymerization initiator | Irgacure 819 (Ciba Specialty Chemicals) | 0.419 parts by mass |
| Alignment control agent | Compound 1 shown below | 0.016 parts by mass |
| Solvent | 2-butanone (Wako Pure Chemical Industries) | 15.652 parts by mass |

Alignment control agent: Compound 1 (compound described in JP-A-2005-99248)

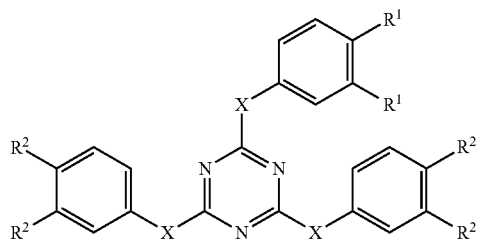

| $R^1$ | $R^2$ | X |
|---|---|---|
| $O(CH_2)_2O(CH_2)_2(CF_2)_6F$ | $O(CH_2)_2O(CH_2)_2(CF_2)_6F$ | NH |

Chiral agent: Compound 2 (compound described in JP-A-2002-179668)

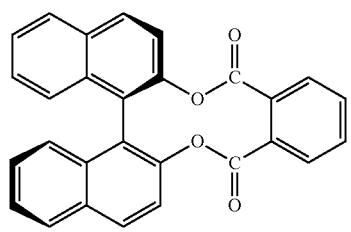

Further, coating liquids (R2) to (R4) were prepared in the same manner as that of the coating liquid (R1) except that the prescribed amount of a chiral agent LC-756 of the coating liquid (R1) was changed such that the reflection wavelength became the reflection wavelength listed in Table 6 below. The reflection center wavelengths of coating liquids (R1) to (R4) are listed in Table 6 below.

TABLE 6

| Coating liquid (R1) | 750 nm |
|---|---|
| Coating liquid (R2) | 800 nm |
| Coating liquid (R3) | 850 nm |
| Coating liquid (R4) | 1000 nm |

Further, coating liquids (L2) to (L3) were prepared in the same manner as that of the coating liquid (L1) except that the prescribed amount of a chiral agent compound 2 of the coating liquid (L1) was changed such that the reflection wavelength became the reflection wavelength listed in Table 7 below. The reflection center wavelengths of coating liquids (L1) to (L3) are listed in Table 7 below.

TABLE 7

| Coating liquid (L1) | 750 nm |
|---|---|
| Coating liquid (L2) | 800 nm |
| Coating liquid (L3) | 850 nm |

Example 1

<Creation of Infrared Ray Cutting Film>

The coating liquid (R1) prepared in Production Example 2 was applied onto PET and a film was formed under the condition of a method Y described below.

(Preparation of Near Infrared Ray Reflection Layer: Method Y)

A near infrared ray reflection layer was prepared using the prepared coating liquid (R1) according to the following procedures. A PET film (manufactured by FUJIFILM Corporation, free from undercoat layer, thickness: 188 μm) was used as a substrate.

(1) The PET film was coated with the coating liquid using a wire bar such that the thickness of the film after drying became 6 μm at room temperature.

(2) After the film was dried for 30 seconds at room temperature and the solvent was removed, the resultant was heated for 2 hours in an environment of at 125° C., and then a cholesteric liquid crystal phase was obtained at 95° C. Next, the cholesteric liquid crystal phase was irradiated with UV rays with 60% of output for 6 seconds to 12 seconds using an electrodeless lamp "D VALVE" (90 mW/cm, manufactured by Fusion UV System, Inc.) and then fixed, thereby preparing a film (near infrared ray reflection layer).

When the reflection spectrum was measured on a laminate in which the coating liquid (R1) was applied on the obtained PET film under the condition of the method Y using V-670 (manufactured by JASCO Corporation), the reflectance at 750 nm was 48%.

The coating liquid (B-1) was applied onto the near infrared ray reflection layer formed as described above, a film was formed under the condition of a method X described below to prepare a near infrared ray absorbing layer, thereby obtaining an infrared ray cutting film F1.

(Preparation of Near Infrared Ray Absorbing Layer: Method X)

The near infrared ray reflection layer (liquid crystal film) was coated with the coating liquid (B-1) using a wire bar such that the thickness of the film after drying became 1 μm at room temperature. After the film was dried for 90 seconds at room temperature and the solvent was removed, the resultant was heated for 90 seconds in an environment of a temperature of 90° C. Next, the resultant was irradiated with UV rays with 60% of output for 3 seconds to 6 seconds using an electrodeless lamp "D VALVE" (90 mW/cm, manufactured by Fusion UV System, Inc.), thereby preparing a near infrared ray absorbing layer.

The obtained infrared ray film F1 was used as an infrared ray cutting film of Example 1.

<Evaluation>

(Invisibility)

In regard to the prepared infrared ray cutting film, the transmittance at a wavelength of 550 nm was calculated using a spectrophotometer "V-670" (manufactured by JASCO Corporation).

When the transmittance at 550 nm was 80% or more, the evaluation was made as "O," and when the transmittance thereof was less than 80%, the evaluation was made as "X."

The obtained results are listed in Table 8.

(Light Resistance)

The prepared infrared ray cutting film was irradiated with light using a xenon lamp at 220000 lux for 72 hours. The absorbance of the near infrared ray absorbing layer after irradiation with light at the maximum absorption wavelength was measured and a residual ratio with respect to the absorbance of the near infrared ray absorbing layer before irradiation with light at the maximum absorption wavelength was acquired.

Residual ratio=(absorbance after irradiation with light)÷(absorbance before irradiation with light)×100

When the residual ratio was 90% or more, the evaluation was made as "O," and when the residual ratio was less than 90%, the evaluation was made as "X."

Obtained results are listed in Table 8 below.

(Heat Shielding Performance)

The solar reflectance of the prepared infrared ray cutting film was acquired based on a method described in JIS5759 from the transmittance and the reflectance of each wavelength measured in the range of 350 nm to 2100 nm. In the evaluation of the heat shielding performance, it is preferable that the reflectance is high.

O: the reflectance is 10% or more
X: the reflectance is less than 10%

Example 2

An infrared ray film F2 was obtained in the same manner as that of Example 1 except that the coating liquid (B-2) was used instead of the coating liquid (B-1) in Example 1.

The obtained infrared ray film F2 was used as the infrared ray cutting film of Example 2.

The invisibility, the light resistance, and the heat shielding performance of the infrared ray cutting film of Example 2 were evaluated in the same manner as those of Example 1. The results thereof are listed in Table 8.

Comparative Example 1

(Preparation of Coating Liquid (B-3) for Near Infrared Ray Absorbing Layer)

2 parts of phthalocyanine described in Example 3 of JP-A-2001-106689 was mixed with 98 parts of cyclohexanone, a coating liquid (B-3) for a near infrared ray absorbing layer was created. The coating liquid (B-3) was diluted with cyclohexanone and the absorption spectrum was measured. The maximum absorption wavelength was 850 nm and the absorbance at 550 nm when the absorbance at the maximum absorbing wavelength was 1 exceeded 0.1, and coloration was recognized.

(Preparation of Infrared Ray Cutting Film)

An infrared ray film E1 was obtained in the same manner as that of Example 1 except that the coating liquid (B-3) was used instead of the coating liquid (B-1) in Example 1.

The obtained infrared ray film E1 was used as the infrared ray cutting film of Comparative Example 1.

The invisibility, the light resistance, and the heat shielding performance of the infrared ray cutting film of Comparative Example 1 were evaluated in the same manner as those of Example 1. The results thereof are listed in Table 8 below.

Comparative Example 2

(Preparation of Infrared Ray Cutting Film)

The coating liquid (B-1) was applied onto PET and a film was formed under the condition of the method X described above to prepare a near infrared ray absorbing layer, thereby obtaining an infrared ray cutting film E2. The obtained infrared ray film E2 was used as the infrared ray cutting film of Comparative Example 2.

The invisibility, the light resistance, and the heat shielding performance of the infrared ray cutting film of Comparative Example 2 were evaluated in the same manner as those of Example 1. The results thereof are listed in Table 8 below.

TABLE 8

| | Near infrared ray absorbing layer | | | Near infrared ray reflection layer | Invisibility | Heat resistance | Heat shielding performance |
|---|---|---|---|---|---|---|---|
| | Film name | Coating liquid | Infrared ray absorbing pigment | | | | |
| Example 1 | F1 | B-1 | D-142 | R1 | O | O | O |
| Example 2 | F2 | B-2 | D-31 | R1 | O | O | O |
| Comparative Example 1 | E1 | B-3 | Phthalocyanine | R1 | X | X | O |
| Comparative Example 2 | E2 | B-1 | D-142 | None | O | O | X |

From Table 8, according to the present invention, an infrared ray cutting film with excellent invisibility and robustness and high heat shielding performance can be obtained.

Example 3

<Preparation of Infrared Ray Cutting Film Obtained by Laminating Two or More Near Infrared Ray Reflection Layers>

A near infrared ray reflection layer was prepared using the prepared coating liquids (R2) and (L2) prepared in Production Example 2 according to the following procedures. A PET film (manufactured by FUJIFILM Corporation, free from undercoat layer, thickness: 188 μm) was used as a substrate.

(1) The PET film was coated with the respective coating liquids using a wire bar such that the thickness of the film after drying became 6 μm at room temperature.

(2) After the film was dried for 30 seconds at room temperature and the solvent was removed, the resultant was heated for 2 minutes in an environment of at 125° C., and then a cholesteric liquid crystal phase was obtained at 95° C.

Next, the cholesteric liquid crystal phase was irradiated with UV rays with 60% of output for 6 seconds to 12 seconds using an electrodeless lamp "D VALVE" (90 mW/cm, manufactured by Fusion UV System, Inc.) and then fixed, thereby preparing a film (light reflection layer).

(3) The above-described processes (1) and (2) were repeatedly performed after cooling at room temperature and a near infrared ray reflection layer having two layers of laminated cholesteric liquid crystal phases was prepared. In addition, application was performed in order of the coating liquid (R2) and the coating liquid (L2).

An infrared ray cutting film P3 was obtained by forming a near infrared ray absorbing layer using the coating liquid (B-1) in the same manner as that of Example 1 except that a laminate in which two near infrared ray reflection layers were laminated on PET obtained as described above was used instead of the laminate in which the near infrared ray reflection layer formed from the coating liquid (R1) was laminated on PET in Example 1.

The obtained infrared ray film F3 was used as an infrared ray cutting film of Example 3.

Example 4

An infrared ray cutting film F4 was obtained by forming a near infrared ray absorbing layer using the coating liquid (B-2) in the same manner as that of Example 2 except that a laminate in which two near infrared ray reflection layers were laminated on PET formed in Example 3 was used instead of the laminate in which the near infrared ray reflection layer formed from the coating liquid (R1) was laminated on PET in Example 2.

The obtained infrared ray film F4 was used as an infrared ray cutting film of Example 4.

Comparative Example 3

A laminate in which two layers of near infrared ray reflection layers were laminated on PET formed in Example 3 was used as an infrared ray cutting film E3 and this was used as an infrared ray cutting film of Comparative Example 3. In addition, the infrared ray cutting film of Comparative Example 3 was free from a near infrared ray absorbing layer.

<Evaluation>

When the invisibility, the light resistance, and the heat shielding performance of the infrared ray cutting films of Examples 3 and 4, and Comparative Example 3 were evaluated in the same manner as those of Example 1, all were evaluated as "O."

(Glare Reduction Test Using Absorbing Layer)

The infrared ray cutting films F3, F4, and E3 were placed on white paper on a flat desk such that PET was put on the bottom and the films were observed under a fluorescent lamp from an oblique direction. Glare due to red light was confirmed in the infrared ray cutting film E3 of Comparative Example 3, the glare was reduced in the infrared ray cutting film F3 of Example 3, and the glare was further reduced in the infrared ray cutting film F4 of Example 4 so that the glare was not recognized.

Example 5

<Preparation of Laminated Glass Using Infrared Ray Cutting Film>

(Preparation of Coating Liquid)

A coating liquid (U1) for an easily-adhesive layer was prepared according to the following composition.

Styrene acrylic resin Aron S-1001 (manufactured by Toa Gosei Co., Ltd., solid content concentration: 50%) 20 parts by mass Methoxy propyl acetate (PGMEA) 80 parts by mass A coating liquid (S1) for an undercoat layer was prepared according to the following composition.

Acrylic ester resin Jurymer ET-410 (manufactured by Toa Gosei Co., Ltd., solid content concentration: 30%) 50 parts by mass Methanol 50 parts by mass A coating liquid (S2) for an undercoat layer was prepared according to the following composition by mixing ITO fine particles and methanol, performing an ultrasonic wave dispersion treatment for 30 minutes, preparing a liquid in which ITO fine particles having an average dispersion particle diameter of 60 nm were dispersed, and mixing the liquid and an acrylic ester resin.

Acrylic ester resin Jurymer ET-410 (manufactured by Toa Gosei Co., Ltd., solid content concentration: 30%) 45 parts by mass Methanol 53.5 parts by mass ITO fine particles (average particle diameter: 30 nm) 1.5 parts by mass A coating liquid (H1) for an alignment layer was prepared according to the following composition.

Modified polyvinyl alcohol PVA 203 (manufactured by Kuraray Co., Ltd.) 10 parts by mass Glutaraldehyde 0.5 parts by mass Water 371 parts by mass Methanol 119 parts by mass A tungsten oxide coating liquid (C1) having the composition listed in Table 9 was prepared.

TABLE 9

| Material (kind) | Name of material | Prescribed amount |
|---|---|---|
| Composite tungsten oxide | Cesium-containing tungsten oxide dispersion liquid (Sumitomo Metal Mining) | 50 parts by mass |
| UV curable monomer | A-TMMT (Shin-Nakamura Chemical) | 5 parts by mass |
| Polymerization initiator | Irgacure 819 (Ciba Specialty Chemicals) | 0.4 parts by mass |
| Solvent | Methyl isobutyl ketone | 44.6 parts by mass |

A coating liquid (I1) for an easily-adhesive layer having the following composition was prepared.

Polyvinyl butyral resin B1776 (manufactured by Changchun Co., Ltd. (Taiwan)) 10 parts by mass Methoxy propyl acetate (PGEMA) 100 parts by mass A coating liquid (I2) for an easily-adhesive layer containing a diimmonium pigment was prepared according to the following composition by mixing a diimmonium pigment and methyl ethyl ketone and then mixing the mixture with a polyvinyl butyral resin.

Polyvinyl butyral resin B1776 (manufactured by Changchun Co., Ltd. (Taiwan)) 10 parts by mass Methyl ethyl ketone (MEK) 100 parts by mass Diimmonium pigment CIR-RL (manufactured by Japan Carlit Co., Ltd.) 1.5 parts by mass (Preparation of Infrared Ray Cutting Film)

A PET film (manufactured by Fujifilm Corporation, thickness: 188 μm) was coated with the coating liquid (U1) for an easily-adhesive layer using a wire bar such that the film thickness after drying became 0.5 μm. Subsequently, the film was heated at 150° C. for 10 minutes, dried, and solidified, thereby forming an easily-adhesive layer (undercoat layer).

Next, the surface of the PET film with the easily-adhesive layer prepared in the above on the side on which the easily-adhesive layer was not coated was coated with the coating liquid (S1) for an undercoat layer using a wire bar such that the film thickness after drying became 0.25 μm. Subsequently, the film was heated at 150° C. for 10 minutes, dried, and solidified, thereby forming an undercoat layer.

Subsequently, the formed undercoat layer was coated with the coating liquid (H1) for an alignment layer using a wire bar such that the film thickness after drying became 1.0 μm. Next, the resultant was heated at 100° C. for 2 minutes, dried, and solidified, thereby forming an alignment layer. The alignment layer was subjected to a rubbing treatment (Rayon cloth, pressure: 0.1 kgf, rotation speed: 1000 rpm, transportation speed: 10 m/min, times: one reciprocating).

Next, a near infrared ray reflection layer of three laminated layers of cholesteric liquid crystal phases was formed on the formed alignment layer under the same conditions of the method of forming the near infrared ray reflection layer of Example 3 using coating liquids (R3), (R4), and (L3).

Next, the coating liquid (B-1) for a near infrared ray absorbing layer was laminated on the surface of the near infrared ray reflection layer formed under the same conditions of the method of Example 1 and then the tungsten oxide coating liquid (C1) was laminated thereon. The process was performed using a method which was the same as the method of coating with the coating liquid (B-1) for a near infrared ray absorbing layer except that the condition of laminating the coating liquid (C1) was changed so that the film thickness after coating using the method of coating with the coating liquid (B-1) for a near infrared ray absorbing layer became 2 μm. Further, the tungsten oxide coating liquid (C1) was coated with the coating liquid (I1) for an easily-adhesive layer using a wire bar such that the film thickness after drying became 1.0 μm. Subsequently, the resultant was heated at 150° C. for 10 minutes, dried, solidified, and the easily-adhesive layer was formed, thereby preparing an infrared ray cutting film F5.

(Preparation of Infrared Ray Cutting Laminated Glass)

Next, the infrared ray cutting film F5 prepared in the above and a polyvinyl butyral interlayer film sheet for laminated glass (thickness: 380 μm) were subjected to a laminate treatment (heating temperature: 80° C., pressing force: 1.5 kg/cm², transporting speed: 0.1 m/min) using a laminate (manufactured by Taisei Laminator Co., Ltd.), thereby preparing a laminated interlayer film sheet for laminated glass.

Subsequently, the laminated interlayer film sheet for laminated glass prepared in the above was interposed between two sheets of transparent glass (thickness: 2 mm), and put into a rubber bag, and the pressure thereof was reduced using a vacuum pump. Subsequently, the temperature was raised to 90° C. under reduced pressure, maintained for 30 minutes, and the pressure and temperature were temporarily returned to normal pressure and temperature. Subsequently, the resultant was maintained for 20 minutes under the conditions of a pressure of 1.3 MPa and a temperature of 130° C. in an autoclave. Next, the pressure and temperature were returned to normal pressure and temperature, thereby preparing infrared ray cutting laminated glass G1.

Example 6

(Preparation of Infrared Ray Cutting Film)

A PET film (manufactured by Fujifilm Corporation, thickness: 188 μm) was coated with the coating liquid (U1) for an easily-adhesive layer using a wire bar such that the film thickness after drying became 0.5 μm. Subsequently, the film was heated at 150° C. for 10 minutes, dried, and solidified, thereby forming an easily-adhesive layer (undercoat layer).

Next, the surface of the PET film with the easily-adhesive layer prepared in the above on the side on which the easily-adhesive layer was not coated was coated with the coating liquid (S2) for an undercoat layer using a wire bar such that the film thickness after drying became 0.25 μm. Subsequently, the film was heated at 150° C. for 10 minutes, dried, and solidified, thereby forming an undercoat layer.

Subsequently, the formed undercoat layer was coated with the coating liquid (H1) for an alignment layer using a wire bar such that the film thickness after drying became 1.0 μm. Next, the resultant was heated at 100° C. for 2 minutes, dried, and solidified, thereby forming an alignment layer. The alignment layer was subjected to a rubbing treatment (Rayon cloth, pressure: 0.1 kgf, rotation speed: 1000 rpm, transportation speed: 10 m/min, times: one reciprocating).

Next, a near infrared ray reflection layer of three laminated layers of cholesteric liquid crystal phases was formed on the formed alignment layer under the same conditions of the method of forming the near infrared ray reflection layer of Example 3 using coating liquids (R3), (R4), and (L3).

Next, the coating liquid (B-1) for a near infrared ray absorbing layer was laminated on the surface of the near infrared ray reflection layer formed under the same conditions of the method of Example 1. Further, the coating liquid (I2) for an easily-adhesive layer containing a diimmonium pigment was applied using a wire bar such that the film thickness after drying became 1.0 μm. Subsequently, the resultant was heated at 100° C. for 10 minutes, dried, and solidified and an easily-adhesive layer was formed, thereby preparing an infrared ray cutting film F6.

(Preparation of Infrared Ray Cutting Laminated Glass)

Next, the infrared ray cutting film F6 prepared in the above and a polyvinyl butyral interlayer film sheet for laminated glass (thickness: 380 μm) were subjected to a laminate treatment (heating temperature: 80° C., pressing force: 1.5 kg/cm², transporting speed: 0.1 m/min) using a laminator (manufactured by Taisei Laminator Co., Ltd.), thereby preparing a laminated interlayer film sheet for laminated glass.

Subsequently, the laminated interlayer film sheet for laminated glass prepared in the above was interposed between two sheets of transparent glass (thickness: 2 mm), and put into a rubber bag, and the pressure thereof was reduced using a vacuum pump. Subsequently, the temperature was raised to 90° C. under reduced pressure, maintained for 30 minutes, and the pressure and temperature were temporarily returned to normal pressure and temperature. Subsequently, the resultant was maintained for 20 minutes under the conditions of a pressure of 1.3 MPa and a temperature of 130° C. in an autoclave. Next, the pressure and temperature were returned to normal pressure and temperature, thereby preparing infrared ray cutting laminated glass G2.

<Evaluation>

Figure 4:
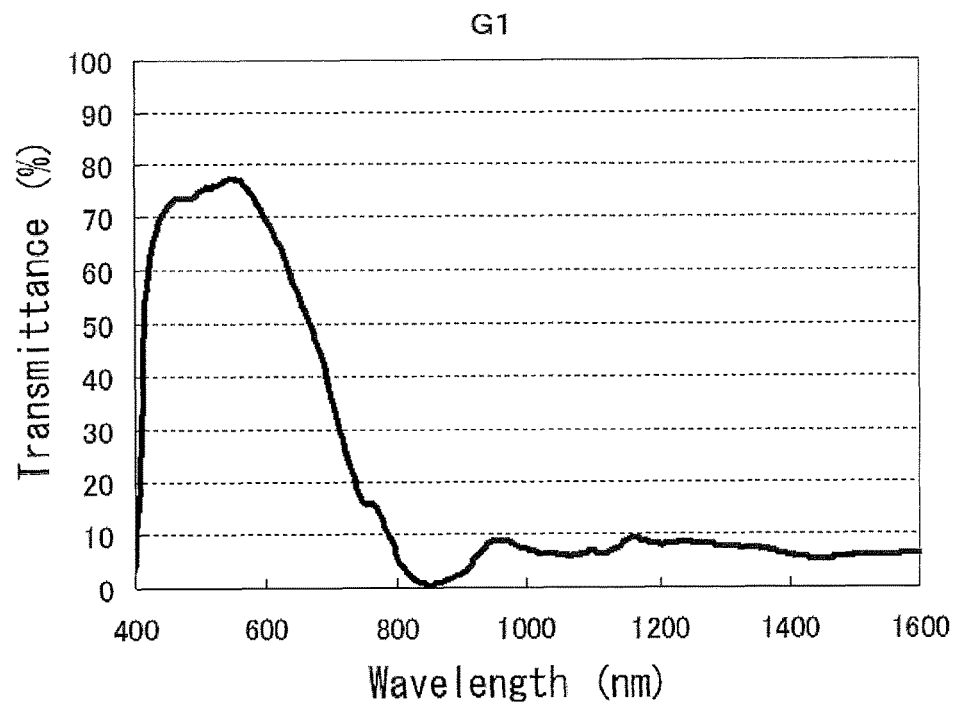
FIG. 4 is a graph showing a transmission spectrum of infrared ray cutting laminated glass G1 of Example 5.
Figure 5:
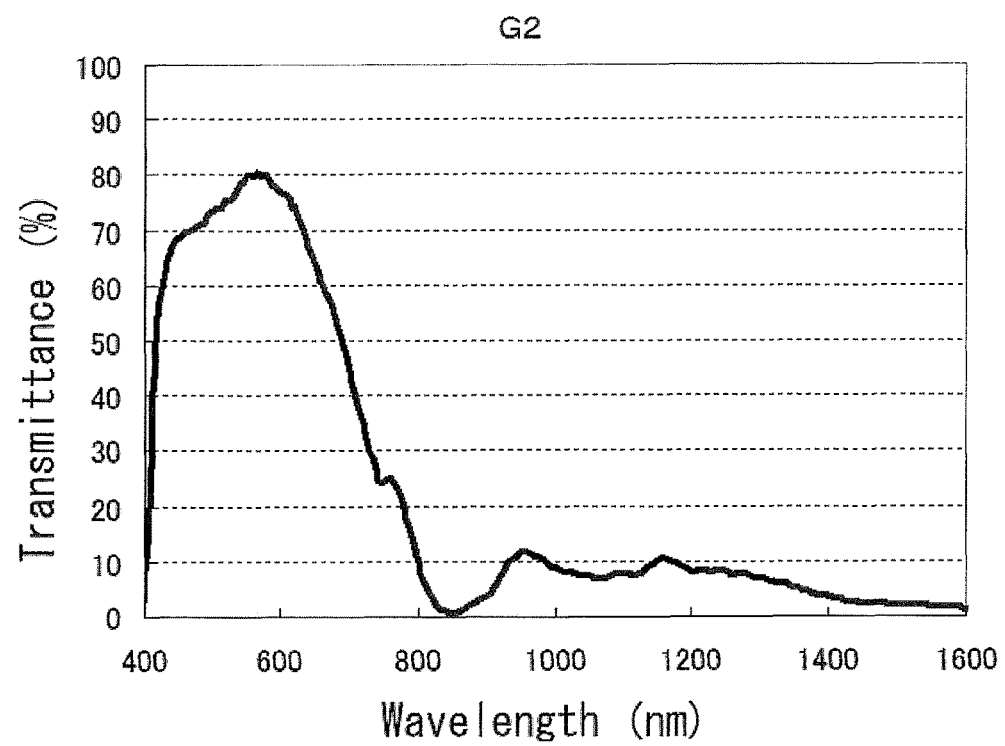
FIG. 5 is a graph showing a transmission spectrum of infrared ray cutting laminated glass G2 of Example 6.

The measurement results of transmission spectra of laminated glass G1 and G2 respectively prepared in Examples 5 and 6 are shown in FIGS. 4 and 5.

Based on the method described in JIS5759, the visible light transmittance of the infrared ray cutting laminated glass G1 was 72.1% and the visible light transmittance of the infrared ray cutting laminated glass G2 was 76.2%.

From the results of the above-described visible light transmittance of FIGS. 4 and 5, the infrared ray cutting laminated glass G1 and glass G2 of the present invention have high visible light transmittance and exceedingly excellent heat shielding performance and thus the glass G1 and glass G2 can be preferably used as a member for a window of a vehicle or a building. Further, since the visible light transmittances of the infrared ray cutting laminated glass G1 and glass G2 are 70% or more, the glass G1 and glass G2 can be preferably used as a windshield of an automobile.

Since the infrared ray cutting film of the present invention has excellent invisibility, robustness, and heat shielding performance, the infrared ray cutting film can be preferably used as various members, which are required to prevent transmission of heat rays, such as a film or a laminate structure for vehicles, for example, an automobile and a bus, and a film or a laminate structure for a building.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/074631, filed on Sep. 12, 2013, and Japanese Patent Application No. 2012-218443 filed on Sep. 28, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

REFERENCE SIGNS LIST

12: transparent substrate
14a: near infrared ray reflection layer obtained by fixing cholesteric liquid crystal layer
14b: near infrared ray reflection layer obtained by fixing cholesteric liquid crystal layer
19: near infrared ray absorbing layer including near infrared ray absorbent
20: metal fine particle dispersion or another infrared ray absorbing layer including diimmonium pigment.

What is claimed is:

1. An infrared ray cutting film having a transparent base; a near infrared ray absorbing layer that contains a near infrared ray absorbent having a maximum absorption wavelength of from 750 nm to 920 nm; and at least one near infrared ray reflection layer obtained by fixing a cholesteric liquid crystal phase, wherein the near infrared ray absorbent is a compound represented by the following general formula (1):

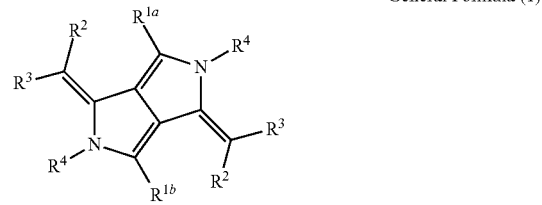

General Formula (1)

wherein in the general formula (1), $R^{1a}$ and $R^{1b}$ may be the same as or different from each other and each independently represent an alkyl group, an aryl group, or a heteroaryl group; $R^2$ and $R^3$ each independently represent a hydrogen atom or a substituent, at least one of $R^2$ and $R^3$ is an electron-withdrawing group, and $R^2$ and $R^3$ may be bonded to each other to form a ring; and $R^4$ represents a hydrogen atom, an alkyl group, an aryl group, a heteroaryl group, substituted boron, or a metal atom, and $R^4$ may be bonded to at least one of $R^{1a}$, $R^{1b}$, and $R^3$ by a covalent bond or a coordinate bond; and wherein the transparent base, the at least one near infrared ray reflection layer and the near infrared ray absorbing layer are laminated in this order; and wherein at least one layer among all near infrared ray reflection layers has a maximum value of reflectance at 750 nm to 900 nm of 40% or more.

2. The infrared ray cutting film according to claim 1, wherein the near infrared ray absorbent has an absorbance at 550 nm of 0.1 or less when absorbance thereof at the maximum absorption wavelength is 1.

3. The infrared ray cutting film according to claim 1, wherein the near infrared ray absorbent is in a state in which fine particles of the compound represented by the general formula (1) are dispersed.

4. The infrared ray cutting film according to claim 3, wherein the fine particles of the compound represented by the general formula (1) has a number average particle diameter of from 5 nm to 500 nm.

5. The infrared ray cutting film according to claim 3, wherein the near infrared ray absorbing layer has fine particles of the compound represented by the general formula (1) which are dispersed in a UV curable resin or a thermoplastic resin.

6. The infrared ray cutting film according to claim 1, wherein the near infrared ray absorbing layer is formed by coating.

7. The infrared ray cutting film according to claim 1, wherein the near infrared ray reflection layer is obtained by applying a cholesteric liquid crystal formed of a polymerizable liquid crystal, aligning the polymerizable liquid crystal, and fixing the cholesteric liquid crystal through photopolymerization.

8. The infrared ray cutting film according to claim 1, wherein the near infrared ray reflection layer includes reflection layers obtained by fixing two layers of cholesteric liquid crystal phases which reflect circularly polarized light beams in directions opposite to each other and whose reflection wavelength regions are in the range of 750 nm to 900 nm and center reflection wavelengths are equivalent to each other.

9. The infrared ray cutting film according to claim 1, which further contains at least one of a metal fine particle dispersion and a diimmonium pigment.

10. The infrared ray cutting film according to claim 9, wherein the metal fine particle dispersion is a composite tungsten oxide represented by the following general formula (I);

$$M_xWO_y \qquad (I)$$

wherein M represents at least one element selected from the group consisting of Cs, Na, Rb, K, Ti, In, Ba, Li, Ca, Sr, Fe, and Sn; W represents tungsten; O represents oxygen; and $0.1 \leq x \leq 0.5$ and $2.2 \leq y \leq 3.0$.

11. The infrared ray cutting film according to claim 1, which further has at least one selected from an easily-adhesive layer, a hard coat layer, a UV absorbing layer, an adhesive layer, and a surface protective layer.

12. An infrared ray cutting laminated glass having two sheets of glass plates; and an infrared ray cutting film which is interposed between the glass plates, wherein the infrared ray cutting film has a transparent base; a near infrared ray absorbing layer that contains a near infrared ray absorbent having a maximum absorption wavelength of from 750 nm to 920 nm; and at least one near infrared ray reflection layer obtained by fixing a cholesteric liquid crystal phase, in which the near infrared ray absorbent is a compound represented by the following general formula (1):

General Formula (1)

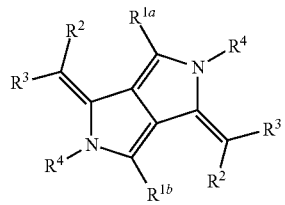

wherein in the general formula (1), $R^{1a}$ and $R^{1b}$ may be the same as or different from each other and each independently represent an alkyl group, an aryl group, or a heteroaryl group; $R^2$ and $R^3$ each independently represent a hydrogen atom or a substituent, at least one of $R^2$ and $R^3$ is an electron-withdrawing group, and $R^2$ and $R^3$ may be bonded to each other to form a ring; and $R^4$ represents a hydrogen atom, an alkyl group, an aryl group, a heteroaryl group, substituted boron, or a metal atom, and $R^4$ may be bonded to at least one of $R^{1a}$, $R^{1b}$, and $R^3$ by a covalent bond or a coordinate bond.

13. A window having an infrared ray cutting film,
wherein the infrared ray cutting film has a transparent base; a near infrared ray absorbing layer that contains a near infrared ray absorbent having a maximum absorption wavelength of from 750 nm to 920 nm; and at least one near infrared ray reflection layer obtained by fixing a cholesteric liquid crystal phase, in which the near infrared ray absorbent is a compound represented by the following general formula (1):

General Formula (1)

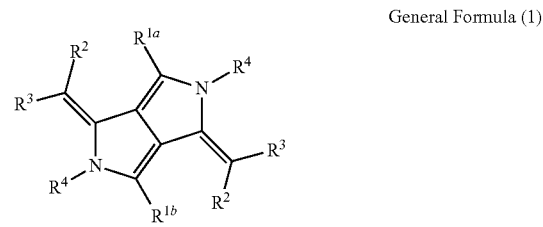

wherein in the general formula (1), $R^{1a}$ and $R^{1b}$ may be the same as or different from each other and each independently represent an alkyl group, an aryl group, or a heteroaryl group; $R^2$ and $R^3$ each independently represent a hydrogen atom or a substituent, at least one of $R^2$ and $R^3$ is an electron-withdrawing group, and $R^2$ and $R^3$ may be bonded to each other to form a ring; and $R^4$ represents a hydrogen atom, an alkyl group, an aryl group, a heteroaryl group, substituted boron, or a metal atom, and $R^4$ may be bonded to at least one of $R^{1a}$, $R^{1b}$, and $R^3$ by a covalent bond or a coordinate bond.

14. The window according to claim 13 which is used for a building and a vehicle.

15. The window according to claim 13 which is used for a windshield of a vehicle.

* * * * *